US012577318B2

(12) United States Patent (10) Patent No.: US 12,577,318 B2
Zatovicova et al. (45) Date of Patent: ***Mar. 17, 2026

(54) HUMANIZED ANTI-CA IX ANTIBODIES AND METHODS OF THEIR USE

(71) Applicant: MABPRO A.S., Bratislava (SK)

(72) Inventors: Miriam Zatovicova, Bratislava (SK);
Silvia Pastorekova, Stupava (SK);
Martina Takacova, Bratislava (SK);
Monika Barathova, Bratislava (SK);
Jaromir Pastorek, Stupava (SK)

(73) Assignee: MABPRO A.S., Bratislava (SK)

( * ) Notice: Subject to any disclaimer, the term of this patent is extended or adjusted under 35 U.S.C. 154(b) by 944 days.

This patent is subject to a terminal disclaimer.

(21) Appl. No.: 17/772,980

(22) PCT Filed: Nov. 5, 2019

(86) PCT No.: PCT/IB2019/059492
§ 371 (c)(1),
(2) Date: Apr. 28, 2022

(87) PCT Pub. No.: WO2021/090046
PCT Pub. Date: May 14, 2021

(65) Prior Publication Data
US 2024/0150490 A1 May 9, 2024

(51) Int. Cl.
| | |
|---|---|
| *C07K 16/30* | (2006.01) |
| *A61K 39/395* | (2006.01) |
| *A61P 35/00* | (2006.01) |
| *C07K 16/40* | (2006.01) |
| *G01N 33/574* | (2006.01) |
| *A61K 39/00* | (2006.01) |

(52) U.S. Cl.
CPC .............. *C07K 16/30* (2013.01); *A61P 35/00* (2018.01); *C07K 16/40* (2013.01); *G01N 33/574* (2013.01); *A61K 2039/54* (2013.01); *A61K 2039/545* (2013.01); *C07K 2317/24* (2013.01); *C07K 2317/565* (2013.01); *C07K 2317/732* (2013.01); *C07K 2317/734* (2013.01); *C07K 2317/77* (2013.01)

(58) Field of Classification Search
None
See application file for complete search history.

(56) References Cited

U.S. PATENT DOCUMENTS 5,387,676 A 2/1995 Zavada et al.

FOREIGN PATENT DOCUMENTS

WO WO-03100029 A2 * 12/2003 ......... A01K 67/0276

OTHER PUBLICATIONS

Zatovicova et al (2010, Current Pharmaceutical Design, 16:3255-3263).*
Zatovicova et al (2003, Journal of Immunological Methods, 282:117-134).*
Kumagai et al (Encyclopedia of Life Sciences, 2001).*
Wong et al (Frontiers in Immunology, Oct. 2019:2454, internet pp. 1-11).*
Edwards et al (Journal of Molecular Biology, 2003, 334:103-118).*
Zatovicova M, et al., "Carbonic Anhydrase IX as an Anticancer Therapy Target: Preclinical Evaluation of Internalizing Monoclonal Antibody Directed to Catalytic Domain", Domain11 , Current Pharmaceutical Design, vol. 16, No. 29, Oct. 2010 (Oct. 1, 2010), pp. 3255-3263, XP055650435, NL ISSN: 1381-6128, http://dx.doi.org/10.2174/138161210793429832 , retrieved Apr. 28, 2022.
Zatovicova M et al: "Monoclonal antibodies generated in carbonic anhydrase IX-deficient mice recognize differentdomains of tumour-associatedhypoxia-induced carbonic anhydrase IX", Journal of Immunological Methods, Elsevier Science Publishers B.V.,Amsterdam, NL, vol. 282, No. 1-2,Nov. 1, 2003 (Nov. 1, 2003), pp. 117-134, XP004471807, ISSN: 0022-1759, http://dx.doi.org/10.1016/j.jim.2003.08.011 , retrieved Apr. 28, 2022.
De-Kuan Chang et al: "Human anti-CAIX antibodies mediate inmune cell inhibition of renal cell carcinoma in vitro and in a humanized mouse model in vivo", Molecular Cancer, Biomed Central, London, GB, vol. 14, No. 119, Jun. 11, 2015 (Jun. 11, 2015), pp. 1-13, XP021224075, ISSN: 1476-4598, http://dx.doi.org/10.1186/s12943-015-0384-3 , retrieved Apr. 28, 2022.
I Bleumer et al: "A phase II trial of chimeric monoclonal antibody 6250 for advanced renal cell carcinoma patients", British Journal of Cancer, vol. 90, No. 5, Mar. 1, 2004 (Mar. 1, 2004), pp. 985-990, XP055712916, GB ISSN: 0007-0920, http://dx.doi.org/10.1038/sj.bjc.6601617 , retrieved Apr. 28, 2022.
International Search Report and Written Opinion for corresponding PCT application No. PCT/IB2019/059492, mailed Jul. 20, 2020.

* cited by examiner

*Primary Examiner* — Laura B Goddard
(74) *Attorney, Agent, or Firm* — Notaro, Michalos & Zaccaria P.C.

(57) ABSTRACT

A humanized antibody specifically recognizing human CA IX, and to therapeutic and diagnostic methods utilizing this antibody is disclosed. The methods relate in particular to treatment or diagnosis of cancers selected from squamous cell carcinoma, myeloma, small-cell lung cancer, non-small cell lung cancer, glioma, hodgkin's lymphoma, non-hodgkin's lymphoma, acute myeloid leukemia, multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, mesothelioma, and head and neck cancer.

21 Claims, 6 Drawing Sheets

Specification includes a Sequence Listing.

projection of Z-stack sections
after 3 days of treatment immunohistochemistry
after 11 days of treatment

SEQUENCE LISTING

<160> NUMBER OF SEQ ID NOS: 66

<210> SEQ ID NO 1
<211> LENGTH: 10
<212> TYPE: PRT
<213> ORGANISM: artificial
<220> FEATURE:
<223> OTHER INFORMATION: CDR1 VH VII/20

<400> SEQUENCE: 1

Gly Phe Thr Phe Thr Asp Tyr Tyr Met His
1               5                   10

<210> SEQ ID NO 2
<211> LENGTH: 19
<212> TYPE: PRT
<213> ORGANISM: artificial
<220> FEATURE:
<223> OTHER INFORMATION: CDR2 VH VII/20

```
<400> SEQUENCE: 2

Phe Ile Arg Asn Lys Ala Ser Gly Tyr Thr Pro Gln Tyr Ser Ala Ser
1               5                   10                  15

Val Lys Gly

<210> SEQ ID NO 3
<211> LENGTH: 15
<212> TYPE: PRT
<213> ORGANISM: artificial
<220> FEATURE:
<223> OTHER INFORMATION: CDR3 VH VII/20

<400> SEQUENCE: 3

Val Arg Gly Gly His Ala Gly Ser Asn Tyr Trp Tyr Phe Asp Val
1               5                   10                  15

<210> SEQ ID NO 4
<211> LENGTH: 124
<212> TYPE: PRT
<213> ORGANISM: artificial
<220> FEATURE:
<223> OTHER INFORMATION: HC1 CA9hu-1

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Tyr Met His Trp Val Arg Gln Ala Pro Gly Lys Gly Leu Glu Trp Val
            35                  40                  45

Ala Phe Ile Arg Asn Lys Ala Ser Gly Tyr Thr Pro Gln Tyr Ser Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Ile Glu Asp Thr Ala Val Tyr
                85                  90                  95

Tyr Cys Val Arg Gly Gly His Ala Gly Ser Asn Tyr Trp Tyr Phe Asp
            100                 105                 110

Val Trp Gly Gln Gly Thr Thr Val Thr Val Ser Ser
        115                 120

<210> SEQ ID NO 5
<211> LENGTH: 124
<212> TYPE: PRT
<213> ORGANISM: artificial
<220> FEATURE:
<223> OTHER INFORMATION: HC2 CA9hu-1

<400> SEQUENCE: 5

Glu Val Arg Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Tyr Met His Trp Val Arg Gln Ala Pro Gly Lys Gly Leu Glu Trp Leu
            35                  40                  45

Gly Phe Ile Arg Asn Lys Ala Ser Gly Tyr Thr Pro Gln Tyr Ser Ala
        50                  55                  60

Ser Val Lys Gly Arg Phe Thr Ile Ser Arg Asp Asp Ser Thr Asn Ser
65                  70                  75                  80
```

-continued

```
Leu Tyr Leu Gln Met Asn Ser Leu Lys Thr Glu Asp Thr Ala Ile Tyr
                85                  90                  95

Tyr Cys Val Arg Gly Gly His Ala Gly Ser Asn Tyr Trp Tyr Phe Asp
                100                 105                 110

Val Trp Gly Gln Gly Thr Leu Val Thr Val Ser Ser
        115                 120
```

```
<210> SEQ ID NO 6
<211> LENGTH: 124
<212> TYPE: PRT
<213> ORGANISM: artificial
<220> FEATURE:
<223> OTHER INFORMATION: HC3 CA9hu-1

<400> SEQUENCE: 6
```

```
Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Thr Asp Tyr
                20                  25                  30

Tyr Met His Trp Val Arg Gln Ala Pro Gly Lys Gly Leu Glu Trp Val
        35                  40                  45

Gly Phe Ile Arg Asn Lys Ala Ser Gly Tyr Thr Pro Gln Tyr Ser Ala
    50                  55                  60

Ser Val Lys Gly Arg Phe Thr Ile Ser Arg Asp Asp Ser Lys Thr Ile
65                  70                  75                  80

Ala Tyr Leu Gln Met Asn Ser Leu Lys Thr Glu Asp Thr Ala Val Tyr
                85                  90                  95

Tyr Cys Val Arg Gly Gly His Ala Gly Ser Asn Tyr Trp Tyr Phe Asp
                100                 105                 110

Val Trp Gly Gln Gly Thr Leu Val Thr Val Ser Ser
        115                 120
```

```
<210> SEQ ID NO 7
<211> LENGTH: 124
<212> TYPE: PRT
<213> ORGANISM: artificial
<220> FEATURE:
<223> OTHER INFORMATION: HC4 CA9hu-1

<400> SEQUENCE: 7
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Tyr Met His Trp Val Arg Gln Ala Pro Gly Arg Gly Leu Glu Trp Val
        35                  40                  45

Ala Phe Ile Arg Asn Lys Ala Ser Gly Tyr Thr Pro Gln Tyr Ser Ala
    50                  55                  60

Ser Val Lys Gly Arg Phe Thr Ile Ser Arg Asp Asn Ala Glu Asn Ser
65                  70                  75                  80

Leu Tyr Leu Gln Met Asn Ser Leu Arg Ala Glu Asp Thr Ala Val Tyr
                85                  90                  95

Tyr Cys Val Arg Gly Gly His Ala Gly Ser Asn Tyr Trp Tyr Phe Asp
                100                 105                 110

Val Trp Gly Lys Gly Thr Thr Val Thr Val Ser Ser
        115                 120
```

```
<210> SEQ ID NO 8
<211> LENGTH: 124
<212> TYPE: PRT
<213> ORGANISM: artificial
<220> FEATURE:
<223> OTHER INFORMATION: HC5 CA9hu-1

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met His Trp Val Arg Gln Ala Pro Gly Lys Gly Leu Glu Trp Val
        35                  40                  45

Gly Phe Ile Arg Asn Lys Ala Ser Gly Tyr Thr Pro Gln Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg Gly Gly His Ala Gly Ser Asn Tyr Trp Tyr Phe Asp
            100                 105                 110

Val Trp Gly Gln Gly Thr Met Val Thr Val Ser Ser
        115                 120

<210> SEQ ID NO 9
<211> LENGTH: 11
<212> TYPE: PRT
<213> ORGANISM: artificial
<220> FEATURE:
<223> OTHER INFORMATION: CDR1 VL VII/20

<400> SEQUENCE: 9

His Val Ser Gln Asn Ile Asn Val Trp Leu Ser
1               5                   10

<210> SEQ ID NO 10
<211> LENGTH: 7
<212> TYPE: PRT
<213> ORGANISM: artificial
<220> FEATURE:
<223> OTHER INFORMATION: CDR2 VL VII/20

<400> SEQUENCE: 10

Gln Ala Ser Asn Leu His Thr
1               5

<210> SEQ ID NO 11
<211> LENGTH: 9
<212> TYPE: PRT
<213> ORGANISM: artificial
<220> FEATURE:
<223> OTHER INFORMATION: CDR3 VL VII/20

<400> SEQUENCE: 11

Gln Gln Gly Gln Ser Tyr Pro Phe Thr
1               5

<210> SEQ ID NO 12
<211> LENGTH: 107
<212> TYPE: PRT
<213> ORGANISM: artificial
<220> FEATURE:
<223> OTHER INFORMATION: LC1 CA9hu-1
```

```
<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys His Val Ser Gln Asn Ile Asn Val Trp
            20                  25                  30

Leu Ser Trp Tyr Gln Gln Lys Pro Gly Lys Ala Pro Asn Leu Leu Ile
        35                  40                  45

Tyr Gln Ala Ser Asn Leu His Thr Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Phe
                85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: artificial
<220> FEATURE:
<223> OTHER INFORMATION: LC2 CA9hu-1

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys His Val Ser Gln Asn Ile Asn Val Trp
            20                  25                  30

Leu Ser Trp Tyr Gln Gln Lys Pro Gly Asn Ala Pro Lys Leu Leu Ile
        35                  40                  45

Tyr Gln Ala Ser Asn Leu His Thr Gly Val Pro Ser Arg Phe Ser Gly
    50                  55                  60

Ser Gly Ser Gly Thr Glu Phe Thr Leu Thr Ile Gly Ser Leu Gln Pro
65                  70                  75                  80

Asp Asp Phe Val Thr Tyr Tyr Cys Gln Gln Gly Gln Ser Tyr Pro Phe
                85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: artificial
<220> FEATURE:
<223> OTHER INFORMATION: LC3 CA9hu-1

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys His Val Ser Gln Asn Ile Asn Val Trp
            20                  25                  30

Leu Ser Trp Tyr Gln Gln Lys Pro Gly Glu Ala Pro Lys Leu Leu Ile
        35                  40                  45

Tyr Gln Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln Gly Gln Ser Tyr Pro Phe
            85                  90                  95

Thr Phe Gly Gln Gly Thr Lys Leu Glu Ile Lys
            100                 105

<210> SEQ ID NO 15
<211> LENGTH: 107
<212> TYPE: PRT
<213> ORGANISM: artificial
<220> FEATURE:
<223> OTHER INFORMATION: LC4 CA9hu-1

<400> SEQUENCE: 15

Asp Ile Gln Met Thr Gln Ser Pro Ser Ser Leu Ser Ala Ser Val Gly
1               5                   10                  15

Asp Arg Val Thr Ile Asn Cys His Val Ser Gln Asn Ile Asn Val Trp
            20                  25                  30

Leu Ser Trp Tyr Gln Gln Lys Pro Gly Glu Ala Pro Lys Leu Leu Ile
         35                  40                  45

Tyr Gln Ala Ser Asn Leu His Thr Gly Val Pro Ser Arg Phe Ser Gly
      50                  55                  60

Ser Gly Ser Gly Thr Gly Phe Thr Leu Thr Ile Arg Ser Leu Gln Pro
65                  70                  75                  80

Glu Asp Tyr Ala Thr Tyr Tyr Cys Gln Gln Gly Gln Ser Tyr Pro Phe
            85                  90                  95

Thr Phe Gly Gln Gly Thr Lys Leu Glu Ile Lys
            100                 105

<210> SEQ ID NO 16
<211> LENGTH: 107
<212> TYPE: PRT
<213> ORGANISM: artificial
<220> FEATURE:
<223> OTHER INFORMATION: LC5 CA9hu-1

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys His Val Ser Gln Asn Ile Asn Val Trp
            20                  25                  30

Leu Ser Trp Tyr Gln Gln Lys Pro Gly Lys Ala Pro Lys Leu Leu Ile
         35                  40                  45

Tyr Gln Ala Ser Asn Leu His Thr Gly Val Pro Ser Arg Phe Ser Gly
      50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Phe
            85                  90                  95

Thr Phe Gly Gln Gly Thr Lys Leu Glu Ile Lys
            100                 105

<210> SEQ ID NO 17
<211> LENGTH: 10
<212> TYPE: PRT
<213> ORGANISM: artificial
<220> FEATURE:
<223> OTHER INFORMATION: CDR1 VH IV/18

<400> SEQUENCE: 17
```

```
Gly Phe Thr Phe Asn Thr Asn Ala Met His
1               5                   10

<210> SEQ ID NO 18
<211> LENGTH: 19
<212> TYPE: PRT
<213> ORGANISM: artificial
<220> FEATURE:
<223> OTHER INFORMATION: CDR2 VH IV/18

<400> SEQUENCE: 18

Arg Ile Arg Ser Lys Ser Asn Asn Tyr Thr Thr Tyr Tyr Ala Asp Ser
1               5                   10                  15

Val Lys Asp

<210> SEQ ID NO 19
<211> LENGTH: 8
<212> TYPE: PRT
<213> ORGANISM: artificial
<220> FEATURE:
<223> OTHER INFORMATION: CDR3 VH IV/18

<400> SEQUENCE: 19

Val Cys Gly Ser Trp Phe Ala Tyr
1               5

<210> SEQ ID NO 20
<211> LENGTH: 117
<212> TYPE: PRT
<213> ORGANISM: artificial
<220> FEATURE:
<223> OTHER INFORMATION: HC1 CA9hu-2

<400> SEQUENCE: 20

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Asn
            20                  25                  30

Ala Met His Trp Val Arg Gln Ala Ser Gly Lys Gly Leu Glu Trp Val
        35                  40                  45

Gly Arg Ile Arg Ser Lys Ser Asn Asn Tyr Thr Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Cys Gly Ser Trp Phe Ala Tyr Trp Gly Gln Gly Thr Leu
            100                 105                 110

Val Thr Val Ser Ser
        115

<210> SEQ ID NO 21
<211> LENGTH: 117
<212> TYPE: PRT
<213> ORGANISM: artificial
<220> FEATURE:
<223> OTHER INFORMATION: HC2 CA9hu-2

<400> SEQUENCE: 21

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Asn
```

-continued

```
              20              25              30

Ala Met His Trp Val Arg Gln Ala Ser Gly Lys Gly Leu Glu Trp Val
              35              40              45

Gly Arg Ile Arg Ser Lys Ser Asn Asn Tyr Thr Thr Tyr Tyr Ala Asp
      50              55              60

Ser Val Lys Asp Arg Phe Thr Ile Ser Arg Asp Asp Ser Lys Ser Thr
65              70              75              80

Ala Tyr Leu Gln Met Asn Ser Leu Lys Thr Glu Asp Thr Ala Val Tyr
                  85              90              95

Tyr Cys Val Cys Gly Ser Trp Phe Ala Tyr Trp Gly Gln Gly Thr Leu
                  100             105             110

Val Thr Val Ser Ser
          115
```

<210> SEQ ID NO 22
<211> LENGTH: 117
<212> TYPE: PRT
<213> ORGANISM: artificial
<220> FEATURE:
<223> OTHER INFORMATION: HC3 CA9hu-2

<400> SEQUENCE: 22

```
Gln Val Gln Leu Val Glu Ser Gly Gly Gly Val Val Gln Pro Gly Gly
1               5               10              15

Ser Leu Arg Leu Ser Cys Ala Ala Ser Gly Phe Thr Phe Asn Thr Asn
              20              25              30

Ala Met His Trp Val Arg Gln Ala Pro Gly Arg Gly Leu Glu Trp Val
              35              40              45

Ala Arg Ile Arg Ser Lys Ser Asn Asn Tyr Thr Thr Tyr Tyr Ala Asp
      50              55              60

Ser Val Lys Asp Arg Phe Thr Ile Ser Arg Asp Asn Ser Lys Asn Thr
65              70              75              80

Leu Tyr Leu Gln Val Asn Ser Leu Arg Ala Glu Asp Thr Ala Val Tyr
                  85              90              95

Tyr Cys Val Cys Gly Ser Trp Phe Ala Tyr Trp Gly Gln Gly Thr Leu
                  100             105             110

Val Thr Val Ser Ser
          115
```

<210> SEQ ID NO 23
<211> LENGTH: 117
<212> TYPE: PRT
<213> ORGANISM: artificial
<220> FEATURE:
<223> OTHER INFORMATION: HC4 CA9hu-2

<400> SEQUENCE: 23

```
Glu Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Asn Thr Asn
              20              25              30

Ala Met His Trp Val Arg Gln Ala Pro Gly Lys Gly Leu Glu Trp Val
              35              40              45

Ala Arg Ile Arg Ser Lys Ser Asn Asn Tyr Thr Thr Tyr Tyr Ala Asp
      50              55              60

Ser Val Lys Asp Arg Phe Thr Ile Ser Arg Asp Asn Ser Lys Asn Thr
65              70              75              80
```

```
Leu Tyr Leu Gln Met Asn Ser Leu Arg Ala Glu Asp Thr Ala Val Tyr
                85                  90                  95

Tyr Cys Val Cys Gly Ser Trp Phe Ala Tyr Trp Gly Gln Gly Thr Leu
            100                 105                 110

Val Thr Val Ser Ser
        115

<210> SEQ ID NO 24
<211> LENGTH: 117
<212> TYPE: PRT
<213> ORGANISM: artificial
<220> FEATURE:
<223> OTHER INFORMATION: HC5 CA9hu-2

<400> SEQUENCE: 24

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Asn
            20                  25                  30

Ala Met His Trp Val Arg Gln Ala Ser Gly Lys Gly Leu Glu Trp Val
        35                  40                  45

Gly Arg Ile Arg Ser Lys Ser Asn Asn Tyr Thr Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Cys Gly Ser Trp Phe Ala Tyr Trp Gly Gln Gly Thr Thr
            100                 105                 110

Val Thr Val Ser Ser
        115

<210> SEQ ID NO 25
<211> LENGTH: 17
<212> TYPE: PRT
<213> ORGANISM: artificial
<220> FEATURE:
<223> OTHER INFORMATION: CDR1 VL IV/18

<400> SEQUENCE: 25

Lys Ser Ser Gln Ser Leu Leu Asn Ser Ser Asn Gln Lys Asn Tyr Leu
1               5                   10                  15

Ala

<210> SEQ ID NO 26
<211> LENGTH: 7
<212> TYPE: PRT
<213> ORGANISM: artificial
<220> FEATURE:
<223> OTHER INFORMATION: CDR2 VL IV/18

<400> SEQUENCE: 26

Phe Thr Ser Thr Arg Gln Ser
1               5

<210> SEQ ID NO 27
<211> LENGTH: 9
<212> TYPE: PRT
<213> ORGANISM: artificial
<220> FEATURE:
<223> OTHER INFORMATION: CDR3 VL IV/18
```

<400> SEQUENCE: 27

Gln Gln His Tyr Ser Ile Pro Leu Thr
1               5

<210> SEQ ID NO 28
<211> LENGTH: 113
<212> TYPE: PRT
<213> ORGANISM: artificial
<220> FEATURE:
<223> OTHER INFORMATION: LC1 CA9hu-2

<400> SEQUENCE: 28

Asp Val Val Met Thr Gln Ser Pro Asp Ser Leu Ala Val Ser Leu Gly
1               5                   10                  15

Glu Arg Val Thr Ile Asn Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Phe Thr Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Ile Pro Leu Thr Phe Gly Gln Gly Thr Lys Leu Glu Ile
            100                 105                 110

Lys

<210> SEQ ID NO 29
<211> LENGTH: 113
<212> TYPE: PRT
<213> ORGANISM: artificial
<220> FEATURE:
<223> OTHER INFORMATION: LC2 CA9hu-2

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Phe Gln Gln Lys Pro Gly Gln
        35                  40                  45

Pro Pro Asn Leu Val Ile Tyr Phe Thr Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Gln Gln
                85                  90                  95

His Tyr Ser Ile Pro Leu Thr Phe Gly Gln Gly Thr Gln Val Glu Ile
            100                 105                 110

Lys

<210> SEQ ID NO 30
<211> LENGTH: 113
<212> TYPE: PRT
<213> ORGANISM: artificial
<220> FEATURE:
<223> OTHER INFORMATION: LC3 CA9hu-2

```
<400> SEQUENCE: 30

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Phe Thr Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ser Ile Pro Leu Thr Phe Gly Gln Gly Thr Lys Val Glu Ile
            100                 105                 110

Lys

<210> SEQ ID NO 31
<211> LENGTH: 113
<212> TYPE: PRT
<213> ORGANISM: artificial
<220> FEATURE:
<223> OTHER INFORMATION: LC4 CA9hu-2

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Phe Gln Gln Lys Pro Gly Gln
        35                  40                  45

Pro Pro Lys Val Leu Ile Tyr Phe Thr Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Ile Pro Leu Thr Phe Gly Gln Gly Thr Lys Leu Glu Ile
            100                 105                 110

Lys

<210> SEQ ID NO 32
<211> LENGTH: 113
<212> TYPE: PRT
<213> ORGANISM: artificial
<220> FEATURE:
<223> OTHER INFORMATION: LC5 CA9hu-2

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Phe Thr Ser Thr Arg Gln Ser Gly Val
    50                  55                  60
```

```
Pro Asp Arg Phe Ser Gly Ser Gly Ser Gly Thr Asp Phe Thr Leu Thr
65               70              75              80

Ile Ser Ser Leu Gln Ala Glu Asp Val Ala Val Tyr Tyr Cys Gln Gln
                85              90              95

His Tyr Ser Ile Pro Leu Thr Phe Gly Gln Gly Thr Lys Leu Glu Ile
        100             105             110

Lys

<210> SEQ ID NO 33
<211> LENGTH: 123
<212> TYPE: PRT
<213> ORGANISM: artificial
<220> FEATURE:
<223> OTHER INFORMATION: HC CA9hu-1
<220> FEATURE:
<221> NAME/KEY: VARIANT
<222> LOCATION: (1)..(1)
<223> OTHER INFORMATION: E or Q
<220> FEATURE:
<221> NAME/KEY: VARIANT
<222> LOCATION: (3)..(3)
<223> OTHER INFORMATION: Q or R
<220> FEATURE:
<221> NAME/KEY: VARIANT
<222> LOCATION: (6)..(6)
<223> OTHER INFORMATION: E or Q
<220> FEATURE:
<221> NAME/KEY: VARIANT
<222> LOCATION: (16)..(16)
<223> OTHER INFORMATION: G or R
<220> FEATURE:
<221> NAME/KEY: VARIANT
<222> LOCATION: (23)..(23)
<223> OTHER INFORMATION: A or T
<220> FEATURE:
<221> NAME/KEY: VARIANT
<222> LOCATION: (43)..(43)
<223> OTHER INFORMATION: K or R
<220> FEATURE:
<221> NAME/KEY: VARIANT
<222> LOCATION: (48)..(48)
<223> OTHER INFORMATION: V or L
<220> FEATURE:
<221> NAME/KEY: VARIANT
<222> LOCATION: (49)..(49)
<223> OTHER INFORMATION: A or G
<220> FEATURE:
<221> NAME/KEY: VARIANT
<222> LOCATION: (76)..(76)
<223> OTHER INFORMATION: D or N
<220> FEATURE:
<221> NAME/KEY: VARIANT
<222> LOCATION: (77)..(77)
<223> OTHER INFORMATION: S or A
<220> FEATURE:
<221> NAME/KEY: VARIANT
<222> LOCATION: (78)..(78)
<223> OTHER INFORMATION: K or T or E
<220> FEATURE:
<221> NAME/KEY: VARIANT
<222> LOCATION: (79)..(79)
<223> OTHER INFORMATION: N or T
<220> FEATURE:
<221> NAME/KEY: VARIANT
<222> LOCATION: (80)..(80)
<223> OTHER INFORMATION: S or I
<220> FEATURE:
<221> NAME/KEY: VARIANT
<222> LOCATION: (81)..(81)
<223> OTHER INFORMATION: L or A
<220> FEATURE:
<221> NAME/KEY: VARIANT
<222> LOCATION: (89)..(89)
<223> OTHER INFORMATION: K or R
```

```
<220> FEATURE:
<221> NAME/KEY: VARIANT
<222> LOCATION: (90)..(90)
<223> OTHER INFORMATION: T or A or I
<220> FEATURE:
<221> NAME/KEY: VARIANT
<222> LOCATION: (95)..(95)
<223> OTHER INFORMATION: V or I
<220> FEATURE:
<221> NAME/KEY: VARIANT
<222> LOCATION: (115)..(115)
<223> OTHER INFORMATION: Q or K
<220> FEATURE:
<221> NAME/KEY: VARIANT
<222> LOCATION: (118)..(118)
<223> OTHER INFORMATION: T or L or M

<400> SEQUENCE: 33

Xaa Val Xaa Leu Val Xaa Ser Gly Gly Gly Leu Val Gln Pro Gly Xaa
1               5                   10                  15

Ser Leu Arg Leu Ser Cys Xaa Ala Ser Gly Phe Thr Phe Thr Asp Tyr
            20                  25                  30

Tyr Met His Trp Val Arg Gln Ala Pro Gly Xaa Gly Leu Glu Trp Xaa
            35                  40                  45

Xaa Phe Ile Arg Asn Lys Ala Ser Gly Tyr Thr Pro Gln Tyr Ser Ala
    50                  55                  60

Ser Val Lys Gly Arg Phe Thr Ile Ser Arg Asp Xaa Xaa Xaa Xaa Xaa
65                  70                  75                  80

Xaa Tyr Leu Gln Met Asn Ser Leu Xaa Xaa Glu Asp Thr Ala Xaa Tyr
                85                  90                  95

Tyr Val Arg Gly Gly His Ala Gly Ser Asn Tyr Trp Tyr Phe Asp Val
            100                 105                 110

Trp Gly Xaa Gly Thr Xaa Val Thr Val Ser Ser
        115                 120

<210> SEQ ID NO 34
<211> LENGTH: 107
<212> TYPE: PRT
<213> ORGANISM: artificial
<220> FEATURE:
<223> OTHER INFORMATION: LC CA9hu-1
<220> FEATURE:
<221> NAME/KEY: VARIANT
<222> LOCATION: (10)..(10)
<223> OTHER INFORMATION: S or T
<220> FEATURE:
<221> NAME/KEY: VARIANT
<222> LOCATION: (22)..(22)
<223> OTHER INFORMATION: T or N
<220> FEATURE:
<221> NAME/KEY: VARIANT
<222> LOCATION: (42)..(42)
<223> OTHER INFORMATION: K or N or E
<220> FEATURE:
<221> NAME/KEY: VARIANT
<222> LOCATION: (45)..(45)
<223> OTHER INFORMATION: N or K
<220> FEATURE:
<221> NAME/KEY: VARIANT
<222> LOCATION: (70)..(70)
<223> OTHER INFORMATION: H or E or D or G
<220> FEATURE:
<221> NAME/KEY: VARIANT
<222> LOCATION: (73)..(73)
<223> OTHER INFORMATION: L or F
<220> FEATURE:
<221> NAME/KEY: VARIANT
<222> LOCATION: (76)..(76)
<223> OTHER INFORMATION: S or G or R
<220> FEATURE:
```

```
<221> NAME/KEY: VARIANT
<222> LOCATION: (81)..(81)
<223> OTHER INFORMATION: E or D
<220> FEATURE:
<221> NAME/KEY: VARIANT
<222> LOCATION: (83)..(83)
<223> OTHER INFORMATION: I or F or Y
<220> FEATURE:
<221> NAME/KEY: VARIANT
<222> LOCATION: (84)..(84)
<223> OTHER INFORMATION: A or V
<220> FEATURE:
<221> NAME/KEY: VARIANT
<222> LOCATION: (100)..(100)
<223> OTHER INFORMATION: Q or G
<220> FEATURE:
<221> NAME/KEY: VARIANT
<222> LOCATION: (104)..(104)
<223> OTHER INFORMATION: V or L

<400> SEQUENCE: 34

Asp Ile Gln Met Thr Gln Ser Pro Ser Xaa Leu Ser Ala Ser Val Gly
1               5                   10                  15

Asp Arg Val Thr Ile Xaa Cys His Val Ser Gln Asn Ile Asn Val Trp
            20                  25                  30

Leu Ser Trp Tyr Gln Gln Lys Pro Gly Xaa Ala Pro Xaa Leu Leu Ile
        35                  40                  45

Tyr Gln Ala Ser Asn Leu His Thr Gly Val Pro Ser Arg Phe Ser Gly
    50                  55                  60

Ser Gly Ser Gly Thr Xaa Phe Thr Xaa Thr Ile Xaa Ser Leu Gln Pro
65                  70                  75                  80

Xaa Asp Xaa Xaa Thr Tyr Tyr Cys Gln Gln Gly Gln Ser Tyr Pro Phe
                85                  90                  95

Thr Phe Gly Xaa Gly Thr Lys Xaa Glu Ile Lys
            100                 105

<210> SEQ ID NO 35
<211> LENGTH: 117
<212> TYPE: PRT
<213> ORGANISM: artificial
<220> FEATURE:
<223> OTHER INFORMATION: HC CA9hu-2
<220> FEATURE:
<221> NAME/KEY: VARIANT
<222> LOCATION: (1)..(1)
<223> OTHER INFORMATION: E or Q
<220> FEATURE:
<221> NAME/KEY: VARIANT
<222> LOCATION: (11)..(11)
<223> OTHER INFORMATION: L or V
<220> FEATURE:
<221> NAME/KEY: VARIANT
<222> LOCATION: (16)..(16)
<223> OTHER INFORMATION: G or R
<220> FEATURE:
<221> NAME/KEY: VARIANT
<222> LOCATION: (19)..(19)
<223> OTHER INFORMATION: K or R
<220> FEATURE:
<221> NAME/KEY: VARIANT
<222> LOCATION: (41)..(41)
<223> OTHER INFORMATION: S or P
<220> FEATURE:
<221> NAME/KEY: VARIANT
<222> LOCATION: (43)..(43)
<223> OTHER INFORMATION: K or R
<220> FEATURE:
<221> NAME/KEY: VARIANT
<222> LOCATION: (49)..(49)
<223> OTHER INFORMATION: A or G
<220> FEATURE:
```

```
<221> NAME/KEY: VARIANT
<222> LOCATION: (76)..(76)
<223> OTHER INFORMATION: D or N
<220> FEATURE:
<221> NAME/KEY: VARIANT
<222> LOCATION: (79)..(79)
<223> OTHER INFORMATION: N or S
<220> FEATURE:
<221> NAME/KEY: VARIANT
<222> LOCATION: (81)..(81)
<223> OTHER INFORMATION: A or L
<220> FEATURE:
<221> NAME/KEY: VARIANT
<222> LOCATION: (85)..(85)
<223> OTHER INFORMATION: M or V
<220> FEATURE:
<221> NAME/KEY: VARIANT
<222> LOCATION: (89)..(89)
<223> OTHER INFORMATION: K or R
<220> FEATURE:
<221> NAME/KEY: VARIANT
<222> LOCATION: (90)..(90)
<223> OTHER INFORMATION: T or A
<220> FEATURE:
<221> NAME/KEY: VARIANT
<222> LOCATION: (112)..(112)
<223> OTHER INFORMATION: L or T

<400> SEQUENCE: 35

Xaa Val Gln Leu Val Glu Ser Gly Gly Gly Xaa Val Gln Pro Gly Xaa
1               5                   10                  15

Ser Leu Xaa Leu Ser Cys Ala Ala Ser Gly Phe Thr Phe Asn Thr Asn
            20                  25                  30

Ala Met His Trp Val Arg Gln Ala Xaa Gly Xaa Gly Leu Glu Trp Val
        35                  40                  45

Xaa Arg Ile Arg Ser Lys Ser Asn Asn Tyr Thr Thr Tyr Tyr Ala Asp
    50                  55                  60

Ser Val Lys Asp Arg Phe Thr Ile Ser Arg Asp Xaa Ser Lys Xaa Thr
65                  70                  75                  80

Xaa Tyr Leu Gln Xaa Asn Ser Leu Xaa Xaa Glu Asp Thr Ala Val Tyr
                85                  90                  95

Tyr Cys Val Cys Gly Ser Trp Phe Ala Tyr Trp Gly Gln Gly Thr Xaa
            100                 105                 110

Val Thr Val Ser Ser
        115

<210> SEQ ID NO 36
<211> LENGTH: 113
<212> TYPE: PRT
<213> ORGANISM: artificial
<220> FEATURE:
<223> OTHER INFORMATION: LC CA9hu-2
<220> FEATURE:
<221> NAME/KEY: VARIANT
<222> LOCATION: (2)..(2)
<223> OTHER INFORMATION: V or I
<220> FEATURE:
<221> NAME/KEY: VARIANT
<222> LOCATION: (3)..(3)
<223> OTHER INFORMATION: V or Q
<220> FEATURE:
<221> NAME/KEY: VARIANT
<222> LOCATION: (19)..(19)
<223> OTHER INFORMATION: V or A
<220> FEATURE:
<221> NAME/KEY: VARIANT
<222> LOCATION: (42)..(42)
<223> OTHER INFORMATION: Y or F
<220> FEATURE:
<221> NAME/KEY: VARIANT
```

```
<222> LOCATION: (49)..(49)
<223> OTHER INFORMATION: S or P
<220> FEATURE:
<221> NAME/KEY: VARIANT
<222> LOCATION: (51)..(51)
<223> OTHER INFORMATION: K or N
<220> FEATURE:
<221> NAME/KEY: VARIANT
<222> LOCATION: (52)..(52)
<223> OTHER INFORMATION: L or V
<220> FEATURE:
<221> NAME/KEY: VARIANT
<222> LOCATION: (53)..(53)
<223> OTHER INFORMATION: L or V
<220> FEATURE:
<221> NAME/KEY: VARIANT
<222> LOCATION: (69)..(69)
<223> OTHER INFORMATION: S or T
<220> FEATURE:
<221> NAME/KEY: VARIANT
<222> LOCATION: (82)..(82)
<223> OTHER INFORMATION: S or N
<220> FEATURE:
<221> NAME/KEY: VARIANT
<222> LOCATION: (93)..(93)
<223> OTHER INFORMATION: Y or F
<220> FEATURE:
<221> NAME/KEY: VARIANT
<222> LOCATION: (109)..(109)
<223> OTHER INFORMATION: K or Q
<220> FEATURE:
<221> NAME/KEY: VARIANT
<222> LOCATION: (110)..(110)
<223> OTHER INFORMATION: L or V

<400> SEQUENCE: 36

Asp Xaa Xaa Met Thr Gln Ser Pro Asp Ser Leu Ala Val Ser Leu Gly
1               5                   10                  15

Glu Arg Xaa Thr Ile Asn Cys Lys Ser Ser Gln Ser Leu Leu Asn Ser
            20                  25                  30

Ser Asn Gln Lys Asn Tyr Leu Ala Trp Xaa Gln Gln Lys Pro Gly Gln
        35                  40                  45

Xaa Pro Xaa Xaa Xaa Ile Tyr Phe Thr Ser Thr Arg Gln Ser Gly Val
    50                  55                  60

Pro Asp Arg Phe Xaa Gly Ser Gly Ser Gly Thr Asp Phe Thr Leu Thr
65                  70                  75                  80

Ile Xaa Ser Leu Gln Ala Glu Asp Val Ala Val Tyr Xaa Cys Gln Gln
            85                  90                  95

His Tyr Ser Ile Pro Leu Thr Phe Gly Gln Gly Thr Xaa Xaa Glu Ile
            100                 105                 110

Lys

<210> SEQ ID NO 37
<211> LENGTH: 124
<212> TYPE: PRT
<213> ORGANISM: artificial
<220> FEATURE:
<223> OTHER INFORMATION: VH VII/20

<400> SEQUENCE: 37

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met His Trp Val Arg Gln Pro Pro Gly Met Ala Leu Glu Trp Leu
        35                  40                  45
```

```
Ala Phe Ile Arg Asn Lys Ala Ser Gly Tyr Thr Pro Gln Tyr Ser Ala
    50                  55                  60

Ser Val Lys Gly Arg Phe Thr Ile Ser Arg Asp Val Ser Gln Thr Ile
65                  70                  75                  80

Leu Tyr Leu Gln Met Asn Thr Leu Arg Pro Glu Asp Ser Ala Thr Tyr
                85                  90                  95

Tyr Cys Val Arg Gly Gly His Ala Gly Ser Asn Tyr Trp Tyr Phe Asp
            100                 105                 110

Val Trp Gly Ala Gly Thr Thr Val Thr Val Ser Ser
        115                 120

<210> SEQ ID NO 38
<211> LENGTH: 107
<212> TYPE: PRT
<213> ORGANISM: artificial
<220> FEATURE:
<223> OTHER INFORMATION: VL VII/20

<400> SEQUENCE: 38

Asp Ile Gln Met Asn Gln Ser Pro Ser Ser Leu Ser Ala Ser Leu Gly
1               5                   10                  15

Asp Thr Ile Thr Ile Ala Cys His Val Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Gln Ala Ser Asn Leu His Thr Gly Val Pro Ser Arg Phe Thr Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Phe
                85                  90                  95

Thr Phe Gly Ser Gly Thr Lys Leu Glu Ile Lys
            100                 105

<210> SEQ ID NO 39
<211> LENGTH: 117
<212> TYPE: PRT
<213> ORGANISM: artificial
<220> FEATURE:
<223> OTHER INFORMATION: VH IV/18

<400> SEQUENCE: 39

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met His Trp Val Arg Gln Ala Pro Gly Lys Gly Leu Glu Trp Val
        35                  40                  45

Ala Arg Ile Arg Ser Lys Ser Asn Asn Tyr Thr Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Cys Gly Ser Trp Phe Ala Tyr Trp Gly Gln Gly Thr Leu
            100                 105                 110

Val Thr Val Ser Ala
        115
```

-continued

```
<210> SEQ ID NO 40
<211> LENGTH: 113
<212> TYPE: PRT
<213> ORGANISM: artificial
<220> FEATURE:
<223> OTHER INFORMATION: VL IV/18

<400> SEQUENCE: 40

Asp Ile Val Met Thr Gln Ser Pro Ser Ser Leu Ala Met Ser Leu Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Phe Gln Gln Lys Pro Gly Gln
        35                  40                  45

Ser Pro Lys Leu Leu Val Tyr Phe Thr Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys

<210> SEQ ID NO 41
<211> LENGTH: 131
<212> TYPE: PRT
<213> ORGANISM: artificial
<220> FEATURE:
<223> OTHER INFORMATION: AGP01622

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Ala His Ile Arg Asn Gln Thr His Ser Tyr Arg Thr Asp Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Ile Glu Asp Thr Ala Val Tyr
                85                  90                  95

Tyr Cys Thr Ser Pro Gly Ile Thr Gly Ser Pro Gly Thr Ala Gly Ile
            100                 105                 110

Ser Glu Tyr Tyr Asp Met Asp Val Trp Gly Gln Gly Thr Thr Val Thr
        115                 120                 125

Val Ser Ser
    130

<210> SEQ ID NO 42
<211> LENGTH: 121
<212> TYPE: PRT
<213> ORGANISM: artificial
<220> FEATURE:
<223> OTHER INFORMATION: AEX29728
```

<400> SEQUENCE: 42

Glu Val Arg Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Leu
        35                  40                  45

Gly Arg Ile Arg Lys Lys Leu Asn Ser Tyr Thr Thr Gln Tyr Ala Thr
    50                  55                  60

Ser Val Gln Gly Arg Phe Thr Ile Ser Arg Asp Asp Ser Thr Asn Ser
65                  70                  75                  80

Leu Tyr Leu Gln Met Asn Ser Leu Lys Thr Glu Asp Thr Ala Ile Tyr
                85                  90                  95

Tyr Cys Ala Arg Val Ser Asp Gly Thr Trp His Leu Asp Tyr Trp Gly
            100                 105                 110

Gln Gly Thr Leu Val Thr Val Ser Ser
        115                 120

<210> SEQ ID NO 43
<211> LENGTH: 124
<212> TYPE: PRT
<213> ORGANISM: artificial
<220> FEATURE:
<223> OTHER INFORMATION: CAA85550

<400> SEQUENCE: 43

Gln Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Thr Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Tyr Ser Ser Thr Val Thr Thr Pro Pro Phe Asp
            100                 105                 110

Tyr Trp Gly Gln Gly Thr Leu Val Thr Val Ser Ser
        115                 120

<210> SEQ ID NO 44
<211> LENGTH: 124
<212> TYPE: PRT
<213> ORGANISM: artificial
<220> FEATURE:
<223> OTHER INFORMATION: AMK70325

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Glu Met Asn Trp Val Arg Gln Ala Pro Gly Arg Gly Leu Glu Trp Val
        35                  40                  45

-continued

```
Ala Tyr Ile Ser Gly Asn Tyr Asn Asn Ile Tyr Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Thr His Tyr Asp Ile Phe Tyr Tyr Tyr Met Asp
                100                 105                 110

Val Trp Gly Lys Gly Thr Thr Val Thr Val Ser Ser
        115                 120
```

<210> SEQ ID NO 45
<211> LENGTH: 116
<212> TYPE: PRT
<213> ORGANISM: artificial
<220> FEATURE:
<223> OTHER INFORMATION: IGHV3-72

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
                20                  25                  30

Tyr Met Asp Trp Val Arg Gln Ala Pro Gly Lys Gly Leu Glu Trp Val
            35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Ala Phe Asp Val Trp Gly Gln Gly Thr Met Val
            100                 105                 110

Thr Val Ser Ser
        115
```

<210> SEQ ID NO 46
<211> LENGTH: 107
<212> TYPE: PRT
<213> ORGANISM: artificial
<220> FEATURE:
<223> OTHER INFORMATION: APZ85307

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Ser Arg Tyr
                20                  25                  30

Leu Asn Trp Tyr Gln Gln Lys Pro Gly Lys Ala Pro Asn Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105
```

-continued

<210> SEQ ID NO 47
<211> LENGTH: 107
<212> TYPE: PRT
<213> ORGANISM: artificial
<220> FEATURE:
<223> OTHER INFORMATION: AIT38562

<400> SEQUENCE: 47

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Asn Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Gly Ser Leu Gln Pro
65                  70                  75                  80

Asp Asp Phe Val Thr Tyr Tyr Cys Gln Gln Tyr Asn Ser Phe Pro Tyr
                85                  90                  95

Thr Phe Gly Gln Gly Thr Lys Val Glu Ile Lys
            100                 105

<210> SEQ ID NO 48
<211> LENGTH: 107
<212> TYPE: PRT
<213> ORGANISM: artificial
<220> FEATURE:
<223> OTHER INFORMATION: BAH04867

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 49
<211> LENGTH: 107
<212> TYPE: PRT
<213> ORGANISM: artificial
<220> FEATURE:
<223> OTHER INFORMATION: ANV21939

<400> SEQUENCE: 49

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Ser Ile Asn Asn Tyr
            20                  25                  30

```
Leu Asn Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Gly Phe Thr Leu Thr Ile Arg Ser Leu Gln Pro
65                  70                  75                  80

Glu Asp Tyr Ala Thr Tyr Tyr Cys Gln Gln Ser Tyr Arg Thr Pro Tyr
                85                  90                  95

Ser Phe Gly Gln Gly Thr Lys Leu Glu Ile Lys
            100                 105
```

```
<210> SEQ ID NO 50
<211> LENGTH: 107
<212> TYPE: PRT
<213> ORGANISM: artificial
<220> FEATURE:
<223> OTHER INFORMATION: IGKV1-33

<400> SEQUENCE: 50
```

```
Asp Ile Gln Met Thr Gln Ser Pro Ser Ser Leu Ser Ala Ser Val Gly
1                   5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Cys
                85                  90                  95

Thr Phe Gly Gln Gly Thr Lys Leu Glu Ile Lys
            100                 105
```

```
<210> SEQ ID NO 51
<211> LENGTH: 120
<212> TYPE: PRT
<213> ORGANISM: artificial
<220> FEATURE:
<223> OTHER INFORMATION: AGP01286

<400> SEQUENCE: 51
```

```
Glu Val Gln Leu Val Glu Ser Gly Gly Gly Leu Val Gln Pro Gly Gly
1                   5                   10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Leu Val Gly Ala Ile Pro Phe Asp Tyr Trp Gly Gln
            100                 105                 110

Gly Thr Leu Val Thr Val Ser Ser
        115                 120
```

<210> SEQ ID NO 52
<211> LENGTH: 119
<212> TYPE: PRT
<213> ORGANISM: artificial
<220> FEATURE:
<223> OTHER INFORMATION: AEX29087

<400> SEQUENCE: 52

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asn Phe Ser Gly Pro
                20                  25                  30

Ala Ile His Trp Val Arg Gln Ala Ser Gly Lys Gly Leu Glu Trp Val
            35                  40                  45

Gly Arg Ile Arg Ser Lys Ala Lys Asn Phe Ala Thr Ala Tyr Ala Ala
        50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Thr Thr Thr Ser Ser Ser Ile Asn Asp Tyr Trp Gly Gln Gly
                100                 105                 110

Thr Leu Val Thr Val Ser Ser
        115

<210> SEQ ID NO 53
<211> LENGTH: 117
<212> TYPE: PRT
<213> ORGANISM: artificial
<220> FEATURE:
<223> OTHER INFORMATION: ACS95862

<400> SEQUENCE: 53

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Ser Ser Tyr
                20                  25                  30

Gly Met His Trp Val Arg Gln Ala Pro Gly Arg Gly Leu Glu Trp Val
        35                  40                  45

Ala Phe Ile Arg Ser Asp Gly Ser Asn Thr Tyr Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Phe Gly Gly Asp Tyr Tyr Phe Gly Tyr Trp Gly Gln Gly Thr Leu
                100                 105                 110

Val Thr Val Ser Ser
        115

<210> SEQ ID NO 54
<211> LENGTH: 115
<212> TYPE: PRT
<213> ORGANISM: artificial
<220> FEATURE:
<223> OTHER INFORMATION: BAC01516

<400> SEQUENCE: 54

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Thr Gly Asp Tyr Trp Gly Gln Gly Thr Leu Val Thr
            100                 105                 110

Val Ser Ser
        115
```

```
<210> SEQ ID NO 55
<211> LENGTH: 117
<212> TYPE: PRT
<213> ORGANISM: artificial
<220> FEATURE:
<223> OTHER INFORMATION: IGHV3-73

<400> SEQUENCE: 55
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Tyr Tyr Gly Met Asp Val Trp Gly Gln Gly Thr Thr
            100                 105                 110

Val Thr Val Ser Ser
        115
```

```
<210> SEQ ID NO 56
<211> LENGTH: 113
<212> TYPE: PRT
<213> ORGANISM: artificial
<220> FEATURE:
<223> OTHER INFORMATION: AAW69164

<400> SEQUENCE: 56
```

```
Asp Val Val Met Thr Gln Ser Pro Asp Ser Leu Ala Val Ser Leu Gly
1               5                   10                  15

Glu Arg Val Thr Ile Asn Cys Lys Ser Ser Gln Ser Val Leu Asn Thr
            20                  25                  30

Ser Asn Asn Lys Asn Tyr Leu Val Trp Tyr Gln Gln Lys Pro Gly Gln
        35                  40                  45

Ser Pro Lys Leu Leu Ile Tyr Leu Ala Ser Thr Arg Glu Phe Gly Val
    50                  55                  60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                    85                  90                  95

Tyr His Ser Ser Pro His Thr Phe Gly Gln Gly Thr Lys Leu Glu Ile
                100                 105                 110

Lys
```

<210> SEQ ID NO 57
<211> LENGTH: 113
<212> TYPE: PRT
<213> ORGANISM: artificial
<220> FEATURE:
<223> OTHER INFORMATION: CAI99839

<400> SEQUENCE: 57

```
Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Val Leu Tyr Asn
                    20                  25                  30

Ser Asn Asn Lys Asn Tyr Leu Ala Trp Phe Gln Gln Lys Pro Gly Gln
            35                  40                  45

Pro Pro Asn Leu Val Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Phe Cys Leu Gln
                    85                  90                  95

Tyr Tyr Ser Thr Pro Leu Thr Phe Gly Gln Gly Thr Gln Val Glu Ile
                100                 105                 110

Lys
```

<210> SEQ ID NO 58
<211> LENGTH: 113
<212> TYPE: PRT
<213> ORGANISM: artificial
<220> FEATURE:
<223> OTHER INFORMATION: AMK70392

<400> SEQUENCE: 58

```
Asp Ile Gln Met Thr Gln Ser Pro Asp Ser Leu Ala Val Ser Leu Gly
1                   5                   10                  15

Glu Arg Ala Thr Ile Asn Cys Lys Ala Ser Gln Ser Val Leu Tyr Ser
                    20                  25                  30

Ser Lys Asn Lys Asn Tyr Leu Ala Trp Tyr Gln Gln Lys Pro Gly Gln
            35                  40                  45

Pro Pro Lys Leu Leu Ile Tyr Arg Ala Ser Thr Arg Asp Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                    85                  90                  95

Tyr Tyr Ser Thr Pro Gln Thr Phe Gly Gln Gly Thr Lys Val Glu Ile
                100                 105                 110

Lys
```

```
<210> SEQ ID NO 59
<211> LENGTH: 113
<212> TYPE: PRT
<213> ORGANISM: artificial
<220> FEATURE:
<223> OTHER INFORMATION: ALV87854

<400> SEQUENCE: 59

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Lys Asn Lys Asn Tyr Leu Ala Trp Phe Gln Gln Lys Pro Gly Gln
        35                  40                  45

Pro Pro Lys Val Leu Ile Tyr Ser Thr Ser Thr Arg Ala Ser Gly Val
        50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Leu Gln
                85                  90                  95

Tyr Tyr Ile Thr Pro Tyr Thr Phe Gly Gln Gly Thr Lys Leu Glu Ile
            100                 105                 110

Lys

<210> SEQ ID NO 60
<211> LENGTH: 113
<212> TYPE: PRT
<213> ORGANISM: artificial
<220> FEATURE:
<223> OTHER INFORMATION: IGKV4-1

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 61
<211> LENGTH: 23
<212> TYPE: DNA
<213> ORGANISM: artificial
<220> FEATURE:
<223> OTHER INFORMATION: CD47 sense primer

<400> SEQUENCE: 61
agaaggtgaa acgatcatcg agc                                            23

<210> SEQ ID NO 62
```

```
<211> LENGTH: 21
<212> TYPE: DNA
<213> ORGANISM: artificial
<220> FEATURE:
<223> OTHER INFORMATION: CD47 antisense primer

<400> SEQUENCE: 62
ctcatccata ccaccggatc t                                                          21

<210> SEQ ID NO 63
<211> LENGTH: 21
<212> TYPE: DNA
<213> ORGANISM: artificial
<220> FEATURE:
<223> OTHER INFORMATION: PD-L1 sense primer

<400> SEQUENCE: 63
tggcatttgc tgaacgcatt t                                                          21

<210> SEQ ID NO 64
<211> LENGTH: 21
<212> TYPE: DNA
<213> ORGANISM: artificial
<220> FEATURE:
<223> OTHER INFORMATION: PD-L1 antisense primer

<400> SEQUENCE: 64
agtgcagcca ggtctaattg t                                                          21

<210> SEQ ID NO 65
<211> LENGTH: 20
<212> TYPE: DNA
<213> ORGANISM: artificial
<220> FEATURE:
<223> OTHER INFORMATION: beta-actin sense primer

<400> SEQUENCE: 65
ccaaccgcga gaagatgacc                                                            20

<210> SEQ ID NO 66
<211> LENGTH: 21
<212> TYPE: DNA
<213> ORGANISM: artificial
<220> FEATURE:
<223> OTHER INFORMATION: beta-actin antisense primer

<400> SEQUENCE: 66
gatcttcatg aggtagtcag t                                                          21
```

HUMANIZED ANTI-CA IX ANTIBODIES AND METHODS OF THEIR USE

FIELD OF THE INVENTION

The present invention relates to humanized antibodies capable of specific binding to human carbonic anhydrase IX. More specifically, the present invention relates to antibodies against CA IX, comprising murine-derived complementarity determining regions and humanized heavy and light regions.

BACKGROUND OF THE INVENTION

CA IX is a cancer-related carbonic anhydrase identified by Zavada, Pastorekova, Pastorek (U.S. Pat. No. 5,387,676) using the M75 monoclonal antibody first described by Pastorekova et al, Virology, 187:620e626, 1992. That antibody was employed in cloning of cDNA and gene encoding CA IX, in assessment of CA IX expression in tumors and normal tissues, in study of CA IX regulation and in studies of CA IX relationship to cancer progression and therapy resistance. All these studies supported the assumption made in the original U.S. Pat. No. 5,387,676 that CA IX can be used diagnostically and/or prognostically as a preneoplastic/neoplastic tumor marker and therapeutically as a target, and showed that the M75 monoclonal antibody is a valuable CA IX-specific reagent useful for different immunodetection methods and immunotargeting approaches.

CA IX (alternative name: MN protein) belongs to the carbonic anhydrase family of zinc metalloenzymes that catalyze the reversible hydration of carbon dioxide to bicarbonate ions and protons. There are 15 human CA isoforms out of which three are inactive and the other twelve range in activity from weak to very strong. Most of the isoenzymes are predominantly expressed in differentiated cells to fulfill specialized physiological roles in various tissues and organs (Pastorekova et al, *J Enzyme Inhib Med Chem* 19, 199-229, 2004). CA IX has a unique position due to its strong association with cancer, hypoxia-related expression pattern, acidic pKa optimum and an extra proteoglycan-like domain (PG) protruding from the globular catalytic domain of the enzyme. CA IX enzyme active site in the catalytic domain (CA) is facing the extracellular space and contributes to pH regulation across the plasma membrane. It is now well established that CA IX cooperates with diverse acid extruders and bicarbonate importers including sodium-dependent bicarbonate transporters NBCe 1 and NBCn1 and lactate and protons-exporting monocarboxylate transporters MCT1 and MCT4. Involvement of CA IX in pH regulation has multiple consequences supporting tumor phenotype. CA IX also behaves as an adhesion molecule that contributes to the assembly and maturation of focal adhesion contacts during cell attachment and spreading on solid support. On the contrary, CA IX can destabilize intercellular adhesion contacts by disconnection of E-cadherin from the cytoskeletal anchorage through the competitive binding to beta catenin. Accumulating experimental evidence suggests that CA IX is functionally involved in diverse aspects of cancer development, including protection of cancer cell survival in conditions of hypoxia and acidosis, facilitation of cancer cell migration/invasion, contribution to metastatic dissemination, homing and growth of metastatic lesions.

CA IX is one of the best responders to low oxygenation (ranging from anoxia to moderate hypoxia), mainly because of its transcriptional regulation by hypoxia-inducible factor HIF-1 binding to hypoxia-response element (HRE) consensus sequence localized near the transcription initiation site (Wykoff et al, *Cancer Res* 60, 7075-7083, 2000). Inactivation of the pVHL (von Hippel-Lindau) tumor suppressor protein, which causes HIF degradation, results in the elevation of CA IX expression in kidney tumors (Ivanov et al, *Proc Natl Acad Sci USA* 95, 12596-12601, 1998). Moreover, hypoxia regulates splicing of the CA IX mRNA and a protein kinase A (PKA)-mediated phosphorylation of the cytoplasmic tail of the CA IX protein, in both cases affecting its enzyme activity (Barathova et al, *Br J Cancer* 98, 129-136, 2008; Ditte et al, *Cancer Res* 71, 7558-7567, 2011).

CA IX can internalize from the cell surface to the cell cytoplasm via endocytosis induced by hypoxia and calcium depletion as well as by specific antibodies binding to its extracellular part (Zatovicova et al, *Curr Pharm Des* 16, 3255-3263, 2010). Ectodomain of CA IX can be cleaved by metalloproteinase ADAM17 and released to the microenvironment in response to hypoxia, acidosis and toxic insults of carbonic anhydrase inhibitors or chemotherapeutic drugs (Zatovicova et al, *Br J Cancer* 93, 1267-1276, 2005; Vidlickova et al, *BMC Cancer* 16, 239, 2016).

CA IX expression in non-cancerous tissues is rare and generally confined to epithelia of the stomach, gallbladder, pancreas and intestine.

There are more than 1000 studies of CA IX clinical value suggesting that it can serve as a biomarker and/or therapy target in diverse tumor types and settings (Pastorek and Pastorekova, *Seminars in Cancer Biology* 31, 52-64, 2015).

CA IX is expressed in high percentage of cells in more than 90% of clear cell renal cell carcinoma (ccRCC) that carry an inactivating mutation/deletion of the VHL tumor suppressor gene. In many other tumor types, CA IX is expressed regionally in areas that are hypoxic and/or acidic and usually increases with increasing tumor stage and grade. CA IX can be also detected in body fluids of cancer patients that can be clinically exploited for non-invasive screening or monitoring of cancer patients.

Meta-analysis of studies encompassing more than 24 thousands of patients with non-RCC tumors revealed strongly significant associations between CA IX expression evaluated by immunohistochemistry and all endpoints: overall survival, disease-free, locoregional control, disease-specific, metastasis-free survival, and progression-free survival (van Kuijk et al, *Front Oncol* 6, 69, 2016). Subgroup analyses showed similar associations in the majority of tumor sites and types. In conclusion, these results show that patients having tumors with high CA IX expression have higher risk of disease progression, and development of metastases, independent of tumor type or site. In addition, there are numerous studies showing correlation between CA IX positivity and resistance to chemotherapy, radiotherapy and even immunotherapies directed to other cancer-related molecular targets, such as HER-2 (human epidermal growth factor receptor 2), VEGF (vascular endothelial growth factor), and PD-1 (programmed cell death protein 1). These findings support the usefulness of clinical tests determining patient's prognosis and therapy outcome based on CA IX expression and provide a rationale for the development of new CA IX-targeted treatment strategies.

CA IX-targeting strategy based on immunotherapy exploits the tumor-related expression pattern of CA IX. This approach uses monoclonal antibodies (mAbs) and thus, ensures high specificity and selectivity toward CA IX that is currently not achievable with chemical compounds. In case of antibody-dependent cell-mediated cytotoxicity (ADCC) as the main mechanism of action, the killing effects is fast and does not support development of compensatory mechanisms. Previous clinical trials with the CA IX-specific monoclonal antibodies did not meet the primary endpoint due to lack of patients' stratification (ADCC response-inducing GcG250, Wilex), or due to inacceptable toxicity (antibody-drug conjugate MMAE-BAY79-4620, Bayer). Thus, the preferred strategy of immunotherapy includes ADCC and stratification of patients based on the CA IX expression level.

Specificity is an important factor in decisions concerning whether a particular mAb can be successfully used for cancer therapy. This attribute is accomplished by unique tumor-related expression pattern of CA IX and on the other hand, only limited expression in few normal tissues. Previous clinical evidence from ccRCC studies suggests that the antibody-based immunotherapy targeted to CA IX is safe and well tolerated (Chamie et al, JAMA Oncology 3:913-920, 2017). Additionally, safety of the treatment is linked to the evidence from multiple studies that CA IX expression is strongly linked to tumor phenotype and confined to only few non-cancerous tissues where the basal membrane does not allow the intravenously administered antibodies to reach epithelial cells. Data from the literature on CA IX-specific chimeric antibody cG250 (having the variable regions of murine G250 and constant regions derived from human IgG, also known as RENCAREX® or GIRENTUXIMAB®) showed no grade III and IV as well as dose-limiting toxicity and, on the other hand, an excellent accumulation in RCC and increased median/overall survival rates (Steffens et al, *J Chn Oncol* 15:1529-1537, 1997; Davis et al, *Cancer Immunity* 7:14-23 2007; Bleumer et al, *Br J Cancer* 90:985-990, 2004). Moreover, the combination therapy of cG250 with low dose interferon alpha was safe, well tolerated and with clinical benefits for patients with progressive metastatic RCC (Siebels et al, *World J Urol* 29:121-126, 2011). WO2003/100029 discloses CA IX-specific murine monoclonal antibodies generated in CA IX-deficient mice with targeted disruption of Car9 gene. The set of antibodies, produced by specific hybridoma cells, includes VII/20 mAb and IV/18 mAb (as described in Zatovicova et al, *J Immunol Methods* 282, 117-134, 2003). The mAbs are highly selective to CA IX and do not cross-react with the human CA I, CA II and CA XII proteins that are expressed mostly in normal differentiated tissues. Thus, both monoclonal antibodies are expected to have strictly tumor-specific effect.

The antibody VII/20 binds to the conformational epitope in the catalytic (CA) domain of CA IX, induces internalization of CA IX and shows potent anti-tumor effect in vivo in mouse model with subcutaneous tumor xenografts (Zatovicova et al, *Curr Pharm Des* 16, 3255-3263, 2010). The antibody IV/18 binds to the linear epitope in the proteoglycan-like (PG) domain of CA IX and does not induce internalization. The ability of these two mAbs to distinguish antigenic regions on two separate extracellular domains of CA IX offers an opportunity for effective targeting. The fact that both VII/20 and IV/18 monoclonal antibodies were generated in CA IX-deficient mice which are no longer available and thus, could not be prepared again only emphasize their uniqueness. All previously mentioned attributes of the monoclonal antibodies provide a rationale for their humanization with intent of their use in anticancer immunotherapy.

There is a need in the art for safe and effective antibodies that target CA IX for the treatment of CA IX-associated conditions, such as cancer. The invention fulfills that need and provides other benefits.

SUMMARY OF THE INVENTION

The present invention provides a humanized antibody specifically recognizing human CA IX, comprising:

a) a heavy chain variable region sequence comprising CDR sequences identical to or differing in 1 or 2 amino acids from the following sequences:
GFTFTDYYMH (SEQ ID NO. 1), and
FIRNKASGYTPQYSASVKG (SEQ ID NO. 2), and
VRGGHAGSNYWYFDV (SEQ ID NO. 3); or
a heavy chain variable region sequence comprising CDR sequences identical to or differing in 1 or 2 amino acids from the following sequences:
GFTFNTNAMH (SEQ ID NO. 17), and
RIRSKSNNYTTYYADSVKD (SEQ ID NO. 18), and
VCGSWFAY (SEQ ID NO. 19);
and
b) a light chain variable region sequence comprising the CDR sequences identical to or differing in 1 or 2 amino acids from the following sequences:
HVSQNINVWLS (SEQ ID NO. 9), and
QASNLHT (SEQ ID NO. 10), and
QQGQSYPFT (SEQ ID NO. 11); or
a light chain variable region sequence comprising the CDR sequences identical to or differing in 1 or 2 amino acids from the following sequences:
KSSQSLLNSSNQKNYLA (SEQ ID NO. 25), and
FTSTRQS (SEQ ID NO. 26), and
QQHYSIPLT (SEQ ID NO. 27).

In some embodiments, the humanized antibody of the present invention contains a heavy chain variable region sequence comprising CDR sequences identical to or differing in 1 or 2 amino acids from the sequences GFTFTDYYMH (SEQ ID NO. 1), and FIRNKASGYTPQYSASVKG (SEQ ID NO. 2), and VRGGHAGSNYWYFDV (SEQ ID NO. 3); and a light chain variable region sequence comprising the CDR sequences identical to or differing in 1 or 2 amino acids from the following sequences: HVSQNINVWLS (SEQ ID NO. 9), and QASNLHT (SEQ ID NO. 10), and QQGQSYPFT (SEQ ID NO. 11).

In some embodiments, the humanized antibody of the present invention contains a heavy chain variable region sequence comprising CDR sequences identical to or differing in 1 or 2 amino acids from the sequences GFTFNTNAMH (SEQ ID NO. 17), and RIRSKSNNYTTYYADSVKD (SEQ ID NO. 18), and VCGSWFAY (SEQ ID NO. 19); and a light chain variable region sequence comprising the CDR sequences identical to or differing in 1 or 2 amino acids from the following sequences: KSSQSLLNSSNQKNYLA (SEQ ID NO. 25), and FTSTRQS (SEQ ID NO. 26), and QQHYSIPLT (SEQ ID NO. 27).

In one aspect, the humanized antibody specifically recognizing human CA IX according to the invention comprises at least one variable region selected from the group consisting of:
a heavy chain variable region comprising or having the sequence:

(SEQ ID NO. 33)

X$^1$VX$^2$LVX$^3$SGGGLVQPGX$^4$SLRLSCX$^5$ASGFTFTDYYMHWVRQAPGX$^6$GL

EWX$^7$X$^8$FIRNKASGYTPQYSASVKGRFTISRDX$^9$X$^{10}$X$^{11}$X$^{12}$X$^{13}$X$^{14}$YLQM

NSLX$^{15}$X$^{16}$EDTAX$^{17}$YYVRGGHAGSNYWYFDVWGX$^{18}$GTX$^{19}$VTVSS wherein
X$^1$=E or Q
X$^2$=Q or R
X$^3$=E or Q
X$^4$=G or R $X^5$=A or T
$X^6$=K or R
$X^7$=V or L
$X^8$=A or G
$X^9$=D or N
$X^{10}$=S or A
$X^{11}$=K or T or E
$X^{12}$=N or T
$X^{13}$=S or I
$X^{14}$=L or A
$X^{15}$=K or R
$X^{16}$=Y or A or I
$X^{17}$=V or I
$X^{18}$=Q or K
$X^{19}$=T or L or M; and a light chain variable region comprising or having the sequence:

(SEQ ID NO. 34)
DIQMTQSPSX$^{20}$LSASVGDRVTIX$^{21}$C<u>HVSQNINVWL</u>SWYQQKPGX$^{22}$AP

X$^{23}$LLIY<u>QASNLHT</u>GVPSRFSGSGSGTX$^{24}$FTX$^{25}$TIX$^{26}$SLQPX$^{27}$DX$^{28}$X$^{29}$

TYYC<u>QQGQSYPFT</u>FGX$^{30}$GTKX$^{31}$EIK wherein
$X^{20}$=S or T
$X^{21}$=T or N
$X^{22}$=K or N or E
$X^{23}$=N or K
$X^{24}$=H or E or D or G
$X^{25}$=L or F
$X^{26}$=S or G or R
$X^{27}$=E or D
$X^{28}$=I or F or Y
$X^{29}$=A or V
$X^{30}$=Q or G
$X^{31}$=V or L; and a heavy chain variable region comprising or having the sequence:

(SEQ ID NO. 35)
X$^{32}$VQLVESGGGX$^{33}$VQPGX$^{34}$SLX$^{35}$LSCAAS<u>GFTFNTNAMH</u>WVRQAX$^{36}$GX$^{37}$

GLEWVX$^{38}$<u>RIRSKSNNYTTYYADSVKD</u>RFTISRDX$^{39}$SKX$^{40}$TX$^{41}$YLQX$^{42}$NSL

X$^{43}$X$^{44}$EDTAVYYC<u>VCGSWFAY</u>WGQGTX$^{45}$VTVSS wherein
$X^{32}$=E or Q
$X^{33}$=L or V
$X^{34}$=G or R
$X^{35}$=K or R
$X^{36}$=S or P
$X^{37}$=K or R
$X^{38}$=A or G
$X^{39}$=D or N
$X^{40}$=N or S
$X^{41}$=A or L
$X^{42}$=M or V
$X^{43}$=K or R
$X^{44}$=T or A
$X^{45}$=L or T; and a light chain variable region comprising or having the sequence:

(SEQ ID NO. 36)
DX$^{46}$X$^{47}$MTQSPDSLAVSLGERX$^{48}$TINCK<u>SSQSLLNSSNQKNYLA</u>WX$^{49}$QQKP

GQX$^{50}$PX$^{51}$X$^{52}$X$^{53}$LY<u>FTSTRQS</u>GVPDRFX$^{54}$GSGSGTDFTLTIX$^{55}$SLQAEDV

AVYX$^{56}$C<u>QQHYSIPLT</u>FGQGTX$^{57}$X$^{58}$EIK $X^{46}$=V or I
$X^{47}$=V or Q
$X^{48}$=V or A
$X^{49}$=y or F
$X^{50}$=S or P
$X^{51}$=K or N
$X^{52}$=l or V
$X^{53}$=L or V
$X^{54}$=S or T
$X^{55}$=S or N
$X^{56}$=Y or F
$X^{57}$=K or Q
$X^{58}$=L or V.

In a preferred embodiment, the heavy chain region of SEQ ID NO. 33 is combined with the light chain region of SEQ ID NO. 34. In another preferred embodiment, the heavy chain region of SEQ ID NO. 35 is combined with the light chain region of SEQ ID NO. 36.

In one preferred aspect, the invention provides the humanized antibody specifically recognizing human CA IX, comprising at least one variable region selected from the group consisting of:

a) a heavy chain variable region amino acid sequence comprising or having the sequence selected from the group consisting of (SEQ ID NO. 4)
EVQLVESGGGLVQPGGSLRLSCAAS<u>GFTFTDYYMH</u>WVRQAPGKGLEWVAF<u>I</u>

<u>RNKASGYTPQYSASVKG</u>RFTISRDDSKNSLYLQMNSLKIEDTAVYYC<u>VRGG</u>

<u>HAGSNYWYFDV</u>WGQGTTVTVSS, (SEQ ID NO. 5)
EVRLVESGGGLVQPGGSLRLSCAAS<u>GFTFTDYYMH</u>WVRQAPGKGLEWLGF<u>I</u>

<u>RNKASGYTPQYSASVKG</u>RFTISRDDSTNSLYLQMNSLKTEDTAIYYC<u>VRGG</u>

<u>HAGSNYWYFDV</u>WGQGTLVTVSS, (SEQ ID NO. 6)
QVQLVQSGGGLVQPGRSLRLSCTAS<u>GFTFTDYYMH</u>WVRQAPGKGLEWVGF<u>I</u>

<u>RNKASGYTPQYSASVKG</u>RFTISRDDSKTIAYLQMNSLKTEDTAVYYC<u>VRGG</u>

<u>HAGSNYWYFDV</u>WGQGTLVTVSS, (SEQ ID NO. 7)
EVQLVESGGGLVQPGGSLRLSCAAS<u>GFTFTDYYMH</u>WVRQAPGRGLEWVAF<u>I</u>

<u>RNKASGYTPQYSASVKG</u>RFTISRDNAENSLYLQMNSLRAEDTAVYYC<u>VRGG</u>

<u>HAGSNYWYFDV</u>WGKGTTVTVSS,
and (SEQ ID NO. 8)
EVQLVESGGGLVQPGGSLRLSCAAS<u>GFTFTDYYMH</u>WVRQAPGKGLEWVGF<u>I</u>

<u>RNKASGYTPQYSASVKG</u>RFTISRDDSKNSLYLQMNSLKTEDTAVYYC<u>VRGG</u>

<u>HAGSNYWYFDV</u>WGQGTMVTVSS;

b) a light chain variable region amino acid sequence comprising or having the sequences selected from the group consisting of (SEQ ID NO. 12)
DIQMTQSPSSLSASVGDRVTITCHVSQNINVWLSWYQQKPGKAPNLLIYQA

SNLHTGVPSRFSGSGSGTHFTLTISSLQPEDIATYYCQQGQSYPFTFGGGT

KVEIK, (SEQ ID NO. 13)
DIQMTQSPSTLSASVGDRVTITCHVSQNINVWLSWYQQKPGNAPKLLIYQA

SNLHTGVPSRFSGSGSGTEFTLTIGSLQPDDFVTYYCQQGQSYPFTFGQGT

KVEIK, (SEQ ID NO. 14)
DIQMTQSPSSLSASVGDRVTITCHVSQNINVWLSWYQQKPGEAPKLLIYQA

SNLHTGVPSRFSGSGSGTDFTLTISSLQPEDFATYYCQQGQSYPFTFGQGT

KLEIK, (SEQ ID NO. 15)
DIQMTQSPSSLSASVGDRVTINCHVSQNINVWLSWYQQKPGEAPKLLIYQA

SNLHTGVPSRFSGSGSGTGFTLTIRSLQPEDYATYYCQQGQSYPFTFGQGT

KLEIK,
and (SEQ ID NO. 16)
DIQMTQSPSSLSASVGDRVTITCHVSQNINVWLSWYQQKPGKAPKLLIYQA

SNLHTGVPSRFSGSGSGTDFTFTISSLQPEDIATYYCQQGQSYPFTFGQGT

KLEIK;

c) a heavy chain variable region amino acid sequence comprising or having the sequences selected from the group consisting of (SEQ ID NO. 20)
EVQLVESGGGLVQPGGSLKLSCAASGFTFNTNAMHWVRQASGKGLEWVGRI

RSKSNNYTTYYADSVKDRFTISRDDSKNTAYLQMNSLKTEDTAVYYCVCGS

WFAYWGQGTLVTVSS, (SEQ ID NO. 21)
EVQLVESGGGLVQPGGSLKLSCAASGFTFNTNAMHWVRQASGKGLEWVGRI

RSKSNNYTTYYADSVKDRFTISRDDSKSTAYLQMNSLKTEDTAVYYCVCGS

WFAYWGQGTLVTVSS, (SEQ ID NO. 22)
QVQLVESGGGVVQPGGSLRLSCAASGFTFNTNAMHWVRQAPGRGLEWVARI

RSKSNNYTTYYADSVKDRFTISRDNSKNTLYLQVNSLRAEDTAVYYCVCGS

WFAYWGQGTLVTVSS, (SEQ ID NO. 23)
EVQLVESGGGVVQPGRSLRLSCAASGFTFNTNAMHWVRQAPGKGLEWVARI

RSKSNNYTTYYADSVKDRFTISRDNSKNTLYLQMNSLRAEDTAVYYCVCGS

WFAYWGQGTLVTVSS,
and (SEQ ID NO. 24)
EVQLVESGGGLVQPGGSLKLSCAASGFTFNTNAMHWVRQASGKGLEWVGRI

RSKSNNYTTYYADSVKDRFTISRDDSKNTAYLQMNSLKTEDTAVYYCVCGS

WFAYWGQGTTVTVSS;
and d) a light chain variable region amino acid sequence comprising or having the sequences selected from the group consisting of (SEQ ID NO. 28)
DVVMTQSPDSLAVSLGERVTINCKSSQSLLNSSNQKNYLAWYQQKPGQSP

KLLIYFTSTRQSGVPDRFSGSGSGTDFTLTISSLQAEDVAVYYCQQHYSI

PLTFGQGTKLEIK, (SEQ ID NO. 29)
DIVMTQSPDSLAVSLGERATINCKSSQSLLNSSNQKNYLAWFQQKPGQPP

NLVIYFTSTRQSGVPDRFSGSGSGTDFTLTINSLQAEDVAVYFCQQHYSI

PLTFGQGTQVEIK, (SEQ ID NO. 30)
DIQMTQSPDSLAVSLGERATINCKSSQSLLNSSNQKNYLAWYQQKPGQPP

KLLIYFTSTRQSGVPDRFSGSGSGTDFTLTISSLQAEDVAVYFCQQHYSI

PLTFGQGTKVEIK, (SEQ ID NO. 31)
DIVMTQSPDSLAVSLGERATINCKSSQSLLNSSNQKNYLAWFQQKPGQPP

KVLIYFTSTRQSGVPDRFTGSGSGTDFTLTISSLQAEDVAVYYCQQHYSI

PLTFGQGTKLEIK,
and (SEQ ID NO. 32)
DIVMTQSPDSLAVSLGERATINCKSSQSLLNSSNQKNYLAWYQQKPGQPP

KLLIYFTSTRQSGVPDRFSGSGSGTDFTLTISSLQAEDVAVYYCQQHYSI

PLTFGQGTKLEIK.

In a preferred embodiment, the heavy chain variable regions listed in a) are combined with the light chain variable regions listed in b) in one antibody.

In another preferred embodiment, the heavy chain variable regions listed in c) are combined with the light chain variable regions listed in d) in one antibody.

Preferably, the humanized antibody of the present invention contains:

a heavy chain variable region amino acid sequence comprising or having the sequence of SEQ ID NO. 7; and a light chain variable region amino acid sequence comprising or having the sequence selected from the group consisting of SEQ ID NO. 12, SEQ ID NO. 13, SEQ ID NO. 14, SEQ ID NO. 15 and SEQ ID NO. 16;

or a heavy chain variable region amino acid sequence comprising or having the sequence selected from a group consisting of SEQ ID NO. 22 and SEQ ID NO. 23; and a light chain variable region amino acid sequence comprising or having the sequence selected from a group consisting of SEQ ID NO. 28, SEQ ID NO. 29 and SEQ ID NO. 32.

According to a particularly preferred embodiment of the invention, the antibody of the invention comprises:

a heavy chain variable region amino acid sequence comprising or having the sequence of SEQ ID NO. 7 and a light chain variable region amino acid sequence comprising or having the sequence of SEQ ID NO. 15; or a heavy chain variable region amino acid sequence comprising or having the sequence of SEQ ID NO. 23 and a light chain variable region amino acid sequence comprising or having the sequence of SEQ ID NO. 32.

Preferably, the humanized antibody of the present invention has human IgG constant regions (allotype G1m17,1) of the heavy chains and human kappa constant regions (allotype Km3) of the light chains.

The present invention further provides a pharmaceutical composition comprising the humanized antibody as described above, which specifically recognizes human CA IX, and a pharmaceutically acceptable carrier, diluent or excipient.

The present invention encompasses also the humanized antibody or the pharmaceutical composition as described above, for use in the treatment of a disease or disorder associated with expression, activation or function of a CA IX protein. Such diseases and disorders typically include cell proliferative disease or disorder, such as a cancer selected from the group consisting of: squamous cell carcinoma, myeloma, small-cell lung cancer, non-small cell lung cancer, glioma, Hodgkin's lymphoma, non-Hodgkin's lymphoma, acute myeloid leukemia, multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, mesothelioma, and head and neck cancer.

Preferably, the present invention provides the humanized antibody or the pharmaceutical composition as described above for use in the treatment of breast cancer, mesothelioma, or glioblastoma expressing CA IX.

In the medical use of the humanized antibodies of pharmaceutical compositions, more than one humanized antibody can be used. The humanized antibodies or pharmaceutical compositions comprising the humanized antibodies may be administered simultaneously or sequentially. Preferably, they are administered sequentially.

The present invention further provides a method of treating a disease or disorder associated with expression, activation or function of a CA IX protein, comprising administering to a subject in need thereof a therapeutically effective amount of the humanized antibody or of the pharmaceutical composition as described above. Such diseases or disorders typically include cell proliferative diseases or disorders, such as a cancer selected from the group consisting of: squamous cell carcinoma, myeloma, small-cell lung cancer, non-small cell lung cancer, glioma, Hodgkin's lymphoma, non-Hodgkin's lymphoma, acute myeloid leukemia, multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, mesothelioma, and head and neck cancer.

Preferably, the present invention provides a method of treating of breast cancer, mesothelioma, or glioblastoma expressing CA IX, comprising administering to a subject in need thereof a therapeutically effective amount of the humanized antibody or the pharmaceutical composition as described above.

Yet furthermore, the present invention provides a method of reducing or inhibiting invasiveness of a tumor of a subject, comprising administering to a subject in need thereof a therapeutically effective amount of the humanized antibody or the pharmaceutical composition as described above, thereby reducing or inhibiting invasiveness of a tumor in the subject.

The appropriate daily or weekly dose of the humanized antibody to CA IX for administration to a patient is preferably ranging from 0.001 mg/kg to 15 mg/kg body weight.

The humanized antibody to CA IX may be administered in a number of possible regimens. Typically, the following regimens may be suitable:
    i) multiple, identical or different doses of the humanized antibody;
    ii) multiple escalating doses of the humanized antibody; or
    iii) administering a dose of the humanized antibody once every week, once every 2 weeks, once every 3 weeks, once every 4 weeks, or once every 5 weeks.

In some embodiments, the administration of the humanized antibody to CA IX or the pharmaceutical composition as described above comprises 1-10 administration cycles, each cycle comprising 2-5 infusions/doses every 1-4 weeks, with a humanized antibody, followed by a break of 1-8 weeks between each two cycles.

The present invention further provides a diagnostic composition comprising at least one humanized antibody as described herein above, and at least one carrier, diluent, or excipient.

Suitable diagnostic assays in which the antibody of the present invention include immunoassays, such as ELISA, affinity chromatography, immunohistochemistry and Western blotting.

The present invention thus provides a method for diagnosing a cancer in a subject in need thereof, the method comprising contacting a biological sample derived or obtained from said subject with the diagnostic composition as described herein, wherein a complex formation beyond a predetermined threshold is indicative of the cancer in said subject.

In the diagnostic composition or in the method for diagnosing a cancer in a subject the humanized antibody may be linked, bound or conjugated to a paramagnetic, radioactive or fluorogenic moiety that is detectable upon imaging.

BRIEF DESCRIPTION OF FIGURES

FIG. 1A: Total radiant efficiency reflects the amount of HT1080-RFP cancer cells in murine lungs from either control or IV/18 mAb-treated group. FIG. 1B: Representative ex vivo images of fluorescent lung metastases of control mice and of mice treated with IV/18 mAb.

FIG. 3: Screening of 25 humanized variants of CA9hu-1 and CA9hu-2 in antibody-dependent cell-mediated cytotoxicity using either CA IX-positive (C-33a_CA IX) or CA IX-negative (C-33a_neo) cells. Chimeric HC0LC0 (having the murine variable domains and the human Ig constant domains) antibodies were used as reference samples. Data in the graph are expressed as luminescence in relative luminescence units (RLU) and represent mean±standard deviation values.

Figure 4:
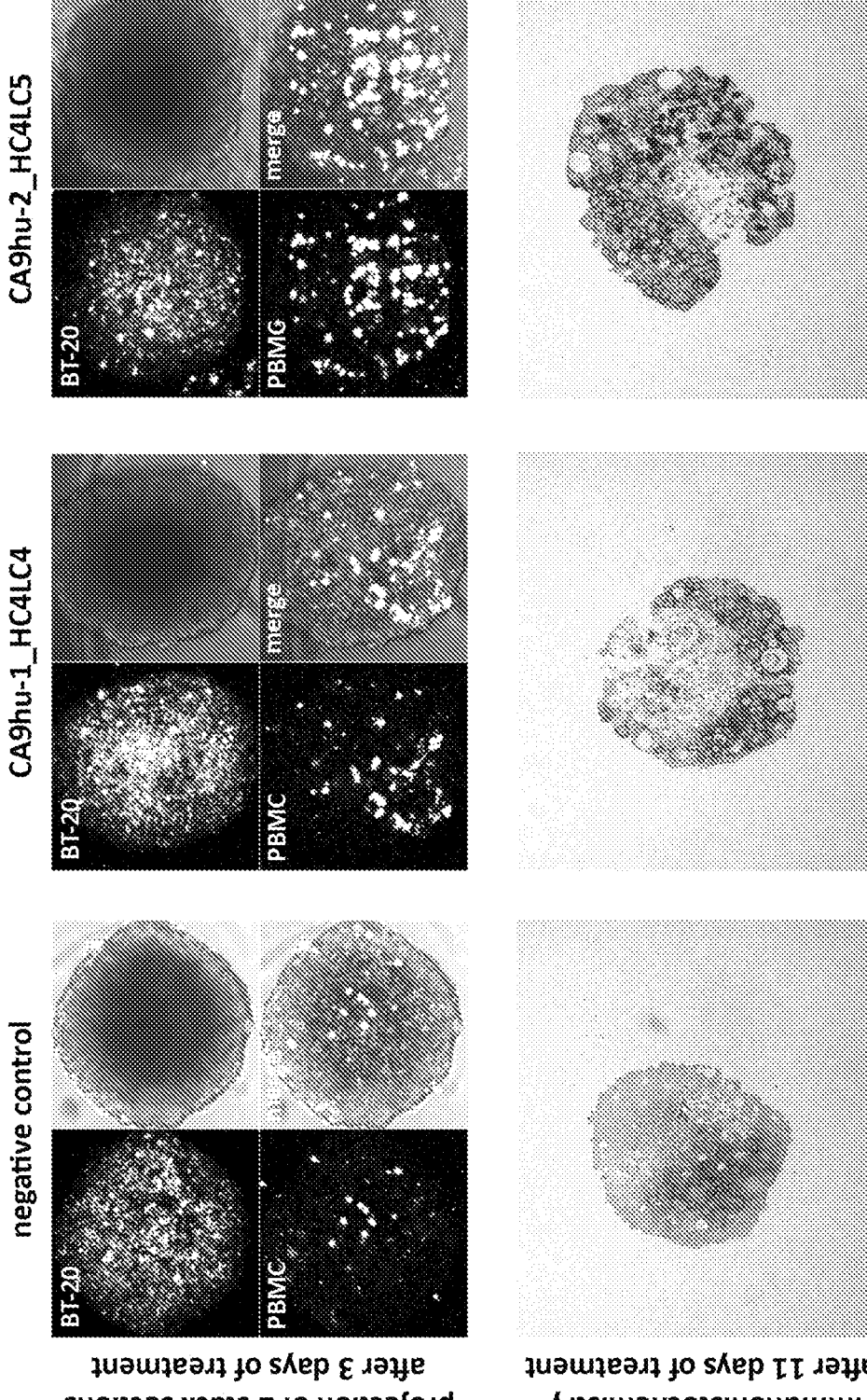

FIG. 4: 3D model of BT-20 spheroids cultivated with human PBMCs in the presence of humanized antibody variants CA9hu-1_HC4LC4 and CA9hu-2_HC4LC5. Projection of PBMC cells within BT-20 spheroids (both pre-stained using CellBrite Dye) from Z-stack sections after 3 days of treatment acquired across the spheroid volume (upper part of the figure). Immunohistochemical analysis of the impact of humanized antibody variants CA9hu-1_HC4LC4 and CA9hu-2_HC4LC5 on spheroid morphology. Representative sections from BT-20 spheroids co-cultivated with PBMCs and treated with humanized antibody variants for 11 days. A distinctive pattern of CA IX-staining was observed within the membranes across the BT-20 spheroids (lower part of the figure).

Figure 5:
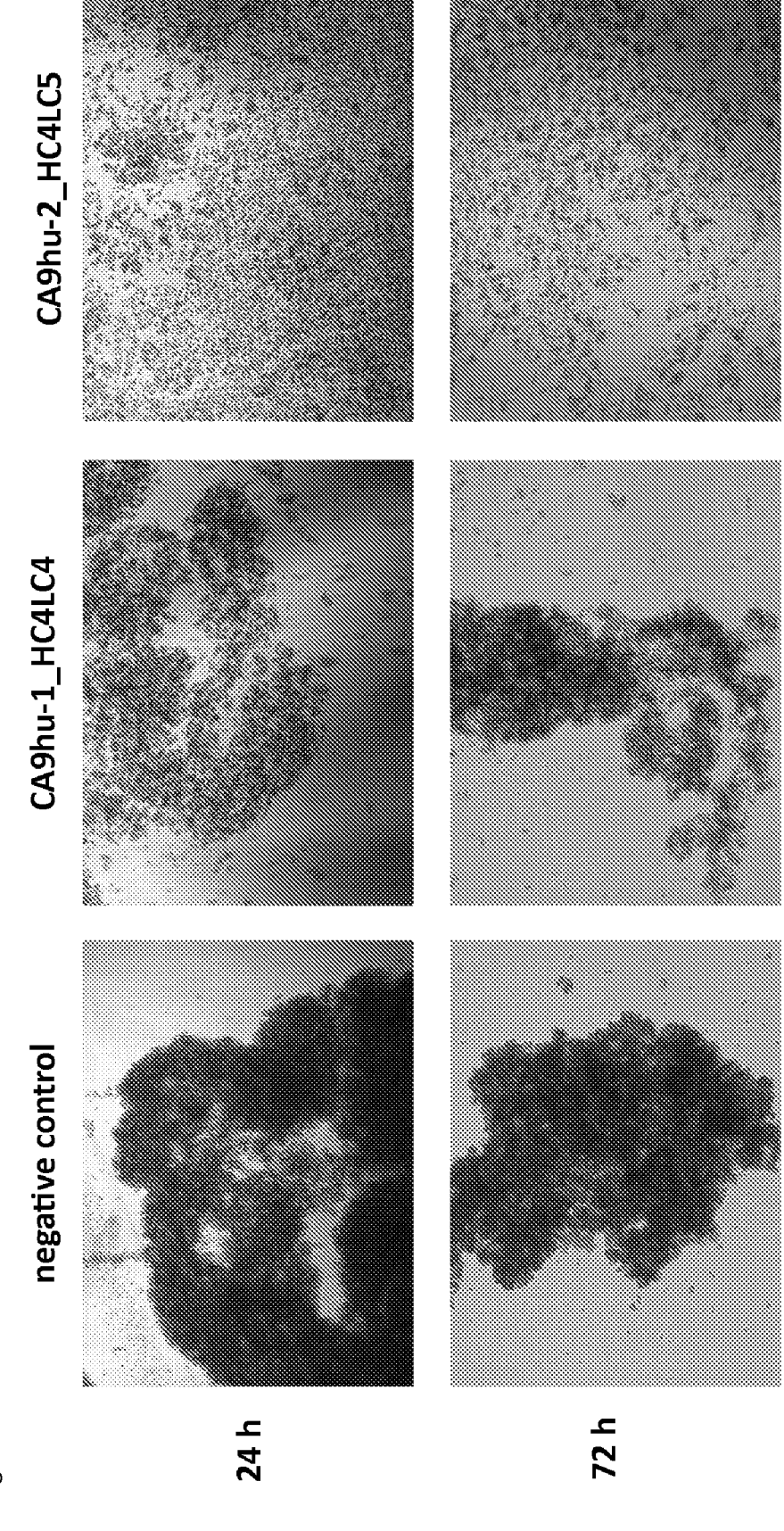

FIG. 5: Analysis of multicellular aggregation of C-33a_CA IX with selected humanized antibodies (CA9hu-1_HC4LC4 and CA9hu-2_HC4LC5) after 24 h and 72 h on poly-HEMA coated dishes. C-33a_CA IX cells incubated in the absence of humanized antibodies are marked as "negative control".

Figure 6:
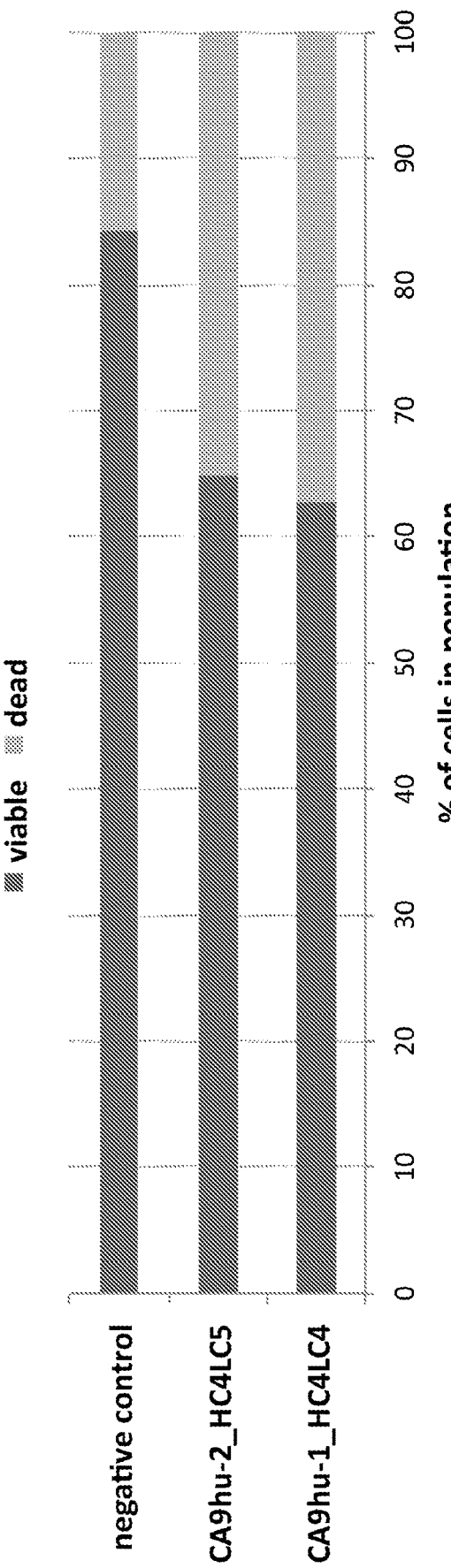

FIG. 6: Analysis of C-33a_CA IX cells by propidium iodide staining and flow cytometry after 72 h of treatment with selected humanized antibodies (CA9hu-1_HC4LC4 and CA9hu-2_HC4LC5). C-33a_CA IX cells incubated in the absence of humanized antibodies are marked as "negative control".

DETAILED DESCRIPTION OF THE INVENTION

Abbreviations:

Throughout the detailed description and examples of the invention the following abbreviations will be used:
3D three-dimensional
ADCC antibody-dependent cell-mediated cytotoxicity
ccRCC clear cell renal cell carcinoma
CA IX carbonic anhydrase IX
CDC complement dependent cytotoxicity
CDR complementarity determining regions
CRA cytokine release assays
DOX doxorubicin
ELISA enzyme-linked immunosorbent assay
FCS fetal calf serum
FR framework region
HER-2 human epidermal growth factor receptor 2
HIF-1 hypoxia-inducible factor 1
HRE hypoxia-response element
HVR hypervariable region
IFNγ interferon γ
IL interleukin
IMGT Immunogenetics Information System
INN international nonproprietary names
kDa kilodalton
$K_D$ dissociation constant
mAb monoclonal antibody
M molar
MCT monocarboxylate transporter
MHC major histocompatibility complex
PBMC peripheral blood mononuclear cells
PBS phosphate-buffered saline
PCR polymerase chain reaction
PD-1 programmed cell death protein 1
PD-L1 programmed cell death-ligand 1
PG proteoglycan-like region

12

PKA protein kinase A
PPA Proteome Profiler Array
RFP red fluorescent protein
SEB staphylococcal enterotoxin B
SPR surface plasmon resonance
TNBC triple-negative breast cancer
TNFα tumor-necrosis factor α
$V_H$ immunoglobulin heavy chain variable region
$V_L$ immunoglobulin light chain variable region
VEGF vascular endothelial growth factor
VHL von Hippel-Lindau
WHO World Health Organization
Cell Lines:
8-MG-BA human glioblastoma cancer cells (Cellosaurus CVCL_1052)
42-MG-BA human glioblastoma cancer cells (Cellosaurus CVCL_1798)
BT-20 human breast carcinoma cells (ATCC HTB-19)
C-33a human cervical carcinoma cells (ATCC HTB-31)
JIMT-1 human breast carcinoma cells (HMS LINCS Database ID: 51118)
HT1080 human fibrosarcoma cancer cells (ATCC CCL-121)
Definitions:

So that the invention may be more readily understood, certain technical and scientific terms are specifically defined below. Unless specifically defined elsewhere in this document, all technical and scientific terms used herein have the meaning commonly understood by one of ordinary skill in the art to which this invention belongs.

The term "CA IX" is used to refer to the protein product of the CA9 gene (e.g. NP_001207.2).

The terms "anti-CA IX antibody", "an antibody which recognizes CA IX", "an antibody against CA IX" and "an antibody to CA IX" are interchangeable, and used herein to refer to an antibody that binds to the CA IX protein (such that the antibody is useful as a diagnostic and/or therapeutic agent in targeting CA IX).

The term "antigen" as used herein refers to a molecule or a portion of a molecule capable of eliciting antibody formation and being bound by an antibody. An antigen may have one or more than one epitope. The specific reaction is meant to indicate that the antigen will react, in a highly selective manner, with its corresponding antibody and not with the multitude of other antibodies, which may be evoked by other antigens. An antigen according to the present invention is a CA IX protein or a fragment thereof.

The term "antigenic determinant" or "epitope" as used herein refers to the region of an antigen molecule that specifically reacts with a particular antibody. Peptide sequences derived from an epitope can be used, alone or in conjunction with a carrier moiety, applying methods known in the art, to immunize animals and to produce additional, or monoclonal antibodies. Isolated peptides derived from an epitope may be used in diagnostic methods to detect antibodies and as therapeutic agents when inhibition of said antibodies is required.

The term "antibody" or "immunoglobulin" as used herein refers to composition of two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The antigen binding domains, Fab, include regions where the polypeptide sequence varies. The term F(ab')2 represents two Fab' arms linked together by disulfide bonds. The central axis of the antibody is termed the Fc fragment. Each heavy chain has at one end a variable domain (V$_H$) followed by a number of constant domains (C$_H$). Each light chain has a variable domain (V$_L$) at one end and a constant domain (C$_L$) at its other end, the light chain variable domain being aligned with the variable domain of the heavy chain and the light chain constant domain being aligned with the first constant domain of the heavy chain. The variable domains of each pair of light and heavy chains form the antigen-binding site. The domains on the light and heavy chains have the same general structure and each domain comprises four framework regions, whose sequences are relatively conserved, joined by three hyper-variable domains known as complementarity determining regions (CDRs 1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

An "isolated" antibody is one, which has been separated from a component of its natural environment. In some embodiments, an antibody is purified to greater than 95% or 99% purity as determined by, for example, electrophoretic or chromatographic.

The term "monoclonal antibody" as used herein refers to an antibody obtained from a population of substantially homogenous antibodies, i.e. the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The term "chimeric antibody" as used herein refers to an antibody in which a portion of the heavy and/or light chain is derived from a particular source or species, while the remainder of the heavy and/or light chain is derived from a different source.

The term "humanized antibody" as used herein refers to an antibody comprising amino acid residues from non-human HVRs and amino acid residues from human FRs. In certain embodiments, a humanized antibody will comprise substantially all of at least one, and typically two, variable domains, in which all or substantially all of the HVR (e.g. CDRs) correspond to those of a non-human antibody, and all or substantially all of the FRs correspond to those of human antibody. A humanized antibody optionally may comprise at least a portion of an antibody constant region derived from a human antibody. A "humanized form" of an antibody, e.g. a non-human antibody, refers to an antibody that has undergone humanization.

The term "acceptor human framework" for the purposes herein is a framework comprising the amino acid sequence of a heavy chain variable domain (V$_H$) framework or a light chain variable domain (V$_L$) framework derived from human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the V$_L$ acceptor human framework is identical in sequence to the V$_L$ human immunoglobulin framework sequence or human consensus framework sequence.

The term "hypervariable region" or "HVR" as used herein refers to each of the regions of an antibody variable domain, which is hypervariable in sequence and/or form structurally defined loops ("hypervariable loops"). Generally, native four-chain antibodies comprise six HVRs, three in the V$_H$, and three in the V$_L$. HVRs generally comprise amino acid residues from the hypervariable loops and/or from the "complementarity determining regions" (CDRs), the latter being of highest sequence variability and/or involved in antigen recognition.

The term "affinity" as used herein refers to the strength of the sum total of non-covalent interactions between a single binding site of a molecule (e.g. an antibody) and its binding partner (e.g. an antigen).

Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (K$_D$). Affinity can be measured by common methods known in the art, including those described herein.

The term "effector function" as used herein refers to those biological activities attributable to the Fc-region of an antibody, which vary with the antibody class. Examples of antibody effector functions include: complement dependent cytotoxicity (CDC) and antibody-dependent cell-mediated cytotoxicity (ADCC).

The term "Fc-region" as used herein refers to a C-terminal region of an immunoglobulin heavy chain that contains at least a portion of the constant region.

The term "effective amount" of an agent, e.g. a pharmaceutical formulation, as used herein refers to an amount effective, at dosages and for periods of time necessary, to achieve the desired therapeutic or prophylactic result.

The term "pharmaceutical formulation" as used herein refers to a preparation, which is in such form as to permit the biological activity of an active ingredient contained therein to be effective, and which contains no additional components which are unacceptably toxic to a subject to which the formulation would be administered.

The term "treatment" as used herein refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequence of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "subject" or "individual" as used herein refers to mammal. Mammals include, but are not limited to, domesticated animals (e.g. cows, sheep, cats, dogs, and horses), primates (e.g. humans and non-human primates such as monkeys), rabbits, and rodents (e.g. mice and rats). In certain embodiments, the subject or individual is a human.

The term "cancer" and "cancerous" as used herein refers to or describes the physiological condition in mammals that is typically characterized by unregulated cell growth. Examples of cancer include but are not limited to, carcinoma, lymphoma, blastoma, sarcoma, and leukemia. More particular examples of such cancers include squamous cell carcinoma, myeloma, small-cell lung cancer, non-small cell lung cancer, glioma, Hodgkin's lymphoma, non-Hodgkin's lymphoma, acute myeloid leukemia, multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, mesothelioma, and head and neck cancer. Particularly preferred cancers that may be treated in accordance with the present invention include those characterized by elevated expression CA IX in tested tissue samples.

The term "anti-neoplastic composition" as used herein refers to a composition useful in treating cancer comprising at least one active therapeutic agent capable of inhibiting or preventing tumor growth or function, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells.

The term "diagnosing" as used herein refers to determining presence or absence of a pathology, classifying a pathology or a symptom, determining a severity of the pathology, monitoring pathology progression, forecasting an outcome of a pathology and/or prospects of recovery.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Pharmaceutical Formulations

The pharmaceutical composition of the invention comprises a carrier for the antibody, desirably a pharmaceutically acceptable carrier. The pharmaceutically acceptable carrier can be any suitable pharmaceutically acceptable carrier. The term "pharmaceutically acceptable carrier" as used herein means one or more compatible solid or liquid fillers, diluents, other excipients, or encapsulating substances which are suitable for administration into a human or veterinary patient (e.g. a physiologically acceptable carrier or a pharmacologically acceptable carrier). The term "carrier" denotes an organic or inorganic ingredient, natural or synthetic, with which the active ingredient is combined to facilitate the application. The pharmaceutically acceptable carrier can be co-mingled with one or more of the active components, e.g. a hybrid molecule, and with each other, when more than one pharmaceutically acceptable carrier is present in the composition in a manner so as not to substantially impair the desired pharmaceutical efficacy. "Pharmaceutically acceptable" materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, e.g. acetic acid or a salt thereof, citric acid or a salt thereof, boric acid or a salt thereof, and phosphoric acid or a salt thereof. The pharmaceutical compositions also optionally can contain suitable preservatives, such as benzalkonium chloride, chlorobutanol, parabens, and thimerosal.

The formulation herein may also contain more than one active compound as necessary for the particular indication being treated, preferably those with complementary activities that do not adversely affect each other. Such molecules are suitably present in combination in amounts that are effective for the purpose intended.

The composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in *Remington's Pharmaceutical Sciences*, Mack Publishing Co., Easton, PA, 22nd edition, 2013.

The formulations to be used for in vivo administration must be sterile. This is readily accomplished by filtration through sterile filtration membranes.

Diagnostic Uses of Anti-CA IX Antibodies

The present invention provides a diagnostic composition comprising at least one humanized antibody, which specifically recognizes human CA IX, as described above.

The present invention further provides, in another aspect, a method for diagnosing a cancer in a subject in need thereof, the method comprising contacting a biological sample derived or obtained from said subject with the diagnostic composition described above, wherein a complex formation beyond a predetermined threshold is indicative of the cancer in said subject.

The present invention further provides, in another aspect, a method for determining the expression of CA IX, the method comprising contacting a biological sample with the antibodies thereof described above, and measuring the level of immune complex formation.

The present invention further provides, in another aspect, a method for diagnosing a disease or disorder associated with a CA IX protein expression, comprising the steps of incubating a biological sample with a humanized antibody as described above; detecting the bound CA IX protein using a detectable probe; comparing the amount of bound CA IX protein to a standard curve obtained from reference samples; calculating the amount of the CA IX protein in the biological sample from the standard curve; and optionally administering an appropriate treatment to the patient.

The present invention further provides, in an aspect, the use of humanized antibodies as described above, for preparation of a diagnostic composition for the diagnosis of a cancer-related disease or disorder.

The present invention further provides, in an aspect, a conjugation of the antibodies of the invention to a synthetic molecule. The synthetic molecule can be a label. Labels can be useful in diagnostic applications and can include, for example, contrast agents. A contrast agent can be a radioisotope label such as iodine ($^{131}$I or $^{125}$I), indium ($^{111}$In), technetium ($^{99}$Tc), phosphorus ($^{32}$P), carbon ($^{14}$C), tritium ($^{3}$H), other radioisotope (e.g., a radioactive ion) or a therapeutic radioisotope listed above. Additionally, contrast agents can include radiopaque materials, magnetic resonance imaging (MRI) agents, and ultrasound imaging agents, and any other contrast agents suitable for detection by a device that images a body. The synthetic molecule can also be a fluorescent label, a biologically active enzyme label, a luminescent label, or a chromophore label.

Therapeutic Uses of Anti-CA IX Antibodies

Any of the anti-CA IX antibodies provided herein may be used in therapeutic methods.

In one aspect, an anti-CA IX antibody for use as a medicament is provided. In certain embodiments, an anti-CA IX antibody for use in a method of treatment is provided.

In a further aspect, the invention provides for the use of an anti-CA IX antibody in the manufacture or preparation of a medicament.

In a further aspect, the invention provides pharmaceutical formulation comprising any of the anti-CA IX antibodies provided herein. In one embodiment, a pharmaceutical formulation comprises any of the anti-CA IX antibodies provided herein and a pharmaceutically acceptable carrier.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following administration of the additional therapeutic agent and/or adjuvant. Antibodies of the invention can also be used in combination with radiation therapy.

The invention also provides a method of treating a subject that has a disorder associated with elevated levels of CA IX. Generally, the method includes administering a therapeutically effective amount of an isolated humanized antibody of the invention to the subject. The antibody can be any anti-CA IX antibody of the invention as described above. The antibody can be administered in combination with other agents, e.g. a cytotoxic, cytostatic, anti-angiogenic, immune-checkpoint blocking agent or a therapeutic radioisotope.

Antibodies of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosage and with administration routes as described herein, or in any dosage and by any route that is empirically/clinically determined to be appropriate.

For treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatment. Depending on the type and severity of the disease, about 0.001 mg/kg to 15 mg/kg of antibody can be an initial candidate dosage for administration to the patient, whether, for example by one or more separate administrations, or by continuous infusion. For repeated administration over several days or longer, depending on the condition, the treatment would generally be sustained until a desired suppression of disease symptoms occurs. Such doses may be administered intermittently, e.g. every week or every three weeks. An initial higher loading dose, followed by one or more lower doses may be administered. The progress of this therapy is easily monitored by conventional techniques and assays.

EXAMPLES

The following examples, including the experiments conducted and results achieved are provided for illustrative purposes only and should not be construed as limiting the present invention.

Commercially available reagents referred to in the Examples were used according to manufacturer's instructions unless otherwise indicated.

Example 1

Humanized Antibodies Derived from Parental VII/20 mAb

This example demonstrates the construction and characterization of humanized antibody variants CA9hu-1.

The humanization process utilized a combination of standard CDR-grafting technologies coupled with the latest research on antibody structure and up-to-date database of mature human IgG sequences. Firstly, the VII/20 murine antibody variable domains were sequenced. The Complementarity Determining Regions (CDRs) were identified using the Immunogenetics Information System® (IMGT®) or the Kabat numbering system (Lefranc et al, *Nucleic Acid Res* 27:209-212, 1999; Lefranc et al, *Dev Comp Immunol* 27:55-77, 2003; Kabat et al, Sequences of Proteins of Immunological Interest, 5th edition, 1991). For optimal retention of CDR-loop conformation, both numbering systems were used to identify CDRs within murine variable heavy ($V_H$) as well as variable light ($V_L$) domains. Subsequently, a number of human framework sequences were identified and used as "acceptor" frameworks (in the text below) for the CDR sequences. Each of the $V_H$ domains was synthesized in-frame with a human IgG isotype constant domain sequence (allotype G1m17,1). Additionally, each of the $V_L$ domains was synthesized in-frame with a human IgK isotype constant domain sequence (allotype Km3). The entire heavy and light chain sequence was codon optimized and the DNA sequence verified.

The combination of five $V_H$ and five $V_L$ chains resulted in generation of twenty-five humanized variants having humanized variable domains [marked in the following text as heavy (HC) and light (LC) chain] and human Ig constant domains. In order to characterize twenty-five humanized antibody variants, all sequences were screened for MHC Class II binding epitopes, Fv glycosylation motifs and deamidation motifs.

Murine monoclonal antibody VII/20 (isotype IgG2a) directed to the catalytic domain of CA IX was generated in the CA IX-deficient mice (WO2003/100029; Zatovicova et al, *J Immunol Methods* 282, 117-134, 2003). Upon binding to CA IX, the VII/20 antibody undergoes efficient receptor-mediated internalization leading to the depletion of the CA IX molecules form the cell surface of cancer cells (Zatovicova et al, *Curr Pharm Des* 16, 3255-3263, 2010). Biological properties of the VII/20 mAb and its capacity to cause anti-cancer effect were evaluated in mouse xenograft model of colorectal carcinoma (Zatovicova et al, *Curr Pharm Des* 16, 3255-3263, 2010) Immediate and postponed treatment significantly reduced tumor growth suggesting that the immunotherapy with VII/20 mAb was effective against colorectal tumor cells and thus, the VII/20 mAb might serve as a tool for immunotherapeutic strategies. Moreover, to determine the uptake of the antibody into HT-29 xenografts, VII/20 antibody was labeled with Alexa Fluor-750 and visualized in Kodak In-Vivo Imaging System FX at 720exc/790em 1 and 3 days post intravenous injection into non-treated nude mice with HT-29 xenografts. Fluorescence labeled mAb VII/20 signal was accumulated in xenografts, suggesting its uptake in tumor cells. Interestingly, the antibody was detectable inside the tumors even on the day 3 after its injection.

Heavy Chain

The murine $V_H$ domain had the sequence below, which does not include the murine signal peptide sequence:

```
                                    (SEQ ID NO. 37)
EVKLVESGGGLVQPGGSLRLSCATSGFTFTDYYMHWVRQPPGMALEWLAF

IRNKASGYTPQYSASVKGRFTISRDVSQTILYLQMNTLRPEDSATYYCV

RGGHAGSNYWYFDVWGAGTTVTVSS
```

The CDR residues (underlined) were identified using the IMGT numbering system or the Kabat numbering system.

```
    CDR1 VH VII/20
                                    (SEQ ID NO. 1)
    GFTFTDYYMH

CDR2 VH VII/20
                                    (SEQ ID NO. 2)
    FIRNKASGYTPQYSASVKG

CDR3 VH VII/20
                                    (SEQ ID NO. 3)
    VRGGHAGSNYWYFDV
```

Online databases of Human IgG sequences were searched for comparison to the murine $V_H$ domain using BLAST search algorithms, and candidate human variable domains were selected from the top 200 BLAST results. These were reduced to five candidates (based on a combination of framework homology, maintaining key framework residues and canonical loop structure) and the CDRs were grafted in.

Five Acceptor Frameworks Are:

```
AGP01622
                                    (SEQ ID NO. 41)
EVQLVESGGGLVQPGGSLRLSCAASGFTFSDHYMDWVRQAPGKGLEWVAH

IRNQTHSYRTDYAASVKGRFTISRDDSKNSLYLQMNSLKIEDTAVYYCTS

PGITGSPGTAGISEYYDMDVWGQGTTVTVSS

AEX29728
                                    (SEQ ID NO. 42)
EVRLVESGGGLVQPGGSLRLSCAASGFTFSDHYMDWVRQAPGKGLEWLGR

IRKKLNSYTTQYATSVQGRFTISRDDSTNSLYLQMNSLKTEDTAIYYCAR

VSDGTWHLDYWGQGTLVTVSS

CAA85550
                                    (SEQ ID NO. 43)
QVQLVQSGGGLVQPGRSLRLSCTASGFTFGDYAMSWVRQAPGKGLEWVGF

IRSKAYGGTTEYAASVKGRFTISRDDSKTIAYLQMNSLKTEDTAVYYCTR

DYSSTVTTPPFDYWGQGTLVTVSS

AMK70325
                                    (SEQ ID NO. 44)
EVQLVESGGGLVQPGGSLRLSCAASGFTESTYEMNWVRQAPGRGLEWVAY

ISGNYNNIYYADSVKGRFTISRDNAENSLYLQMNSLRAEDTAVYYCVREG

PTHYDIFYYYMDVWGKGTTVTVSS

IGHV3-72
                                    (SEQ ID NO. 45)
EVQLVESGGGLVQPGGSLRLSCAASGFTFSDHYMDWVRQAPGKGLEWVGR

TRNKANSYTTEYAASVKGRFTISRDDSKNSLYLQMNSLKTEDTAVYYCAR

DAFDVWGQGTMVTVSS
```

With the CDRs of the murine $V_H$ grafted into these acceptor frameworks they become the humanized variants:

```
HC1 CA9hu-1
                                    (SEQ ID NO. 4)
EVQLVESGGGLVQPGGSLRLSCAASGFTFTDYYMHWVRQAPGKGLEWVAF

IRNKASGYTPQYSASVKGRFTISRDDSKNSLYLQMNSLKIEDTAVYYCVR

GGHAGSNYWYFDVWGQGTTVTVSS,
```

-continued

HC2 CA9hu-1

(SEQ ID NO. 5)

EVRLVESGGGLVQPGGSLRLSCAASGFTFTDYYMHWVRQAPGKGLEWLGF

IRNKASGYTPQYSASVKGRFTISRDDSTNSLYLQMNSLKTEDTAIYYCVR

GGHAGSNYWYFDVWGQGTLVTVSS,

HC3 CA9hu-1

(SEQ ID NO. 6)

QVQLVQSGGGLVQPGRSLRLSCTASGFTFTDYYMHWVRQAPGKGLEWVGF

IRNKASGYTPQYSASVKGRFTISRDDSKTIAYLQMNSLKTEDTAVYYCVR

GGHAGSNYWYFDVWGQGTLVTVSS,

HC4 CA9hu-1

(SEQ ID NO. 7)

EVQLVESGGGLVQPGGSLRLSCAASGFTFTDYYMHWVRQAPGRGLEWVAF

IRNKASGYTPQYSASVKGRFTISRDNAENSLYLQMNSLRAEDTAVYYCVR

GGHAGSNYWYFDVWGKGTTVTVSS,
and

HC5 CA9hu-1

(SEQ ID NO. 8)

EVQLVESGGGLVQPGGSLRLSCAASGFTFTDYYMHWVRQAPGKGLEWVGF

IRNKASGYTPQYSASVKGRFTISRDDSKNSLYLQMNSLKTEDTAVYYCVR

GGHAGSNYWYFDVWGQGTMVTVSS;

TABLE 1

Homology of humanized variants to murine V$_H$ of
VII/20 mAb. In rank order of homology the humanized
variants are HC1 = HC4 > HC2 > HC5 > HC3.

|  | Identical amino acids | Consensus amino acids |
|---|---|---|
| HC1 | 87.1% | 91.1% |
| HC2 | 86.3% | 91.1% |
| HC3 | 83.1% | 87.9% |
| HC4 | 87.1% | 91.1% |
| HC5 | 85.5% | 90.3% |

Light Chain

The murine V$_L$ domain had the sequence below, which does not include the murine signal peptide sequence:

(SEQ ID NO. 38)

DIQMNQSPSSLSASLGDTITIACHVSQNINVWLSWYQQKPGNIPKLLIYQ

ASNLHTGVPSRFTGSGSGTGFTLTISSLQPEDIATYYCQQGQSYPFTFGS

GTKLEIK

The CDR residues (underlined) were identified using the IMGT numbering system or the Kabat numbering system.

CDR1 VL VII/20

(SEQ ID NO. 9)

HVSQNINVWLS

CDR2 VL VII/20

(SEQ ID NO. 10)

QASNLHT

CDR3 VL VII/20

(SEQ ID NO. 11)

QQGQSYPFT

Online databases of Human Ig kappa sequences were searched for comparison to the murine V$_L$ domain using BLAST search algorithms, and candidate human variable domains were selected from the top 200 BLAST results. These were reduced to five candidates (based on a combination of framework homology, maintaining key framework residues and canonical loop structure) and the CDRs were grafted in.

Five Acceptor Frameworks Are:

APZ85307

(SEQ ID NO. 46)

DIQMTQSPSSLSASVGDRVTITCQASQGISRYLNWYQQKPGKAPNLLIYD

ASNLETGVPSRFSGSGSGTHFTLTISSLQPEDIATYYCQQYDNLPLTFGG

GTKVEIK

AIT38562

(SEQ ID NO. 47)

DIQMTQSPSTLSASVGDRVTITCRASQSISSWLAWYQQKPGNAPKLLIYK

ASSLESGVPSRFSGSGSGTEFTLTIGSLQPDDFVTYYCQQYNSFPYTFGQ

GTKVEIK

BAH04867

(SEQ ID NO. 48)

DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPYTFGQ

GTKLEIK

ANV21939

(SEQ ID NO. 49)

DIQMTQSPSSLSASVGDRVTINCRASQSINNYLNWYQQKPGKAPKLLIYA

ASSLQRGVPSRFSGSGSGTGFTLTIRSLQPEDYATYYCQQSYRTPYSFGQ

GTKLEIK

IGKV1-33

(SEQ ID NO. 50)

DIQMTQSPSSLSASVGDRVTITCQASQDISNYLNWYQQKPGKAPKLLIYD

ASNLETGVPSRFSGSGSGTDFTFTISSLQPEDIATYYCQQYDNLPCTFGQ

GTKLEIK

For the 3rd and 4th acceptor sequences certain residues within the frameworks were mutated to optimize interactions between charged residues in the heavy and light chains. With the CDRs of the murine V$_L$ grafted into these acceptor frameworks they become the humanized variants:

LC1 CA9hu-1

(SEQ ID NO. 12)

DIQMTQSPSSLSASVGDRVTITCHVSQNINVWLSWYQQKPGKAPNLLIYQ

ASNLHTGVPSRFSGSGSGTHFTLTISSLQPEDIATYYCQQGQSYPFTFGG

GTKVEIK

LC2 CA9hu-1

(SEQ ID NO. 13)

DIQMTQSPSTLSASVGDRVTITCHVSQNINVWLSWYQQKPGNAPKLLIYQ

ASNLHTGVPSRFSGSGSGTEFTLTIGSLQPDDFVTYYCQQGQSYPFTFGQ

GTKVEIK

-continued

```
LC3 CA9hu-1
                                          (SEQ ID NO. 14)
DIQMTQSPSSLSASVGDRVTITCHVSQNINVWLSWYQQKPGEAPKLLIYQ

ASNLHTGVPSRFSGSGSGTDFTLTISSLQPEDFATYYCQQGQSYPFTFGQ

GTKLEIK

LC4 CA9hu-1
                                          (SEQ ID NO. 15)
DIQMTQSPSSLSASVGDRVTINCHVSQNINVWLSWYQQKPGEAPKLLIYQ

ASNLHTGVPSRFSGSGSGTGFTLTIRSLQPEDYATYYCQQGQSYPFTFGQ

GTKLEIK

LC5 CA9hu-1
                                          (SEQ ID NO. 16)
DIQMTQSPSSLSASVGDRVTITCHVSQNINVWLSWYQQKPGKAPKLLIYQ

ASNLHTGVPSRFSGSGSGTDFTFTISSLQPEDIATYYCQQGQSYPFTFGQ

GTKLEIK
```

TABLE 2

Homology of humanized variants to murine $V_L$ of
VII/20 mAb. In rank order of homology the humanized
variants are LC3 = LC4 = LC5 > LC1 > LC2.

|  | Identical amino acids | Consensus amino acids |
|---|---|---|
| LC1 | 88.8% | 92.5% |
| LC2 | 86.0% | 91.6% |
| LC3 | 89.7% | 92.5% |
| LC4 | 89.7% | 92.5% |
| LC5 | 89.7% | 92.5% |

Humanization Check

The humanized variants were checked to determine whether they had been humanized in accordance with World Health Organization's (WHO) definition of humanized antibodies: The variable domain of a humanized chain has a V region amino acid sequence which, analyzed as a whole, is closer to human than to other species (assessed using the IMGT® DomainGapAlign tool) (Ehrenmann et al, *Nucleic Acids Res* 38, D301-307, 2010).

TABLE 3

WHO's assigned antibody international nonproprietary names (INN)
for the murine and humanized variants. VH0/VL0 is the murine sequence
of VII/20 and HC1-5/LC1-5 are the humanized variants.

| Sequence Name | Species | Gene and Allele | Domain Label | % Identity | Overlap | WHO INN Designation |
|---|---|---|---|---|---|---|
| VH0 | *Mus musculus* | IGHV7-3*02 | VH | 90.0 | 100 | Mouse |
| HC1 | *Homo sapiens* | IGHV3-72*01 | VH | 87.0 | 100 | Humanized |
| HC2 | *Homo sapiens* | IGHV3-72*01 | VH | 85.0 | 100 | Humanized |
| HC3 | *Homo sapiens* | IGHV3-49*04 | VH | 87.0 | 100 | Humanized |
| HC4 | *Homo sapiens* | IGHV3-72*01 | VH | 82.0 | 100 | Humanized |
| HC5 | *Homo sapiens* | IGHV3-72*01 | VH | 89.0 | 100 | Humanized |
| VL0 | *Mus musculus* | IGKV15-103*01 | V-Kappa | 85.0 | 86 | Mouse |
| LC1 | *Homo sapiens* | IGKV1-33*01 | V-Kappa | 83.2 | 95 | Humanized |
| LC2 | *Homo sapiens* | IGKV1-5*03 | V-Kappa | 84.0 | 94 | Humanized |
| LC3 | *Homo sapiens* | IGKV1-12*01 | V-Kappa | 84.2 | 95 | Humanized |
| LC4 | *Homo sapiens* | IGKV1-12*01 | V-Kappa | 80.0 | 95 | Humanized |
| LC5 | *Homo sapiens* | IGKV1-33*01 | V-Kappa | 86.3 | 95 | Humanized |

T-cell Epitope Screening

Presentation of peptide sequences in the groove of major histocompatibility complex (MHC) Class II molecules leads to activation of CD4+ T-cells and an immunogenic response. In order to reduce this response, therapeutic proteins can be designed to avoid the incorporation of "T-cell epitopes" that can activate T-cells by reducing the affinity of binding to the MHC Class II molecules.

The original murine antibody $V_H$ and $V_L$ and the humanized variant sequences were screened for MHC II binding peptides to determine that the humanization process had removed peptide sequences with high affinity using in silico algorithms. The following 8 alleles represent over 99% of the world's population and are the standard allele set used for prediction of MHC Class II epitopes: DRB1*01:01; DRB1*03:01; DRB1*04:01; DRB1*07:01; DRB1*08:02; DRB1*11:01; DRB1*13:02; DRB1*15:01 (Nielsen et al, *BMC Bioinformatics* 8:238, 2007; Wang et al, *BMC Bioinformatics* 11:568, 2010; Gonzalez-Galarza et al, *Nucleic Acid Research* 39, D913-D919, 2011; Greenbaum et al, *Immunogenetics* 63(6): 325-35, 2011).

For the $V_H$ domain the humanized variants HC2, HC3 and HC5 were top in terms of the T-cell epitope screen. However, by homology alone, humanized variants HC1 and HC4 were ranked higher in the alignment.

For the $V_L$ domain the humanized variant LC1 was ranked best from the T-cell epitope screen. Following the alignment humanized variants LC3, LC4 and LC5 all were the most homologous to the murine light chain.

Screening for Post-Translational Modifications:

Fv Glycosylation

The N-linked glycosylation motif is NXS/T where X is any amino acid except proline. This motif is not present in the murine or humanized variants of VII/20 mAb $V_H$. The motif NQS is present in the framework 1 region of the murine variant LC0. This motif was removed during the humanization process and is not present in any of the humanized light chain variants.

Deamidation

The amino acid motifs SNG, ENN, LNG, and LNN can be prone to deamidation of asparagines to aspartic acid (Chelius et al, *Anal Chem* 77(18): 6004-11, 2005). Asparagine within other motifs is less prone to deamidation. None of these four motifs are present in the murine or humanized variants derived from VII/20 mAb $V_H$ or $V_L$.

The foregoing data demonstrate the generation of twenty-five humanized variants (marked in the following text as CA9hu-1_HCxLCx) having humanized variable domains and human Ig constant domains.

Example 2

Humanized Antibodies Derived from IV/18 mAb

This example demonstrates the construction and characterization of humanized antibody variants CA9hu-2.

The humanization process utilized a combination of standard CDR-grafting technologies coupled with the latest research on antibody structure and up-to-date database of mature human IgG sequences. Firstly, the VII/20 murine antibody variable domains were sequenced. The Complementarity Determining Regions (CDRs) were identified using the Immunogenetics Information System® (IMGT®) or the Kabat numbering system. For optimal retention of CDR-loop conformation, both numbering systems were used to identify CDRs within murine variable heavy ($V_H$) as well as variable light ($V_L$) domains. Subsequently, a number of human framework sequences were identified and used as "acceptor" frameworks (in the text below) for the CDR sequences. Each of the $V_H$ domains was synthesized in-frame with a human IgG isotype constant domain sequence (allotype G1m17,1).

Additionally, each of the $V_L$ domains was synthesized in-frame with a human IgK isotype constant domain sequence (allotype Km3). The entire heavy and light chain sequence was codon optimized and the DNA sequence verified.

The combination of five $V_H$ and five $V_L$ chains resulted in generation of twenty-five humanized variants having humanized variable domains [marked in the following text as heavy (HC) and light (LC) chain] and human Ig constant domains. In order to characterize twenty-five humanized antibody variants, all sequences were screened for MHC Class II binding epitopes, Fv glycosylation motifs and deamidation motifs.

Figure 1:
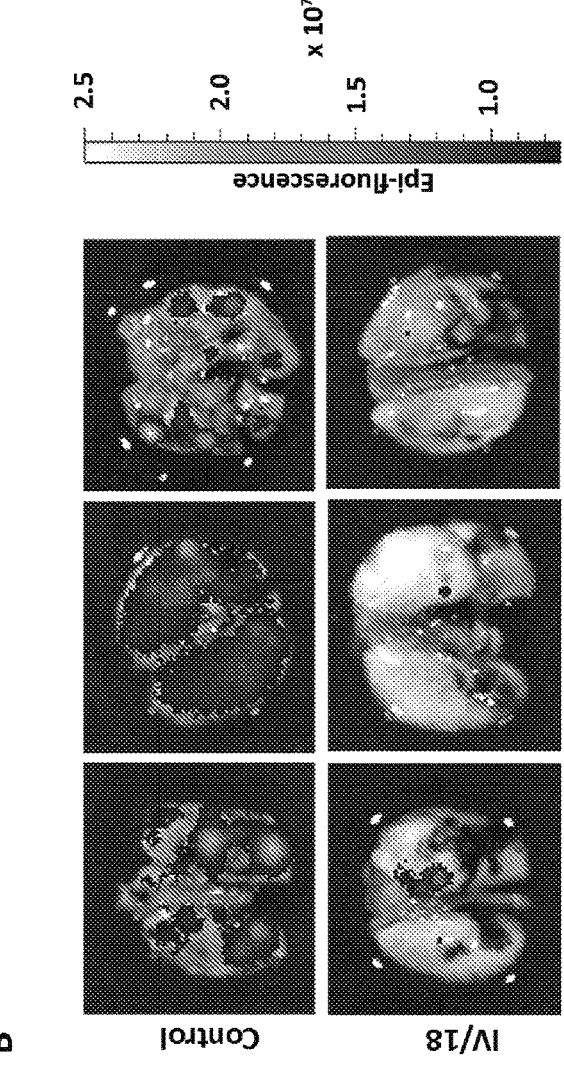
FIGS. 1A and 1B: Effect of murine IV/18 monoclonal antibody on lung metastases formation.
Figure 1:
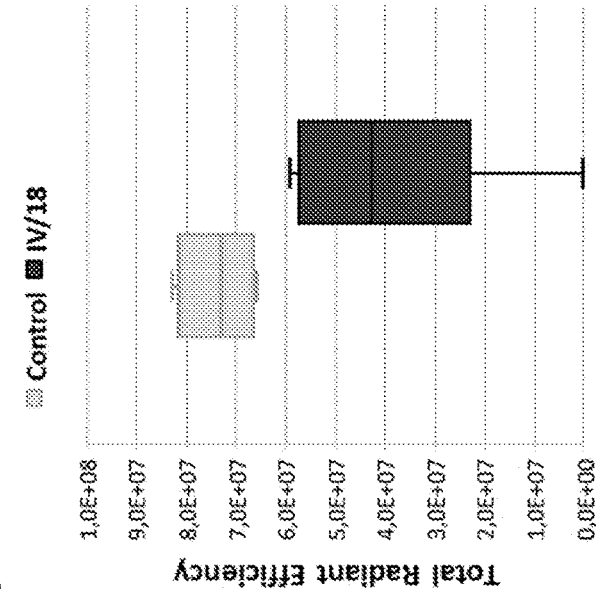

Murine monoclonal antibody IV/18 (isotype IgG2a) directed to the proteoglycan (PG)-like domain of CA IX was generated in the CA IX-deficient mice (WO2003/100029; Zatovicova et al, *J Immunol Methods* 282, 117-134, 2003). Pre-incubation of hypoxic tumor cells with the IV/18 mAb reduced the number of lung metastases in murine lung colonization model (FIG. 1A). Metastatic colonies of fluorescently tagged HT1080-red fluorescent protein (RFP) cells in PBS-perfused murine lungs were imaged ex vivo after 12 days using IVIS Caliper imaging system (FIG. 1B). Total radiant efficiency reflects the amount of cancer cells in murine lungs. Pre-incubation of HT1080-RFP cells with IV/18 mAb, and subsequent administration of three doses of antibody (50 Kg/mouse) during 12 days after the initial tail vein injection (1,500,000 cells/mouse, 10 mice per group) led to a marked decrease in lung colonization by these cells as determined by the fluorescence signal by IVIS. Metastatic colonies were evaluated shortly after tail vein inoculation, which means that reduced extravasation was a main factor behind decreased metastasis formation. These data indicate a possible benefit of anti-CA IX therapy in attenuation of tumor cell extravasation and metastasis formation.

Heavy Chain

The murine $V_H$ domain had the sequence below, which does not include the murine signal peptide sequence:

(SEQ ID NO. 39)

EVQLVETGGGLVQPKGSLKLSCAASGFTFNTNAMHWVRQAPGKGLEWVAR

IRSKSNNYTTYYADSVKDRFTISRDDSQSMLYLQMNNLKTEDTAMYYCVC

GSWFAYWGQGTLVTVSA

The CDR residues (underlined) were identified using the IMGT numbering system or the Kabat numbering system.

CDR1 VH IV/18

(SEQ ID NO. 17)

GFTFNTNAMH

CDR2 VH IV/18

(SEQ ID NO. 18)

RIRSKSNNYTTYYADSVKD

CDR3 VH IV/18

(SEQ ID NO. 19)

VCGSWFAY

Online databases of Human IgG sequences were searched for comparison to the murine $V_H$ domain using BLAST search algorithms, and candidate human variable domains were selected from the top 200 BLAST results. These were reduced to five candidates (based on a combination of framework homology, maintaining key framework residues and canonical loop structure) and the CDRs were grafted in.

Five acceptor frameworks are:

AGP01286

(SEQ ID NO. 51)

EVQLVESGGGLVQPGGSLKLSCAASGFTFSGSAMHWVRQASGKGLEWVG

RIRSKANSYATAYAASVKGRFTISRDDSKNTAYLQMNSLKTEDTAVYYC

TRLVGAIPFDYWGQGTLVTVSS

AEX29087

(SEQ ID NO. 52)

EVQLVESGGGLVQPGGSLKLSCAASGFNFSGPAIHWVRQASGKGLEWVG

RIRSKAKNFATAYAASVKGRFTISRDDSKSTAYLQMNSLKTEDTAVYYC

TTTSSSINDYWGQGTLVTVSS

ACS95862

(SEQ ID NO. 53)

QVQLVESGGGVVQPGGSLRLSCAASGFAFSSYGMHWVRQAPGRGLEWVA

FIRSDGSNTYYSDSVKGRFTISRDNSKNTLYLQVNSLRAEDTAVYYCAF

GGDYYFGYWGQGTLVTVSS

BAC01516

(SEQ ID NO. 54)

EVQLVESGGGVVQPGRSLRLSCAASGFTFSSYGMHWVRQAPGKGLEWVA

VISYDGSNKYYADSVKGRFTISRDNSKNTLYLQMNSLRAEDTAVYYCAK

GRTGDYWGQGTLVTVSS

IGHV3-73

(SEQ ID NO. 55)

EVQLVESGGGLVQPGGSLKLSCAASGFTFSGSAMHWVRQASGKGLEWVG

RIRSKANSYATAYAASVKGRFTISRDDSKNTAYLQMNSLKTEDTAVYYC

TRYYGMDVWGQGTTVTVSS

With the CDRs of the murine $V_H$ grafted into these acceptor frameworks they become the humanized variants:

HC1 CA9hu-2

(SEQ ID NO. 20)

EVQLVESGGGLVQPGGSLKLSCAAS<u>GFTFNTNAMH</u>WVRQASGKGLEWVG

<u>RIRSKSNNYTTYYADSVKD</u>RFTISRDDSKNTAYLQMNSLKTEDTAVYYC

VC<u>GSWFAY</u>WGQGTLVTVSS

HC2 CA9hu-2

(SEQ ID NO. 21)

EVQLVESGGGLVQPGGSLKLSCAAS<u>GFTFNTNAMH</u>WVRQASGKGLEWVG

<u>RIRSKSNNYTTYYADSVKD</u>RFTISRDDSKSTAYLQMNSLKTEDTAVYYC

VC<u>GSWFAY</u>WGQGTLVTVSS

HC3 CA9hu-2

(SEQ ID NO. 22)

QVQLVESGGGVVQPGGSLRLSCAAS<u>GFTFNTNAMH</u>WVRQAPGRGLEWVA

<u>RIRSKSNNYTTYYADSVKD</u>RFTISRDNSKNTLYLQVNSLRAEDTAVYYC

VC<u>GSWFAY</u>WGQGTLVTVSS

HC4 CA9hu-2

(SEQ ID NO. 23)

EVQLVESGGGVVQPGRSLRLSCAAS<u>GFTFNTNAMH</u>WVRQAPGKGLEWVA

<u>RIRSKSNNYTTYYADSVKD</u>RFTISRDNSKNTLYLQMNSLRAEDTAVYYC

VC<u>GSWFAY</u>WGQGTLVTVSS

HC5 CA9hu-2

(SEQ ID NO. 24)

EVQLVESGGGLVQPGGSLKLSCAAS<u>GFTFNTNAMH</u>WVRQASGKGLEWVG

<u>RIRSKSNNYTTYYADSVKD</u>RFTISRDDSKNTAYLQMNSLKTEDTAVYYC

VC<u>GSWFAY</u>WGQGTTVTVSS

TABLE 4

Homology of humanized variants to murine $V_H$ of
IV/18 mAb. In rank order of homology the humanized
variants are HC2 > HC1 > HC5 > HC4 > HC3.

| | Identical amino acids | Consensus amino acids |
|---|---|---|
| HC1 | 90.6% | 94.0% |
| HC2 | 91.5% | 94.9% |
| HC3 | 86.3% | 93.2% |
| HC4 | 88.0% | 93.2% |
| HC5 | 89.7% | 93.2% |

Light Chain

The murine $V_L$ domain had the sequence below, which does not include the murine signal peptide sequence:

(SEQ ID NO. 40)

DIVMTQSPSSLAMSLGQKVTMSC<u>KSSQSLLNSSNQKNYLA</u>WFQQKPGQS

PKLLVY<u>FTSTRQS</u>GVPDRFIGSGSGTDFTLTISSVQAEDLADYFC<u>QQHY</u>

<u>SIPLT</u>FGAGTKLELK

The CDR residues (underlined) were identified using the IMGT numbering system or the Kabat numbering system.

CDR1 VL IV/18

(SEQ ID NO. 25)

KSSQSLLNSSNQKNYLA

CDR2 VL IV/18

(SEQ ID NO. 26)

FTSTRQS

CDR3 VL IV/18

(SEQ ID NO. 27)

QQHYSIPLT

Online databases of Human Ig kappa sequences were searched for comparison to the murine $V_L$ domain using BLAST search algorithms, and candidate human variable domains were selected from the top 200 BLAST results. These were reduced to five candidates (based on a combination of framework homology, maintaining key framework residues and canonical loop structure) and the CDRs were grafted in.

Five acceptor frameworks are:

AAW69164

(SEQ ID NO. 56)

DVVMTQSPDSLAVSLGERVTINC<u>KSSQSVLNTSNNKNYL</u>VWYQQKPGQS

PKLLIY<u>LASTREF</u>GVPDRFSG SGSGTDFTLTISSLQAEDVAVYYC<u>QQY</u>

<u>HSSPHT</u>FGQGTKLEIK

CAI99839

(SEQ ID NO. 57)

DIVMTQSPDSLAVSLGERATINC<u>KSSQSVLYNSNNKNYL</u>AWFQQKPGQP

PNLVIY<u>WASTRES</u>GVPDRFSG SGSGTDFTLTINSLQAEDVAVYFC<u>LQY</u>

<u>YSTPLT</u>FGQGTQVEIK

AMK70392

(SEQ ID NO. 58)

DIQMTQSPDSLAVSLGERATINC<u>KASQSVLYSSKNKNYL</u>AWYQQKPGQP

PKLLIY<u>RASTRDS</u>GVPDRFSG SGSGTDFTLTISSLQAEDVAVYFC<u>QQY</u>

<u>YSTPQT</u>FGQGTKVEIK

ALV87854

(SEQ ID NO. 59)

DIVMTQSPDSLAVSLGERATINC<u>KSSQSVLYRSKNKNYL</u>AWFQQKPGQP

PKVLIY<u>STSTRAS</u>GVPDRFTG SGSGTDFTLTISSLQAEDVAVYYC<u>LQY</u>

<u>YITPYT</u>FGQGTKLEIK

IGKV4-1

(SEQ ID NO. 60)

DIVMTQSPDSLAVSLGERATINC<u>KSSQSVLYSSNNKNYL</u>AWYQQKPGQP

PKLLIY<u>WASTRES</u>GVPDRFSGSGSGTDFTLTISSLQAEDVAVYYC<u>QQYY</u>

<u>STPYT</u>FGQGTKLEIK

With the CDRs of the murine $V_L$ grafted into these acceptor frameworks they become the humanized variants:

LC1 CA9hu-2

(SEQ ID NO. 28)

DVVMTQSPDSLAVSLGERVTINC<u>KSSQSLLNSSNQKNYLA</u>WYQQKPGQS

PKLLIY<u>FTSTRQS</u>GVPDRFSGSGSGTDFTLTISSLQAEDVAVYYC<u>QQHY</u>

<u>SIPLT</u>FGQGTKLEIK

-continued

LC2 CA9hu-2

(SEQ ID NO. 29)

DIVMTQSPDSLAVSLGERATINCKSSQSLLNSSNQKNYLAWFQQKPGQP

PNLVIYFTSTRQSGVPDRFSGSGSGTDFTLTINSLQAEDVAVYFCQQHY

SIPLTFGQGTQVEIK

LC3 CA9hu-2

(SEQ ID NO. 30)

DIQMTQSPDSLAVSLGERATINCKSSQSLLNSSNQKNYLAWYQQKPGQP

PKLLIYFTSTRQSGVPDRFSGSGSGTDFTLTISSLQAEDVAVYFCQQHY

SIPLTFGQGTKVEIK

LC4 CA9hu-2

(SEQ ID NO. 31)

DIVMTQSPDSLAVSLGERATINCKSSQSLLNSSNQKNYLAWFQQKPGQP

PKVLIYFTSTRQSGVPDRFTGSGSGTDFTLTISSLQAEDVAVYYCQQHY

SIPLTFGQGTKLEIK

LC5 CA9hu-2

(SEQ ID NO. 32)

DIVMTQSPDSLAVSLGERATINCKSSQSLLNSSNQKNYLAWYQQKPGQP

PKLLIYFTSTRQSGVPDRFSGSGSGTDFTLTISSLQAEDVAVYYCQQHY

SIPLTFGQGTKLEIK

TABLE 5

Homology of humanized variants to murine $V_L$ of
IV/18 mAb. In rank order of homology the humanized
variants are LC1 > LC4 = LC5 > LC3 > LC2.

|  | Identical amino acids | Consensus amino acids |
|---|---|---|
| LC1 | 85.8% | 94.7% |
| LC2 | 82.3% | 90.3% |
| LC3 | 84.1% | 92.0% |
| LC4 | 85.0% | 92.9% |
| LC5 | 85.0% | 92.9% |

Humanization Check

The humanized variants were checked to determine whether they had been humanized in accordance with WHO's definition of humanized antibodies: The variable domain of a humanized chain has a V region amino acid sequence which, analyzed as a whole, is closer to human than to other species.

TABLE 6

WHO's assigned antibody INN for the murine and humanized variants. VH0/VL0
is the murine sequence of IV/18 and HC1-5/LC1-5 are the humanized variants.

| Sequence Name | Species | Gene and Allele | Domain Label | % Identity | Overlap | WHO INN Designation |
|---|---|---|---|---|---|---|
| VH0 | *Mus musculus* | IGHV10S3*01 | VH | 98.0 | 99 | Mouse |
| HC1 | *Homo sapiens* | IGHV3-73*01 | VH | 90.8 | 98 | Humanized |
| HC2 | *Homo sapiens* | IGHV3-73*01 | VH | 89.8 | 98 | Humanized |
| HC3 | *Homo sapiens* | IGHV3-30*02 | VH | 84.7 | 98 | Humanized |
| HC4 | *Homo sapiens* | IGHV3-30*01 | VH | 85.7 | 98 | Humanized |
| HC5 | *Homo sapiens* | IGHV3-73*01 | VH | 90.8 | 98 | Humanized |
| VL0 | *Mus musculus* | IGKV8-24*01 | V-Kappa | 95.0 | 101 | Mouse |
| LC1 | *Homo sapiens* | IGKV4-1*01 | V-Kappa | 89.1 | 101 | Humanized |
| LC2 | *Homo sapiens* | IGKV4-1*01 | V-Kappa | 87.1 | 101 | Humanized |
| LC3 | *Homo sapiens* | IGKV4-1*01 | V-Kappa | 90.1 | 101 | Humanized |
| LC4 | *Homo sapiens* | IGKV4-1*01 | V-Kappa | 89.1 | 101 | Humanized |
| LC5 | *Homo sapiens* | IGKV4-1*01 | V-Kappa | 92.1 | 101 | Humanized |

T-Cell Epitope Screening

Presentation of peptide sequences in the groove of MHC Class II molecules leads to activation of CD4+ T-cells and an immunogenic response. In order to reduce this response, therapeutic proteins can be designed to avoid the incorporation of "T-cell epitopes" that can activate T-cells by reducing the affinity of binding to the MHC Class II molecules.

The original murine antibody $V_H$ and $V_L$ and the humanized variant sequences were screened for MHC II binding peptides to determine that the humanization process had removed peptide sequences with high affinity using in silico algorithms. The following 8 alleles represent over 99% of the world's population and are the standard allele set used for prediction of MHC Class II epitopes: DRB1*01:01; DRB1*03:01; DRB1*04:01; DRB1*07:01; DRB1*08:02; DRB1*11:01; DRB1*13:02; DRB1*15:01.

For the $V_H$ domain, all the humanized variants performed well in terms of the T-cell epitope screen with HC3 predicted to have the smallest germline T-cell epitope. Analysis by homology alone ranked HC2 and HC1 as closest to the parental murine sequence.

For the $V_L$ domain, all the humanized variants were ranked equally from the T-cell epitope screen. By homology alone, LC1 and LC4 were ranked highest.

Screening for Post-Translational Modifications:

Fv Glycosylation

The N-linked glycosylation motif is NXS/T where X is any amino acid except proline. This motif NYT is present in the murine CDR2 $V_H$ variant and, as CDRs were grafted in their entirety, has been carried through to all the humanized variants.

The motif NSS is present in the murine CDR1 of the light chain. Again, this motif was carried through to all the humanized variants.

Deamidation

The amino acid motifs SNG, ENN, LNG, and LNN can be prone to deamidation of asparagines to aspartic acid. Asparagine within other motifs is less prone to deamidation. None of these four motifs are present in the murine or humanized variants of IV/18 mAb $V_H$ or $V_L$.

The foregoing data demonstrate the generation of twenty-five humanized variants (marked in the following text as CA9hu-2_HCxLCx) having humanized variable domains and human Ig constant domains.

Example 3

Characterization of the Binding Capacity of the Humanized Antibodies

This example demonstrates the desirable binding properties of twenty-five humanized variants of CA9hu-1 and twenty-five humanized variants of CA9hu-2 for carbonic anhydrase IX. The antigen-binding specificity and affinity was determined using enzyme-linked immunosorbent assay (ELISA) and surface plasmon resonance (SPR), respectively.

ELISA

To evaluate the antigen-binding specificity, all twenty-five humanized variants of CA9hu-1 and CA9hu-2 were subjected to ELISA using either CA IX-positive or CA IX-negative antigen. Antigens were prepared from stably transfected C-33a cell line expressing CA IX (C-33a_CA IX) and parental mock-transfected C-33a cells without CA IX expression (C-33a_neo).

Proteins were extracted from the cell monolayer with RIPA lysis buffer (0.1% deoxycholate, 1% Triton X-100 and protease inhibitor cocktail in PBS). Protein concentrations were determined by bicinchoninic acid assay (ThermoFisher Scientific, Waltham, MA USA) according to the manufacturer's instructions. Protein extracts were diluted to final concentration 0.2 mg/ml in PBS. Protein concentration of antigen samples used in screening of antigen-antibody specific interaction tested by ELISA meets the requirements for low detergent content that could otherwise interfere throughout the analysis. 50 id of either CA IX-positive or CA IX-negative antigen was coated on the surface of microplate wells overnight at 37° C. After washing with PBS-T 0.05% Tween-20 in PBS pH7.2, 50 id of all humanized variants of CA9hu-1 and CA9hu-2 (diluted to concentration 5 μg/ml in 10% FCS in PBS-T) were added and incubated for 2 h at room temperature. Peroxidase-labeled swine anti-human IgG (diluted 1:5000 in 10% FCS in PBS-T; Sigma-Aldrich, St. Louis, MO USA) was used as detector. Parental VII/20 or IV/18 antibodies (marked as "mouse Ab") as well as chimeric HC0LC0 antibodies (having the murine variable domains and the human Ig constant domains) were used as reference samples. Results are expressed as a fold of induction and are calculated as O.D. values of absorbance measured at 492 nm from CA IX-positive antigen/O.D. values of absorbance measured at 492 nm from CA IX-negative antigen.

Figure 2:
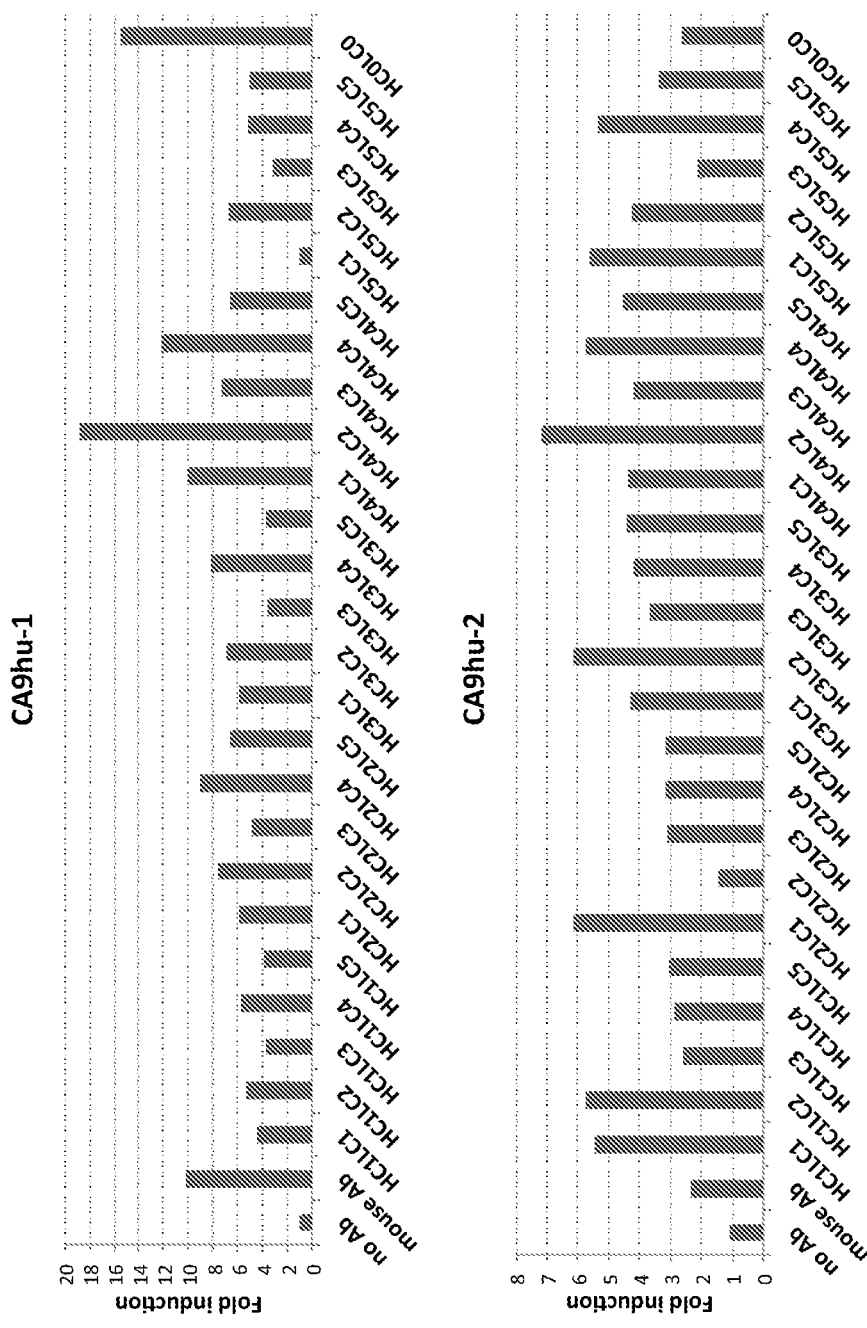
FIG. 2: Reactivity of twenty-five CA9hu-1 and CA9hu-2 variants with either CA IX-positive (C-33a_CA IX) or CA IX-negative (C-33a_neo) antigen determined via ELISA. Samples containing only antibody diluent are marked as "no Ab". Parental VII/20 (A) or IV/18 (B) (marked as "mouse Ab") as well as chimeric HC0LC0 (having the murine variable domains and the human Ig constant domains) antibodies were used as reference samples. Data in the graph are expressed as a fold of induction and are calculated as O.D. values of absorbance measured at 492 nm from CA IX-positive antigen/O.D. values of absorbance measured at 492 nm from CA IX-negative antigen.

FIG. 2 demonstrates specific and effective binding of twenty-five humanized variants of anti-CA IX antibodies. From the set of CA9hu-1 humanized antibodies, all five HC4 variants possessed very high binding efficiency against CA IX. Significantly higher binding efficiency was observed in case of the majority of CA9hu-2 humanized variants (FIG. 2).

Here we have designed a humanized antibody that specifically binds its antigen.

SPR

In order to determinate the antigen-binding affinity of humanized variants, measurements of affinity constant ($K_D$) for antibodies binding to CA IX were performed by SPR using a Biacore 2000 (T200 in case of CA9hu-2) instrument (GE Healthcare, Piscataway, NJ USA). Each humanized antibody variant was captured on the CM5 sensor chip and recombinant human CA IX (rh CA IX; 42 kDa; R&D Systems, Inc., Minneapolis MN, USA) protein as an antigen was added to the buffer flowing over the chip. The setting details of quantitative interaction analysis between humanized antibodies and rh CA IX were as follows: flow rate 30 μl/min; analysis temperature 25° C.; analysis buffer (10mM HEPES pH 7.4, 150 mM NaCl, 3 nM EDTA, 0.05% Tween 20). Results from SPR analysis are expressed as the equilibrium dissociation constant ($K_D$) (Table 7).

TABLE 7

SPR data from the analysis of twenty-five CA9hu-1 and CA9hu-2 variants expressed as $K_D$ values. Chimeric HC0LC0 antibodies (having the murine variable domains and the human Ig constant domains) were used as reference samples.

| | CA9hu-1 $K_D$ (M) | CA9hu-2 $K_D$ (M) |
|---|---|---|
| HC1LC1 | 9.70E−08 | 4.40E−08 |
| HC1LC2 | 8.00E−08 | 5.61E−08 |
| HC1LC3 | 9.60E−08 | 7.05E−08 |
| HC1LC4 | 1.00E−07 | 7.49E−08 |
| HC1LC5 | 9.60E−08 | 7.13E−08 |
| HC2LC1 | 6.00E−08 | 5.39E−08 |
| HC2LC2 | 5.30E−08 | 8.77E−08 |
| HC2LC3 | 5.10E−08 | 9.83E−08 |
| HC2LC4 | 6.00E−08 | 6.01E−08 |
| HC2LC5 | 5.60E−08 | 6.05E−08 |
| HC3LC1 | 9.10E−08 | 3.74E−08 |
| HC3LC2 | 8.10E−08 | 4.01E−08 |
| HC3LC3 | 8.20E−08 | 6.23E−08 |
| HC3LC4 | 9.70E−08 | 7.31E−08 |
| HC3LC5 | 8.30E−08 | 5.43E−08 |
| HC4LC1 | 1.52E−08 | 3.96E−08 |
| HC4LC2 | 9.10E−09 | 3.27E−08 |
| HC4LC3 | 1.07E−08 | 4.42E−08 |
| HC4LC4 | 1.52E−08 | 7.46E−08 |
| HC4LC5 | 1.23E−08 | 4.19E−08 |
| HC5LC1 | not detected | 6.98E−08 |
| HC5LC2 | 5.20E−08 | 1.05E−07 |
| HC5LC3 | 5.60E−08 | 5.72E−08 |
| HC5LC4 | 5.40E−08 | 4.73E−08 |
| HC5LC5 | 6.40E−08 | 6.51E−08 |
| HC0LC0 | 2.20E−08 | 1.31E−08 |

SPR analysis enabled us to validate all twenty-five humanized antibody variants by monitoring their binding kinetics with recombinant human CA IX protein in real time. The smaller the K D values, the greater the binding affinity of analyzed antibody. As shown in Table 7, all antibody variants possess K D values in a low nanomolar range ($10^{-7}$-$10^{-9}$) that is generally considered to be the range of high affinity antibodies. Moreover, some antibody variants from CA9hu-1 (HC4LC1, HC4LC2, HC4LC3, HC4LC4 and HC4LC5) showed even higher affinity than the chimeric variant.

According to the results obtained via ELISA and SPR analysis of the highest affinity for CA IX, the following antibody variants were selected from CA9hu-1: HC4LC1, HC4LC2, HC4LC3, HC4LC4 and HC4LC5, and from CA9hu-2: HC3LC1, HC3LC2, HC4LC1, HC4LC2 and HC4LC5.

The foregoing results demonstrate that humanized antibody variants CA9hu-1 and CA9hu-2 retain desirable specificity and affinity for their antigen and can be used to specifically distinguish tumor cells expressing CA IX.

Example 4

ADCC (Antibody-Dependent Cell-Mediated Cytotoxicity) and CDC (Complement-Dependent Cytotoxicity) Effects of the Humanized Antibodies This example demonstrates the desirable participation of humanized variants of anti-CA IX antibodies in antibody-dependent cell-mediated cytotoxicity (ADCC) and comple-ment-dependent cytotoxicity (CDC).

ADCC

To evaluate the ability of humanized antibody variants to mediate the cytotoxic effect, ADCC Reporter Bioassay System (Promega, Madison WI, USA) was applied. ADCC Reporter Bioassay System represents a bioluminescence reporter array for quantifying biological activity on pathway activation by therapeutic antibody drugs in an ADCC mechanism of action (Chung et al., *Monoclonal Antibodies* 4:326-40, 2012). It uses engineered Jurkat cells stably expressing the FcγRIIIa receptor, V158 high affinity variant, and NFAT (nuclear factor of activated T-cells) response element driving expression of firefly luciferase as effector cells. Thus, ADCC mechanism of action is quantified through the luciferase production as a result of NFAT activation.

ADCC reporter assay was performed according to the manufacturer's instructions using C-33a_CA IX as well as C-33a_neo cells. Both cell types (12,500 cells/well) were plated onto sterile 96-well plate and incubated in culture medium overnight at 37° C. Humanized antibody variants (CA9hu-1 or CA9hu-2) were diluted to 1 μg/ml in PBS and 75,000 of effector cells (according to the recommended Evaluation of the effector functions of humanized antibody variants of the invention (via ADCC reporter assay) as well as their antigen binding activity and specificity (via SPR and ELISA) resulted in the selection of the following antibody variants CA9hu-1_HC4LC4 and CA9hu-2_HC4LC5 as potential candidates.

To prove antibody-dependent cell-mediated cytotoxicity on cancer cell naturally expressing CA IX, we analyzed triple-negative breast cancer (TNBC) cell lines BT-20 and JIMT-1 as well as glioblastoma cell lines 8-MG-BA and 42-MG-BA. 24 h before analysis, cancer cell lines (except JIMT-1 cells that were incubated 48 h) were pre-incubated in hypoxia to ensure the highest CA IX expression. After hypoxic pre-incubation, 12,500 cells/well were plated onto sterile 96-well plate and incubated in culture medium overnight at 37° C. Similarly as in case of ADCC screening, ADCC reporter assay was performed according to the manufacturer's instructions. Humanized antibody variants were diluted to 1 μg/ml in PBS and 75,000 of effector cells (according to the recommended effector:target ratio 6:1) were used per well. After 6 hours of incubation, detection of firefly luciferase was performed using Bio-Glo TM Luciferase Assay Reagent.

TABLE 8

Comparison of ADCC data using selected humanized antibodies (CA9hu-1_HC4LC4 and CA9hu-2_HC4LC5) on two different glioblastoma (8-MG-BA and 42-MG-BA) and breast (BT-20 and JIMT-1) cancer cell lines. Cancer cells incubated in the absence of humanized antibodies are marked as "no Ab". Results are expressed as luminescence in relative luminescence units. Data in the table are expressed as luminescence in relative luminescence units (RLU) and represent mean ± standard deviation values.

| | no Ab | | CA9hu-1_HC4LC4 | | CA9hu-2_HC4LC5 | |
|---|---|---|---|---|---|---|
| | mean | stdev | mean | stdev | mean | stdev |
| 8-MG-BA | 6504.8 (100%) | 3061.6 | 25128.0 (386.30%) | 11827.8 | 27920.3 (429.23%) | 2722.4 |
| 42-MG-BA | 6537.5 (100%) | 368.2 | 20258.5 (309.88%) | 2110.8 | 6293.8 (96.27%) | 303.7 |
| BT-20 | 1628.0 (100%) | 171.0 | 41048.3 (2521.40%) | 2120.6 | 3296.3 (202.48%) | 780.9 |
| JIMT-1 | 2581.3 (100%) | 111.5 | 5884.0 (227.94%) | 213.0 | 2699.7 (104.58%) | 164.3 | effector:target ratio 6:1) were used per well. After 6 hours of incubation, detection of firefly luciferase was performed using BioGlo™ Luciferase Assay Reagent (Promega). Mixture of sample with ADCC assay buffer and effector cells without adding the humanized antibody is marked as "no Ab". Mixture of sample without antibody and effector cells is marked as "no Ab, no EC", and serves as "plate background". Results are expressed as luminescence in relative luminescence units (RLU) and are calculated as a fold of induction (RLU induced by humanized antibody variant/ RLU no Ab).

Figure 3:
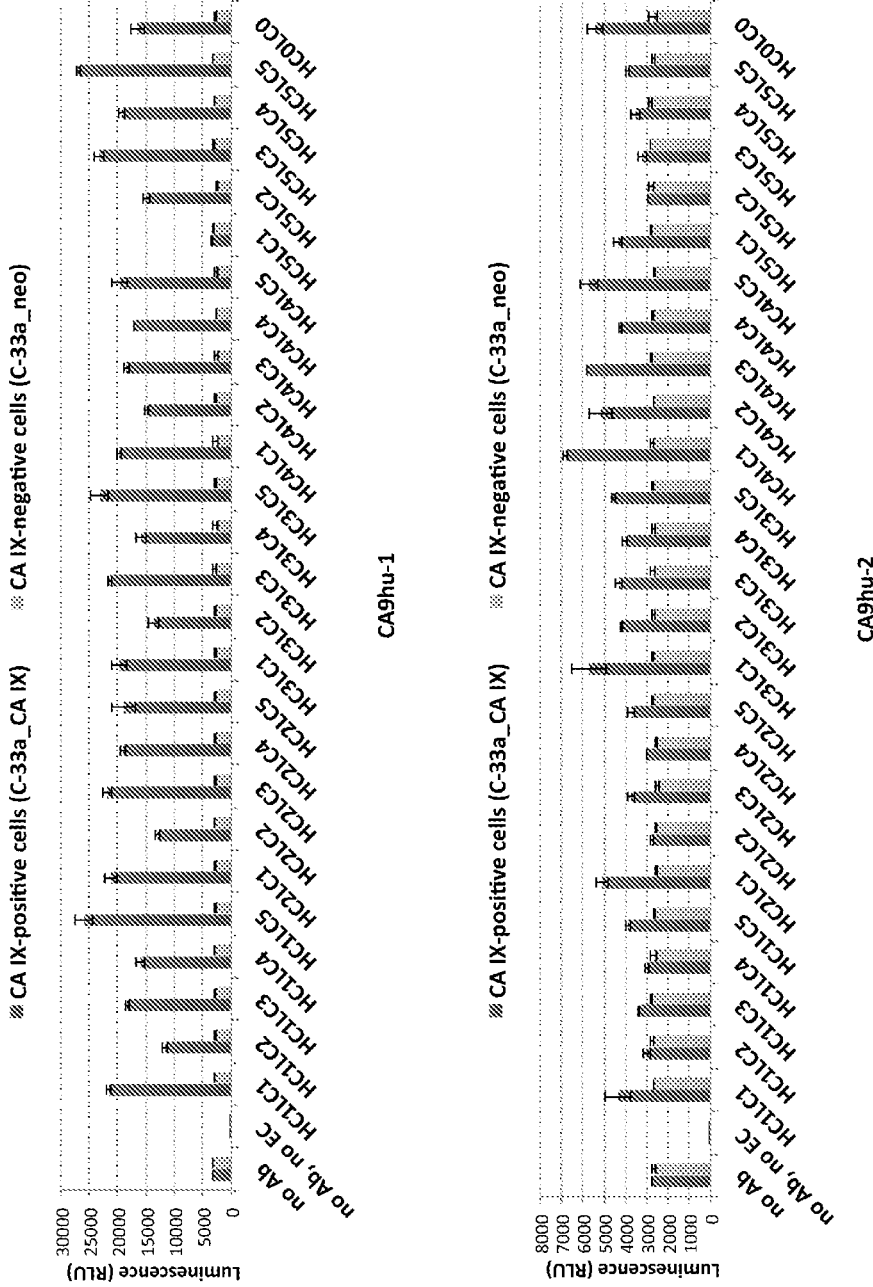

As shown in FIG. 3, CA9hu-1 variants exhibited high luminescence signal and thus, high cytotoxicity against C-33a_CA IX expressing cells. According to the fact that the RLU of samples were 100 times higher than the plate background RLU (marked as "no Ab, no EC cells"), there was no need to subtract plate background from sample RLU. Although CA9hu-2 variants appeared to be less efficacious than CA9hu-1 antibodies, they still posses two times higher capacity to activate cytotoxic pathway via ADCC against C-33a_CA IX expressing cells than C-33a_neo cells (FIG. 3).

The ADCC reporter assay enables us to analyze an earlier point in ADCC pathway through the NFAT-mediated activation of gene transcription in the effector cells. Table 8 clearly shows that selected humanized antibody variants CA9hu-1_HC4LC4 and CA9hu-2_HC4LC5 retain the ability to activate ADCC pathway and to mediate cytotoxic effect on target cells expressing CA IX. In comparison with no Ab treatment, ADCC reporter activity was elevated after incubation of cancer cells with CA9hu-1_HC4LC4 and CA9hu-2_HC4LC5 antibody variants. The highest induction (>25-fold) was observed in TNBC cells BT-20 after the treatment with CA9hu-1_HC4LC4 antibody.

CDC

To evaluate the ability of humanized antibody variants to participate on CDC, Cell Titer Blue Viability Assay Kit (Promega) was applied. Cell Titer Blue Viability Assay provides a homogenous fluorometric method for estimating the number of viable cells via indicator dye resazurin and thus, measurement of metabolic capacity of cells as an indicator of their viability. In viable cell, resazurin is reduced into highly fluorescent resorufin generating a fluorescent signal, which can be measured ($530_{Ex}/590_{Em}$). Thus, the fluorescent signal from the Cell Titer Blue Reagent is proportional to the number of viable cells.

Cell Titer Blue assay was performed according to the manufacturer's instructions using C-33a_CA IX as well as C-33a_neo cells. Both cell types (200,000 cells/well) were plated onto sterile 96-well plate and incubated in culture medium overnight at 37° C. Humanized antibody variants diluted to 5 μg/ml were added to both cell lines. Rabbit complement serum (10% from the total volume, BAG Health Care, Lich, Germany) was added to each well, mixed and incubated. Cell viability was quantified and analyzed after 24 h. Results are expressed as fluorescence measured at $530_{Ex}/590_{Em}$.

TABLE 9

Effect of selected humanized antibodies (CA9hu-1_HC4LC4 and CA9hu-2_HC4LC5) on the viability of analyzed cells +/− expressing CA IX (C-33a_CA IX versus C-33a_neo) in the presence of complement determined via Cell Titer Blue Viability Assay. Cancer cells incubated in the absence of humanized antibodies are marked as "no Ab". Data in the table are expressed as fluorescence and represent mean ± standard deviation values.

| | C-33a_CA IX | | C-33a_neo | |
|---|---|---|---|---|
| | mean | stdev | mean | stdev |
| no Ab | 3393.5 (100%) | 389.6 | 3096.5 (100%) | 289.2 |
| CA9hu-1_HC4LC4 | 1569.5 (46.25%) | 205.8 | 2931 (94.66%) | 103.2 |
| CA9hu-2_HC4LC5 | 2159 (63.62%) | 240.4 | 2807 (90.65%) | 193.7 |

Table 9 depicts the ability of humanized antibody variants CA9hu-1_HC4LC4 and CA9hu-2_HC4LC5 to affect the viability of CAIX-expressing cells in the presence of complement. After 24 h incubation with CA9hu-1_HC4LC4 and CA9hu-2_HC4LC5 variants in the presence of complement, C-33a_CA IX cells showed only 46% and 64% viability, respectively. The viability of C-33a_neo cells was almost not affected.

The foregoing results demonstrate that humanized antibody variants CA9hu-1 and CA9hu-2 can be used to specifically distinguish and consequently mediate the cytotoxic response via ADCC or CDC on tumor cells expressing CA IX.

Example 5

ADCC Effects of the Humanized Antibodies Mediated Via Peripheral Blood Mononuclear Cells in Three-Dimensional Spheroids This example demonstrates the desirable property of humanized antibodies to mediate the ADCC activity in three-dimensional cultures.

Three-dimensional (3D) cultures like multicellular spheroids are increasingly used in basic research to study cell biology and physiology under more realistic conditions. To validate the efficiency of humanized antibodies in mediating the cytotoxic effect on cancer cells in 3D system, we performed co-cultivation of TNBC BT-20 cells and peripheral blood mononuclear cells (PBMCs). PBMCs were isolated from human peripheral blood (healthy donor) by density gradient centrifugation using Ficoll-Paque Plus (GE Healthcare). In order to visualize the PBMCs within spheroids, isolated cells were stained with CellBrite Orange Cytoplasmic membrane Labelling Dye (Biotium, Hayward CA, USA). BT-20 cells were firstly stained with CellBrite Green Cytoplasmic Membrane Labelling Dye and subsequently, BT-20 spheroids were pre-formed from 10,000 cells per 25 id of culture medium in drops hanging on the lid of tissue culture dish for 7 days at 37° C. After 10 days of cultivation, pre-stained PBMC/Orange cells (2,000,000) were added together with forty BT-20 spheroids into Petri dishes and mixed with humanized antibodies (CA9hu-1_HC4LC4 or CA9hu-2_HC4LC5; 25 μg/ml). Spheroids cultivated without humanized antibodies were treated with PBS (negative control). The distribution of pre-stained PBMC cells within spheroids was analyzed after 3 days of treatment by confocal laser scanning microscope Zeiss LSM510 Meta.

To validate the effect of prolonged (11 days) co-cultivation with PBMC cells, BT-20 spheroids were collected and fixed in Carnoy's fixative solution for 2 hours and embedded into paraffin according to the standard histological procedures. Spheroid blocks were sliced into 4 μm thin sections and subjected to immunohistochemical staining using DAKO Cytomation EnVision+System-HRP (DAB; DAKO, Glostrup, Denmark) according to the manufacturer's recommendation. Primary antibody specific for CA IX mouse monoclonal M75 was diluted (1 μg/ml) and incubated for 60 min at RT Staining was visualized with DAB solution. Finally, the sections were counterstained with Mayer' s hematoxylin. The stained sections were examined with LeicaDM4500B microscope and photographed with Leica DFC480 camera.

FIG. 4 clearly shows the incorporation of pre-stained PBMCs within BT-20 spheroids. Visualization by confocal microscopy reveled more intensive incorporation of PBMCs after the treatment with humanized antibodies CA9hu-1_HC4LC4 and CA9hu-2_HC4LC5. The percentage of positive signal from PBMCs was evaluated for the entire BT-20 spheroid by ImageJ 1.38x software (Rasband, W. S., ImageJ, NIH, Bethesda MD, USA). The proportion of PBMCs-stained pixels in the entire spheroid was 3.811% and 6.624% after the treatment with CA9hu-1_HC4LC4 and CA9hu-2_HC4LC5, respectively. In case of untreated spheroids, only 2.781% of PBMC-positive pixels were revealed. The effect of prolonged treatment of BT-20 spheroids with PBMCs and humanized antibodies was examined after 11 days. As shown in FIG. 4, significant morphological changes were observed after the co-cultivation of BT-20 spheroids with human PBMCs and treatment with humanized antibodies. The immunohistochemical analysis was employed to visualize the CA IX expression across the BT-20 spheroids.

The foregoing results demonstrate that the humanized antibodies CA9hu-1_HC4LC4 and CA9hu-2_HC4LC5 of the invention facilitate the ADCC response in 3D cultures-spheroids.

Example 6

Effect of Humanized Antibodies on Cell Viability

This example demonstrates the desirable property of humanized antibodies not to affect cell viability.

To estimate the effect of humanized antibodies on cell viability, Cell Titer Blue Viability assay was performed similarly as in Example 4 (in the absence of complement), and according to the manufacturer's instructions using C-33a_CA IX as well as C-33a_neo cells. Both cell types (200,000 cells/well) were plated onto sterile 96-well plate and incubated in culture medium overnight at 37° C. Humanized antibody variants (CA9hu-1_HC4LC4 and CA9hu-2_HC4LC5) diluted to 5μg/ml were added to both cell lines. Cell viability was measured after 24 h. The fluorescent signal from the Cell Titer Blue Reagent is proportional to the number of viable cells.

TABLE 10

Effect of selected humanized antibodies (CA9hu-1_HC4LC4 and CA9hu-2_HC4LC5) on the viability of analyzed cells +/− expressing CA IX (C-33a_CA IX versus C-33a_neo) determined via Cell Titer Blue Viability Assay. Cancer cells incubated in the absence of humanized antibodies are marked as "no Ab". Data in the table are expressed as fluorescence and represent mean ± standard deviation values.

| | C-33a_CA IX | | C-33a_neo | |
|---|---|---|---|---|
| | mean | stdev | mean | stdev |
| no Ab | 7398 (100%) | 192.3 | 7594.5 (100%) | 34.6 |
| CA9hu-1_HC4LC4 | 7819.5 (105.7%) | 569.2 | 7512.5 (98.9%) | 368.4 |
| CA9hu-2_HC4LC5 | 7842 (106%) | 291.3 | 8263 (108.8%) | 718.4 |

As shown in Table 10, Cell Titer Blue Viability Assay revealed that the viability of treated C-33a cells, neither CA IX-positive nor CA IX-negative, was not affect after 24 h.

The foregoing data demonstrate that the humanized antibody variants of the invention, CA9hu-1_HC4LC4 and CA9hu-2_HC4LC5, do not exert toxic effect on treated cancer cells.

Example 7

Prediction of the Humanized Antibody Safety Via Cytokine Release Assay ("Cytokine Storm")

This example demonstrates the desirable property of selected humanized antibody variants in an in vitro cytokine release assay.

Cytokine release assays (CRAs) are best used for hazard identification but not risk quantification, and can help to understand potential risk and inform risk mitigation strategies (Vidal et al, *Cytokine* 51: 213-215, 2010). CRAs could be used to rank therapies by predicted safety and may provide additional data on the potential mechanisms for cytokine release in humans. Drugs targeting membrane-bound antigens or receptors carry a greater risk of inducing cytokine release than those targeting soluble molecules. Measurement of cytokine release is performed in comparison to drug compounds known to cause high and low responses as controls. The assay results can inform hazard identification and relative risk estimation. The following cytokines are measured: interleukin (IL)-2, IL-4, IL-6, IL-8, IL-10, interferon γ (IFNγ), and tumor-necrosis factor a (TNFα) for a complete cytokine response profile (Suntharalingam et al, *N Engl J Med* 355(10): 1018-1028, 2006).

To evaluate cytokine release associated with humanized antibodies of the invention, CRA (ProImmune Ltd., Oxford, UK) was performed and analyzed using fresh whole blood samples from 20 healthy donors. Undiluted whole blood samples were incubated in the presence of tested antibodies at various concentrations (100, 10, 1, and 0.1 µg/ml) at 37° C. for 24 h. Measurement of cytokine release was performed by ProArray Ultra® microarray assay. All cytokines were quantified against a standard curve of known concentrations. Two control antibodies (Erbitux®/Cetuximab as a low response control and Campath®/Alemtuzumab as a high response control) were also included in CRA. PBS was used as an assay negative control. The assay positive control staphylococcal enterotoxin B (SEB) was used to elicit elevated cytokine release for all donors and thus, to confirm that the assay is performed within expectations.

Table 11 demonstrates results from cytokine release assay with the median values (pg/ml) for each drug/dose combination. The median response to SEB for all cytokines was greater than zero, demonstrating that donor cell have the functional capacity to produce cytokines. While Erbitux® elicited low levels of cytokine release overall, application of Campath® led to elevated levels of IL-6, IL-8 and IFNγ release in the majority of donors (clinically this drug is associated with cytokine release syndrome). Similarly as in case of Erbitux, humanized antibody variant CA9hu-1_HC4LC4 had no effect on the release of tested cytokines, which indicates a beneficial property of this particular humanized variant.

On the other hand, elevated levels of IL-6 and IL-8 were observed for CA9hu-2_HC4LC5, although only at the highest two concentrations. This result indicates elevated cytokine response for CA9hu-2_HC4LC5 and thus, a dosage as well as an appropriate application of antibody of the invention should be considered.

TABLE 11

Reactivity of CA9hu-1_HC4LC4 and CA9hu-2_HC4LC5 in Cytokine Release Assay. Two control antibodies (Erbitux ® as a low response control and Campath ® as a high response control) were also included and analyzed. PBS was used as an assay negative control and staphylococcal enterotoxin B (SEB) as positive control. Results are expressed as median cytokine levels (pg/ml) for each drug/dose combination.

| | | IL-2 (pg/ml) | IL-4 (pg/ml) | IL-6 (pg/ml) | IL-8 (pg/ml) | IL-10 (pg/ml) | IFNγ (pg/ml) | TNFα (pg/ml) |
|---|---|---|---|---|---|---|---|---|
| PBS | | 0 | 0 | 0 | 0 | 0 | 0 | 0 |
| SEB | | 38106.5 | 59.7 | 26016.9 | 4632.5 | 442.0 | 37354.4 | 3609.9 |
| CA9hu-1_HC4LC4 (µg/ml) | 100 | 0 | 0 | 0 | 0 | 0 | 0 | 0 |
| | 10 | 0 | 0 | 0 | 0 | 0 | 0 | 0 |
| | 1 | 1.4 | 0 | 0 | 0 | 0 | 0 | 0 |
| | 0.1 | 7.0 | 0 | 0 | 0 | 0 | 0 | 0 |
| CA9hu-2_HC4LC5 (µg/ml) | 100 | 0 | 0 | 4594.3 | 51.5 | 4.8 | 0 | 0 |
| | 10 | 0 | 0 | 508.6 | 0 | 0 | 0 | 0 |
| | 1 | 0 | 0 | 0 | 0 | 0 | 0 | 0 |
| | 0.1 | 0 | 0 | 0 | 0 | 0 | 0 | 0 |

TABLE 11-continued

Reactivity of CA9hu-1_HC4LC4 and CA9hu-2_HC4LC5 in Cytokine
Release Assay. Two control antibodies (Erbitux ® as a low
response control and Campath ® as a high response control)
were also included and analyzed. PBS was used as an assay negative
control and staphylococcal enterotoxin B (SEB) as positive control.
Results are expressed as median cytokine levels (pg/ml) for each drug/dose combination.

|  |  | IL-2 (pg/ml) | IL-4 (pg/ml) | IL-6 (pg/ml) | IL-8 (pg/ml) | IL-10 (pg/ml) | IFNγ (pg/ml) | TNFα (pg/ml) |
|---|---|---|---|---|---|---|---|---|
| Erbitux ® | 100 | 0 | 0 | 0 | 0 | 0 | 0 | 0 |
| (µg/ml) | 10 | 0 | 0 | 4.6 | 2.9 | 0 | 0 | 0 |
|  | 1 | 0 | 0 | 0 | 0 | 0 | 0 | 0 |
|  | 0.1 | 0 | 0 | 0 | 0 | 0 | 0 | 0 |
| Campath ® | 100 | 0 | 0 | 3307.4 | 93.1 | 0 | 753.3 | 0 |
| (µg/ml) | 10 | 0 | 0 | 1728.9 | 38.8 | 0 | 1642.9 | 0 |
|  | 1 | 0 | 0 | 1733.5 | 82.3 | 0 | 2806.9 | 36.8 |
|  | 0.1 | 0 | 0 | 851.1 | 37.4 | 0 | 1800.1 | 0 |

The cytokine release information gained in the present assay cannot be regarded as predictive of clinical outcomes. The data obtained here should form part of a wider hazard identification strategy and should be considered in the context of all other known or obtainable information about the compounds under investigation.

The foregoing results demonstrate the desirable property of humanized antibody variants CA9hu-1_HC4LC4 and CA9hu-2_HC4LC5 not to induce cytokine response (or very slightly at the highest concentrations in case of CA9hu-2).

Example 8

Internalization of Humanized Antibodies CA9hu-1

This example demonstrates the desirable property of humanized CA9hu-1 variants to induce internalization, which represents an efficient tool for cancer immunotherapy.

Effective applications of monoclonal antibodies in cancer therapy rely on their ability to specifically target cancer tissues and enter the intracellular space via receptor-mediated internalization. Out of two murine monoclonal antibodies, only VII/20 mAb directed to the catalytic domain of CA IX can trigger the antibody-mediated endocytosis.

To investigate the ability of humanized antibodies of the invention to induce internalization, we performed flow cytometry. TNBC cells, JIMT-1 as well as BT-20 (500,000 cell/60-mm Petri dishes), were incubated 48 h in hypoxia to induce the highest level of CA IX protein expression. Subsequently, the cells were incubated with humanized antibody variant CA9hu-1_HC4LC4 (25 µg/ml; marked as "treated cells") for 30 min at 4° C. to recruit CA9hu-1-CA IX complexes at the cell surface. To remove the unbound antibody, the cells were washed and then transferred to 37° C. for 3 h to allow the internalization. At the end of the internalization period, the cells were trypsinized, transferred into tubes and incubated with mouse monoclonal antibody M75 (1 µg/ml) directed to CA IX for 10 min at RT. To determinate the amount of cell-surface CA IX protein expression, TNBC cells (marked as "untreated cells") were incubated with M75 antibody (similarly as in case of treated cells). Finally, both treated and untreated cells were incubated with Alexa 488-conjugated secondary antibody (diluted 1:1,000; ThermoFisher Scientific) for 10 min at RT, and subsequently analyzed via flow cytometry.

TABLE 12

Analysis of CA IX depletion from the cell surface of TNBC
cells (BT-20 and JIMT-1) treated with the humanized antibody variant
CA9hu-1_HC4LC4. TNBC cells incubated in the absence of
humanized antibody (marked as "untreated cells") served
for quantification of the cell-surface CA IX for each cancer
cell line. Results are expressed as a median signal level
of CA IX-staining determined via flow cytometry.

|  |  | BT-20 | JIMT-1 |
|---|---|---|---|
| CA9hu-1_HC4LC4 | untreated cells | 107.59 (100%) | 86.77 (100%) |
|  | treated cells | 34.84 (32.38%) | 38.61 (44.49%) |

Table 12 depicts the depletion of CA IX from the cell surface after the treatment of BT-20 as well as JIMT-1 cancer cells with the humanized variant CA9hu-1_HC4LC4. Untreated cells incubated only in the presence of uncompetitive M75 monoclonal antibody were used for quantification of the CA IX protein expression on the surface of cancer cells (marked as "100%" in the table). When compared to untreated cells, the amount of cell-surface expression of CA IX was reduced after the treatment with humanized antibody of the invention to 32.38% in BT-20 and 44.49% in JIMT-1 cells. Percentage of the internalized CA IX was almost 68% in BT-20 and 55.5% in JIMT-1 cells, respectively.

The foregoing data demonstrate that the humanized antibody variant CA9hu-1_HC4LC4 retain the capability to induce internalization and prove the fact that the humanization did not affect this desirable property.

Example 9

Effects of Humanized Antibodies on Multicellular Aggregation

This example demonstrates the extraordinary properties of humanized antibody variants to inhibit a multicellular aggregation during detached conditions.

To validate the effect of humanized antibodies of the invention on the ability of treated cells to form multicellular aggregates, we performed multicellular aggregation analysis. The non-ionic acid poly(2-hydroxyethyl methacrylate) (poly-HEMA; Sigma-Aldrich) which inhibits matrix deposition and cell attachment was dissolved in 99% ethanol at 10 mg/ml. 6-well tissue culture plates were coated with 0.5 ml of poly-HEMA solution, allowed to dry, washed with PBS and stored at 4° C. C-33a_CA IX cells (400,000 cells/well) were added to poly-HEMA-coated wells and cultivated in the presence or absence of humanized antibody variants CA9hu-1_HC4LC4 or CA9hu-2_HC4LC5 (30 µg/ml) for 24 and 72 h.

To evaluate the ability of C-33a_CA IX cells to form multicellular aggregates, images from either treated and untreated cells were acquired and the accumulated pixel density was measured using the ImageJ software. At the end of the longer treatment (72 h), C-33a_CA IX cells were recovered, centrifuged, and subsequently analyzed via flow cytometry using propidium iodide to stain dead cells.

Multicellular aggregation of cancer cells during extracellular matrix (ECM)-detachment represents an efficient mechanism for anoikis inhibition. FIG. 5 clearly shows that the humanized antibody variants of the invention inhibit the ability of C-33a_CA IX cells to form multicellular aggregates during detached condition on poly-HEMA coated dishes. When examining the accumulated pixel density of the multicellular aggregates, almost 56% reduction was observed after 72 h of the treatment with CA9hu-2_HC4LC5 antibody. The treatment with CA9hu-1_HC4LC4 antibody seems to be less effective (almost 13% reduction comparing with untreated cells), but similarly as in case of CA9hu-2_HC4LC5, it was observed after 24 as well as 72 h.

To validate the enhanced sensitivity of C-33a_CA IX cells to anoikis after the treatment with humanized antibodies, we performed flow cytometry and propidium iodide staining.

FIG. 6 shows that both antibody variants of the invention, CA9hu-1_HC4LC4 and CA9hu-2_HC4LC5, affect the viability of C-33a_CA IX-treated cells after 72 h grown in detached conditions. The percentage of dead cells treated with CA9hu-1_HC4LC4 and CA9hu-2_HC4LC was 37.3% and 35.1%, respectively. Only 15.7% of dead cells were observed in case of C-33a_CA IX cells without antibody treatment ("negative control").

The foregoing data demonstrate the ability of humanized antibodies of the invention to inhibit multicellular aggregation of C-33a CA IX-expressing cancer cells (during detached conditions) and subsequently to enhance their sensitivity to anoikis. This mechanism of action represents an extraordinary beneficial property. Moreover, both humanized antibody variants, CA9hu-1_HC4LC4 and CA9hu-2_HC4LC5, reduced the viability of treated cells and the percentage of dead cells cultivated in the presence of humanized antibodies was higher when comparing with control cells.

Example 10

Effect of the Humanized Antibodies on Proteome/Secretome as Well as Transcriptome of the Affected Cells This example demonstrates the unexpected properties of humanized antibodies of the invention to affect the cytokine pattern as well as the expression of proteins responsible for an evasion of antitumor immunity.

The impact of the humanized antibody variants on the cytokine pattern in vitro was analyzed using Proteome Profiler Cytokine Array (PPA; R&D Systems, Inc.). PPA is a rapid, sensitive, and economic tool to simultaneously detect cytokine differences between samples on nitrocellulose membranes. PPA Cytokine Array was performed according to the manufacturer's instructions using TNBC cell line BT-incubated in hypoxia for 72 h. BT-20 cells were seeded onto 12-well plate (200,000 cell/well) and incubated in the presence or absence of humanized antibodies CA9hu-1_HC4LC4 and CA9hu-2_HC4LC5 (50 µg/ml). Cell lysates (BT-20_proteome) as well as cell culture supernatants (BT-20_secretome) were subsequently prepared and analyzed. Diluted samples were incubated with PPA membranes overnight, washed (to remove unbound material) and incubated with a cocktail of biotinylated detection antibodies. Streptavidin-HRP and chemiluminescent detection reagents were then applied and developed. Signal is produced at each capture spot corresponding to the amount of protein bound. Pixel densities on developed X-ray films were collected and analyzed by ImageJ 1.38x software. The average signal (pixel density) of the pair of duplicate spots representing each sample was determined and subsequently, an averaged background signal was subtracted from each spot. Results are expressed as a fold change after antibody treatment (Table 13).

TABLE 13

Proteome Profiler Cytokine analysis of VEGF and IL-8 in cell lysates from BT-20 cells (BT-20_proteome) as well as culture medium from BT-20 cells (BT-20_secretome) after the treatment with selected humanized antibodies (CA9hu-1_HC4LC4 and CA9hu-2_HC4LC5) for 72 h in hypoxic conditions. Cancer cells incubated in the absence of humanized antibodies are marked as "no Ab". Results are expressed as a fold change after antibody treatment.

| | BT-20_proteome | | BT-20_secretome | |
| --- | --- | --- | --- | --- |
| | VEGF | IL-8 | VEGF | IL-8 |
| no Ab | 1 | 1 | 1 | 1 |
| CA9hu-1_HC4LC4 | 0.59 | 0.65 | 0.79 | 0.84 |
| CA9hu-2HC4LC5 | 0.83 | 0.59 | 0.86 | 0.68 |

As expected, Proteome Profiler Cytokine Array revealed several differently affected cytokines (either up- or down-regulated) expressed (BT-20_proteome) or released (BT-20_secretome). The treatment with CA9hu-1_HC4LC4 and CA9hu-2_HC4LC5 humanized antibodies led to the slightly different expression pattern. However, the expression of IL-8 and VEGF was consistently down-regulated in case of secretome as well as proteome after the incubation of BT-20 cells in the presence of humanized antibodies (Table 13).

To validate the effect of humanized antibodies on the transcriptional profile of treated cells, we employed reverse transcription-quantitative real-time PCR (RT-qPCR). Thus, the expression of genes coding for proteins responsible for an evasion of antitumor immunity was quantified and analyzed using TNBC cell line BT-20. BT-20 cells pre-formed in spheroids were firstly exposed to a chemotherapeutic drug, doxorubicin (DOX; Sigma-Aldrich) at concentration 1 µM for 4 days, following the 3 days cultivation without DOX. Treatment with humanized antibody variants CA9hu-1_HC4LC4 or CA9hu-2_HC4LC5 (25 µg/ml) was performed for the whole time period (7 days). At the same time, BT-20 cells without pre-treatment with DOX were exposed to humanized antibodies for 7 days. Total RNA was extracted using TRIzol (ThermoFisher Scientific) and subsequently transcribed with High-Capacity cDNA Reverse Transcription Kit (Applied Biosystems, Foster City CA, USA). Quantitative-PCR was performed on StepOne Real-Time PCR System (Applied Biosystems) using Power SYBR Green PCR Master Mix (Applied Biosystems) and gene-specific primers for CD47 and programmed cell death-ligand 1 (PD-L1) as well as primers for β-actin that served as an internal control. The primers were as follows: CD47 sense: 5'-AGAAGGTGAAACGATCATCGAGC-3' (SEQ ID NO. 61) and CD47 antisense: 5'-CTCATCCATAC-CACCGGATCT-3' (SEQ ID NO. 62); PD-L1 sense: 5'-TGGCATTTGCTGAACGCATTT-3' (SEQ ID NO. 63) and PD-L1 antisense: 5'-AGTGCAGCCAGGTCTAAT-TGT-3' (SEQ ID NO. 64); β-actin sense: 5'-CCAACCGCGAGAAGATGACC-3' (SEQ ID NO. 65) and 13-actin antisense: 5'-GATCTTCAT-GAGGTAGTCAGT-3' (SEQ ID NO. 66). Results are expressed as a fold change after antibody treatment (Table 14).

TABLE 14

RT-qPCR analysis of the expression levels of CD47 and PD-L1 after the treatment with selected humanized antibodies (CA9hu-1_HC4LC4 and CA9hu-2_HC4LC5) for 7 days. Doxorubicin as a chemotherapeutic drug was either added (DOX+) or not added (DOX-) for the first four days of the treatment. Cancer cells incubated in the absence of humanized antibodies are marked as "no Ab". Results are expressed as a fold change after antibody treatment.

| | CD47 | | PD-L1 | |
|---|---|---|---|---|
| | average | stdev | average | stdev |
| DOX-/no Ab | 1 | 0.426 | 1 | 0.179 |
| DOX-/CA9hu-1_HC4LC4 | 1.088 | 0.056 | 0.832 | 0.066 |
| DOX-/CA9hu-2HC4LC5 | 1.042 | 0.037 | 0.891 | 0.042 |
| DOX+/no Ab | 2.249 | 0.033 | 4.940 | 0.071 |
| DOX+/CA9hu-1_HC4LC4 | 2.093 | 0.063 | 4.850 | 0.077 |
| DOX+/CA9hu-2_HC4LC5 | 1.533 | 0.237 | 3.011 | 0.026 |

As shown in Table 14, RT-qPCR analysis of total RNA isolated from BT-20 cells treated with humanized antibodies for 7 days revealed decreased expression of CD47 as well as PD-L1. The down-regulation of both mRNAs was more evident in doxorubicin-exposed (DOX+) BT-20 cells and resulted into almost 40% and more that 30% reduction of PD-L1 and CD47 expression after the treatment with CA9hu-2_HC4LC5 humanized antibody, respectively.

The foregoing data demonstrate the ability of humanized antibodies, CA9hu-1 and CA9hu-2, to affect the cytokine profile of cancer cells. VEGF and IL-8 are two potent angiogenic factors secreted by breast cancer cells, which contribute to the establishment and expansion of tumor neovasculature. Angiogenesis is a crucial for tumor progression, and pro-angiogenic molecules such as VEGF and IL-8 have been investigated as potential targets for cancer therapy. Considering the fact that the treatment of TNBC cells with humanized antibodies of the invention possesses the ability to induce some indirect effects, e.g. down-regulation of the expression of VEGF and IL-8, we assume that the CA IX-targeted therapy could bring additional therapeutic benefits for the patients.

The ability of cancer cells to evade immune system (both the innate as well as adaptive responses) plays a crucial role in cancer relapse and metastasis. CD47 is a cell-surface protein that interacts with signal regulatory protein a on macrophages to block phagocytosis. Its expression represents a major mechanism mediating evasion of innate immunity by cancer cells. PD-L1, also known as CD274, is a transmembrane protein commonly expressed on the surface of antigen presenting cells and tumor cells. PD-L1 specifically binds to its receptor PD-1, which is expressed on the surface of immune-related lymphocytes. Breakdown of the PD-L1/PD-1 interaction leads to T cells activation, proliferation, cytokine generation and cancer cell elimination. Therefore, the down-regulation of tumor PD-L1 and CD47 expression in chemotherapy-exposed cancer cells treated with humanized antibodies of the invention could result in inhibition of cancer cell growth and moreover, present an unexpected property of humanized antibodies of the invention. In addition, the coordinate inhibition of PD-L1 and CD47 expression in response to humanized antibody treatment of doxorubicin-exposed BT-20 cells provides a rationale for combining chemotherapy and anti-CA IX antibodies of the invention to improve the outcome of cancer patients.

In conclusion, the humanized antibodies of the invention were demonstrated to retain antigen-binding specificity and to possess effector functions (ADCC, CDC). Furthermore, desirable safety of the use of the humanized antibodies was determined by cytokine release assay using fresh whole blood samples from 20 donors. Specific properties, e.g. internalization of humanized variant derived from VII/20 mAb, which represents an efficient tool for cancer immunotherapy, were proved. More importantly, unexpected and extraordinary properties of humanized antibodies were revealed in multicellular aggregation assay during detached conditions and in the analysis of proteome, secretome, and transcriptome of treated cancer cells using Proteome Profiler Array and RT-qPCR. noma, mesothelioma, and head and neck cancer.

The invention claimed is:

1. A humanized antibody, comprising at least one heavy chain variable region selected from the group consisting of:

a heavy chain variable region comprising or having the sequence:

(SEQ ID NO. 33)
X$^1$VX$^2$LVX$^3$SGGGLVQPGX$^4$SLRLSCX$^5$ASGFTFTDYYMHWVRQAPGX$^6$GL

EWX$^7$X$^8$FIRNKASGYTPQYSASVKGRFTISRDX$^9$X$^{10}$X$^{11}$X$^{12}$X$^{13}$X$^{14}$YLQM

NSLX$^{15}$X$^{16}$EDTAX$^{17}$YYVRGGHAGSNYWYFDVWGX$^{18}$GTX$^{19}$VTVSS wherein
X$^1$=E or Q
X$^2$=Q or R
X$^3$=E or Q
X$^4$=G or R
X$^5$=A or T
X$^6$=K or R
X$^7$=V or L
X$^8$=A or G
X$^9$=D or N
X$^{10}$=S or A
X$^{11}$=K or T or E
X$^{12}$=N or T
X$^{13}$=S or I
X$^{14}$=L or A
X$^{15}$=K or R
X$^{16}$=T or A or I
X$^{17}$=V or I
X$^{18}$=Q or K
X$^{19}$=T or L or M; and a heavy chain variable region comprising or having the sequence:

```
                                        (SEQ ID NO. 35)
X³²VQLVESGGGX³³VQPGX³⁴SLX³⁵LSCAASGFTFNTNAMHWVRQAX³⁶G

X³⁷GLEWVX³⁸RIRSKSNNYTTYYADSVKDRFTISRDX³⁹SKX⁴⁰TX⁴¹YLQ

X⁴²NSLX⁴³X⁴⁴EDTAVYYCVCGSWFAYWGQGTX⁴⁵VTVSS
``` wherein
X³²=E or Q
X³³=L or V
X³⁴=G or R
X³⁵=K or R
X³⁶=S or P
X³⁷=K or R
X³⁸=A or G
X³⁹=D or N
X⁴⁰=N or S
X⁴¹=A or L
X⁴²=M or V
X⁴³=K or R
X⁴⁴=T or A
X⁴⁵=L or T; and
and further comprising at least one light chain variable region selected from the group consisting of:
a light chain variable region comprising or havinf sequence:

```
                                        (SEQ IDNO. 34)
DIQMTQSPSX²⁰LSASVGDRVTIX²¹CHVSQNINVWLSWYQQKPGX²²AP

X²³LLIYQASNLHTGVPSRFSGSGSGTX²⁴FTX²⁵TIX²⁶SLQPX²⁷DX²⁸X²⁹

TYYCQQGQSYPFTFGX³⁰GTKX³¹EIK
``` wherein
X²⁰=S or T
X²¹=T or N
X²²=K or N or E
X²³=N or K
X²⁴=H or E or D or G
X²⁵=L or F
X²⁶=S or G or R
X²⁷=E or D
X²⁸=I or F or Y
X²⁹=A or V
X³⁰=Q or G
X³¹=V or L; and
a light chain variable region comprising or having sequence:

```
                                        (SEQ ID NO. 36)
DX⁴⁶X⁴⁷MTQSPDSLAVSLGERX⁴⁸TINCKSSQSLLNSSNQKNYLAWX⁴⁹QQK

PGQX⁵⁰PX⁵¹X⁵²X⁵³IYFTSTRQSGVPDRFX⁵⁴GSGSGTDFTLTIX⁵⁵SLQAE

DVAVYX⁵⁶CQQHYSIPLTFGQGTX⁵⁷X⁵⁸EIK
```

X⁴⁶=V or I
X⁴⁷=V or Q
X⁴⁸=V or A
X⁴⁹=Y or F
X⁵⁰=S or P
X⁵¹=K or N
X⁵²=L or V
X⁵³=L or V

X⁵⁴=S or T
X⁵⁵=S or N
X⁵⁶=Y or F
X⁵⁷=K or Q
X⁵⁸=L or V.

2. The humanized antibody according to claim 1, containing the heavy chain regions having SEQ ID NO. 33 and the light chain regions having SEQ ID NO. 34.

3. The humanized antibody according to claim 1, containing the heavy chain regions of SEQ ID NO. 35 and the light chain regions of SEQ ID NO. 36.

4. The humanized antibody according to claim 1, which has human IgG constant regions allotype G1m17,1of the heavy chains and human kappa constant regions allotype Km3 of the light chains.

5. A pharmaceutical composition comprising a therapeutically effective amount of a humanized antibody of claim 1, which specifically recognizes human CA IX, and a pharmaceutically acceptable carrier, diluent or excipient.

6. A diagnostic composition comprising at least one humanized antibody of claim 1, and at least one carrier, diluent, or excipient.

7. The humanized antibody according to claim 1, comprising at least one variable region selected from the group consisting of:

a) a heavy chain variable region amino acid sequence comprising or having the sequence selected from the group consisting of

```
                                        (SEQ ID NO. 4)
EVQLVESGGGLVQPGGSLRLSCAASGFTFTDYYMHWVRQAPGKGLEWVAF

IRNKASGYTPQYSASVKGRFTISRDDSKNSLYLQMNSLKIEDTAVYYCVR

GGHAGSNYWYFDVWGQGTTVTVSS,
```

```
                                        (SEQ ID NO. 5)
EVRLVESGGGLVQPGGSLRLSCAASGFTFTDYYMHWVRQAPGKGLEWLGF

IRNKASGYTPQYSASVKGRFTISRDDSTNSLYLQMNSLKTEDTAIYYCVR

GGHAGSNYWYFDVWGQGTLVTVSS,
```

```
                                        (SEQ ID NO. 6)
QVQLVQSGGGLVQPGRSLRLSCTASGFTFTDYYMHWVRQAPGKGLEWVGF

IRNKASGYTPQYSASVKGRFTISRDDSKTIAYLQMNSLKTEDTAVYYCVR

GGHAGSNYWYFDVWGQGTLVTVSS,
```

```
                                        (SEQ ID NO. 7)
EVQLVESGGGLVQPGGSLRLSCAASGFTFTDYYMHWVRQAPGRGLEWVAF

IRNKASGYTPQYSASVKGRFTISRDNAENSLYLQMNSLRAEDTAVYYCVR

GGHAGSNYWYFDVWGKGTTVTVSS,
```
and

```
                                        (SEQ ID NO. 8)
EVQLVESGGGLVQPGGSLRLSCAASGFTFTDYYMHWVRQAPGKGLEWVGF

IRNKASGYTPQYSASVKGRFTISRDDSKNSLYLQMNSLKTEDTAVYYCVR

GGHAGSNYWYFDVWGQGTMVTVSS;
``` b) a light chain variable region amino acid sequence comprising or having the sequences selected from the group consisting of (SEQ ID NO. 12)
DIQMTQSPSSLSASVGDRVTITCHVSQNINVWLSWYQQKPGKAPNLLIYQ

ASNLHTGVPSRFSGSGSGTHFTLTISSLQPEDIATYYCQQGQSYPFTFGG

GTKVEIK, (SEQ ID NO. 13)
DIQMTQSPSTLSASVGDRVTITCHVSQNINVWLSWYQQKPGNAPKLLIYQ

ASNLHTGVPSRFSGSGSGTEFTLTIGSLQPDDFVTYYCQQGQSYPFTFGQ

GTKVEIK, (SEQ ID NO. 14)
DIQMTQSPSSLSASVGDRVTITCHVSQNINVWLSWYQQKPGEAPKLLIYQ

ASNLHTGVPSRFSGSGSGTDFTLTISSLQPEDFATYYCQQGQSYPFTFGQ

GTKLEIK, (SEQ ID NO. 15)
DIQMTQSPSSLSASVGDRVTINCHVSQNINVWLSWYQQKPGEAPKLLIYQ

ASNLHTGVPSRFSGSGSGTGFTLTIRSLQPEDYATYYCQQGQSYPFTFGQ

GTKLEIK,
and (SEQ ID NO. 16)
DIQMTQSPSSLSASVGDRVTITCHVSQNINVWLSWYQQKPGKAPKLLIYQ

ASNLHTGVPSRFSGSGSGTDFTFTISSLQPEDIATYYCQQGQSYPFTFGQ

GTKLEIK;

c) a heavy chain variable region amino acid sequence comprising or having the sequences selected from the group consisting of (SEQ ID NO. 20)
EVQLVESGGGLVQPGGSLKLSCAASGFTFNTNAMHWVRQASGKGLEWVGR

IRSKSNNYTTYYADSVKDRFTISRDDSKNTAYLQMNSLKTEDTAVYYCVC

GSWFAYWGQGTLVTVSS, (SEQ ID NO. 21)
EVQLVESGGGLVQPGGSLKLSCAASGFTFNTNAMHWVRQASGKGLEWVGR

IRSKSNNYTTYYADSVKDRFTISRDDSKSTAYLQMNSLKTEDTAVYYCVC

GSWFAYWGQGTLVTVSS, (SEQ ID NO. 22)
QVQLVESGGGVVQPGGSLRLSCAASGFTENTNAMHWVRQAPGRGLEWVAR

IRSKSNNYTTYYADSVKDRFTISRDNSKNTLYLQVNSLRAEDTAVYYCVC

GSWFAYWGQGTLVTVSS,

-continued (SEQ ID NO. 23)
EVQLVESGGGVVQPGRSLRLSCAASGFTFNTNAMHWVRQAPGKGLEWVAR

IRSKSNNYTTYYADSVKDRFTISRDNSKNTLYLQMNSLRAEDTAVYYCVC

GSWFAYWGQGTLVTVSS,
and (SEQ ID NO. 24)
EVQLVESGGGLVQPGGSLKLSCAASGFTFNTNAMHWVRQASGKGLEWVGR

IRSKSNNYTTYYADSVKDRFTISRDDSKNTAYLQMNSLKTEDTAVYYCVC

GSWFAYWGQGTTVTVSS;

and
d) a light chain variable region amino acid sequence comprising or having the sequences selected from the group consisting of (SEQ ID NO. 28)
DVVMTQSPDSLAVSLGERVTINCKSSQSLLNSSNQKNYLAWYQQKPGQSP

KLLIYFTSTRQSGVPDRFSGSGSGTDFTLTISSLQAEDVAVYYCQQHYSI

PLTFGQGTKLEIK, (SEQ ID NO. 29)
DIVMTQSPDSLAVSLGERATINCKSSQSLLNSSNQKNYLAWFQQKPGQPP

NLVIYFTSTRQSGVPDRFSGSGSGTDFTLTINSLQAEDVAVYFCQQHYSI

PLTFGQGTQVEIK, (SEQ ID NO. 30)
DIQMTQSPDSLAVSLGERATINCKSSQSLLNSSNQKNYLAWYQQKPGQPP

KLLIYFTSTRQSGVPDRFSGSGSGTDFTLTISSLQAEDVAVYFCQQHYSI

PLTFGQGTKVEIK, (SEQ ID NO. 31)
DIVMTQSPDSLAVSLGERATINCKSSQSLLNSSNQKNYLAWFQQKPGQPP

KVLIYFTSTRQSGVPDRFTGSGSGTDFTLTISSLQAEDVAVYYCQQHYSI

PLTFGQGTKLEIK,
and (SEQ ID NO. 32)
DIVMTQSPDSLAVSLGERATINCKSSQSLLNSSNQKNYLAWYQQKPGQPP

KLLIYFTSTRQSGVPDRFSGSGSGTDFTLTISSLQAEDVAVYYCQQHYSI

PLTFGQGTKLEIK.

8. The humanized antibody according to claim 7, containing at least one of the heavy chain variable regions listed in a) and at least one of the light chain variable regions listed in b) in one antibody.

9. The humanized antibody according to claim 7, containing at least one of the heavy chain variable regions listed in c) and at least one of the light chain variable regions listed in d) in one antibody.

10. The humanized antibody according to claim 7, wherein the said humanized antibody contains:

a heavy chain variable region amino acid sequence comprising or having the sequence of SEQ ID NO. 7; and a light chain variable region amino acid sequence comprising or having the sequence selected from the group consisting of SEQ ID NO. 12, SEQ ID NO. 13, SEQ ID NO. 14, SEQ ID NO. 15 and SEQ ID NO. 16; or a heavy chain variable region amino acid sequence comprising or having the sequence selected from a group consisting of SEQ ID NO. 22 and SEQ ID NO. 23; and a light chain variable region amino acid sequence comprising or having the sequence selected from a group consisting of SEQ ID NO. 28, SEQ ID NO. 29 and SEQ ID NO. 32.

11. The humanized antibody according to claim 7, wherein the said humanized antibody contains:

a heavy chain variable region amino acid sequence comprising or having the sequence of SEQ ID NO. 7 and a light chain variable region amino acid sequence comprising or having the sequence of SEQ ID NO. 15; or a heavy chain variable region amino acid sequence comprising or having the sequence of SEQ ID NO. 23 and a light chain variable region amino acid sequence comprising or having the sequence of SEQ ID NO. 32.

12. A method of treatment of a condition, comprising the step of administering the pharmaceutical composition of claim 5 to a subject in need thereof, wherein the condition is a disease or disorder associated with expression, activation or function of a CA IX protein, wherein the condition is a cell proliferative disease or disorder selected from the group consisting of: squamous cell carcinoma, myeloma, small-cell lung cancer, non-small cell lung cancer, glioma, hodgkin's lymphoma, non-hodgkin's lymphoma, acute myeloid leukemia, multiple myeloma, gastrointestinal cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, mesothelioma, and head and neck cancer.

13. A method of treatment of a condition, comprising the step of administering the pharmaceutical composition of claim 5 to a subject in need thereof, wherein the condition is selected from the group consisting of breast cancer, mesothelioma, or glioblastoma expressing CA IX.

14. A method of treatment of a condition, comprising the step of administering to a subject in need thereof a therapeutically effective amount of the humanized antibody or of the pharmaceutical composition of claim 5, wherein the condition is a disease or disorder associated with expression, activation or function of a CA IX protein, wherein the condition is a cell proliferative disease or disorder, wherein the condition is selected from the group consisting of: squamous cell carcinoma, myeloma, small-cell lung cancer, non-small cell lung cancer, glioma, hodgkin's lymphoma, non-hodgkin's lymphoma, acute myeloid leukemia, multiple myeloma, gastrointestinal cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, mesothelioma, and head and neck cancer.

15. The method of claim 14, wherein the humanized antibody is administered to the subject at an appropriate daily or weekly dose, wherein the dose ranges from 0.001 mg/kg to 15 mg/kg body weight.

16. The method of claim 15 comprising administering
i) multiple, identical or different doses of the humanized antibody;
ii) multiple escalating doses of the humanized antibody; or
iii) a dose of the humanized antibody once every week, once every 2 weeks, once every 3 weeks, once every 4 weeks, or once every 5 weeks.

17. The method of claim 14, comprising 1-10 administration cycles, each cycle comprising 2-5 infusions/doses every 1-4 weeks, with the humanized antibody, followed by a break 1-8 weeks between each two cycles.

18. A method of treating of breast cancer, mesothelioma, or glioblastoma expressing CA IX, comprising administering to a subject in need thereof a therapeutically effective amount of the humanized antibody or the pharmaceutical composition of claim 5.

19. A method of reducing or inhibiting invasiveness of a tumor of a subject, comprising administering to a subject in need thereof a therapeutically effective amount of the humanized antibody or the pharmaceutical composition of claim 5, thereby reducing or inhibiting invasiveness of a tumor in a subject.

20. A method for diagnosing a cancer in a subject in need thereof, the method comprising contacting a biological sample derived or obtained from said subject with the diagnostic composition of claim 6, wherein a complex formation beyond a predetermined threshold is indicative of the cancer in said subject.

21. The method for diagnosing a cancer in a subject according to claim 20, wherein the humanized antibody, is linked, bound or conjugated to a paramagnetic, radioactive or fluorogenic moiety that is detectable upon imaging.

* * * * *